(12) United States Patent
Beard et al.

(10) Patent No.: US 7,026,487 B2
(45) Date of Patent: Apr. 11, 2006

(54) AMINES SUBSTITUTED WITH A DIHYDRONAPHTHALENYL, CHROMENYL, OR THIOCHROMENYL GROUP, A PYRIDYL GROUP AND AN ALKYL GROUP, HAVING RETINOID-LIKE BIOLOGICAL ACTIVITY

(75) Inventors: Richard L. Beard, Newport Beach, CA (US); Thong Vu, Garden Grove, CA (US); Diana F. Colon, Newport Beach, CA (US); Vidyasagar Vuligonda, Irvine, CA (US); Roshantha A. Chandraratna, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 132 days.

(21) Appl. No.: 10/612,667

(22) Filed: Jul. 2, 2003

(65) Prior Publication Data

US 2004/0097733 A1 May 20, 2004

Related U.S. Application Data

(62) Division of application No. 09/533,680, filed on Mar. 23, 2000, now Pat. No. 6,613,917.

(51) Int. Cl.
*C07D 213/74* (2006.01)
*C07D 407/12* (2006.01)
*C07D 409/12* (2006.01)

(52) U.S. Cl. ............... 546/280.1; 546/282.7; 546/304; 546/312

(58) Field of Classification Search .......... 546/280.1, 546/282.7, 304, 312
See application file for complete search history.

(56) References Cited

U.S. PATENT DOCUMENTS

| | | |
|---|---|---|
| 4,898,872 A | 2/1990 | Campbell et al. |
| 5,405,851 A | 4/1995 | Pendergast et al. |
| 5,455,265 A | 10/1995 | Chandraratna |
| 5,489,584 A | 2/1996 | Vuligonda et al. |
| 5,505,083 A | 4/1996 | Hines |
| 5,559,248 A | 9/1996 | Starrett, Jr. et al. |
| 5,616,712 A | 4/1997 | Teng et al. |
| 5,618,931 A | 4/1997 | Beard et al. |
| 5,648,514 A | 7/1997 | Johnson et al. |
| 5,763,635 A | 6/1998 | Vuligonda |
| 5,773,594 A | 6/1998 | Johnson et al. |
| 5,808,083 A | 9/1998 | Johnson et al. |
| 5,808,124 A | 9/1998 | Beard et al. |
| 5,877,207 A | 3/1999 | Klein et al. |
| 5,952,345 A | 9/1999 | Klein et al. |
| 5,958,954 A | 9/1999 | Klein et al. |

FOREIGN PATENT DOCUMENTS

| | | |
|---|---|---|
| EP | 0 661 259 A1 | 7/1995 |
| EP | 0 679 630 A | 11/1995 |
| EP | 1 061 081 A | 12/2000 |
| FR | 94 05019 | 10/1995 |
| JP | 63132864 | 6/1988 |
| WO | WO 93/11755 | 6/1993 |
| WO | WO 9845242 A1 | 10/1998 |

OTHER PUBLICATIONS

Huisgen, Rolf; Von Fraunberg, Karl; Sturm, Hans J., Tetrahedron Letters (30), 2589–94 (German) 1969.*
Babeshko, O. M.; Medyantseva, E. A.; Lyashik, O. T.; Minkin, V. I., Khimiya Geterotsiklicheskikh Soedinenii (11), 1477–81 (Russian) 1982.*
Dawson, et al., Chemistry and Biology of Synthetic Retinoids, 1990, 334–335 and 324–356, CRC Press inc.
Verma et al., Cancer Research, 1977, 2196–2201, 37.
O'Brien et al., Cancer Research, 1975, 1662–1670.
Feigner P.L. et al., Focus, 1989, 112.
Heyman et al., Cell, 1992, 397–406, 68.
Allegretto et al., J. Biol. Chem., 26625–26633, 268.
Mangelsdorf et al., The Retinoids: Biology, Chemistry, and Medicine, 319–349, Raven Press Ltd., New York.
Cheng et al., Biolochemical Pharmacology, 3099–3108, 22.
Klein et al., J. Biol. Chem., 1996, 22692–22696, 271.
Chen et al., Mol. Cell. Biol., 1987, 2745–2752, 7.
De Wet, Mol. Cell. Biol., 1987, 725–737, 7.
Nagpal et al., Embo J., 1993, 2349–2360, 12.
Johnson et al., 1999, 1321–1338, 7.
March, Advanced Organic Chemistry, $2^{nd}$ edition, McGraw–Hill Book Company, p. 357, 810,1124.
McOmie, Plenum Publishing Press, 1973 and Protecting Groups, Ed. Greene, John Wiley & Sons, 1981.
Corey et al., Tet. Lett., 1979, 399.
Omura et al., Tetrahedron, 1978, 34, 1651.
Old et al., J. Am. Chem. Soc., 1998, 120, 9722.
Lakshman et al., J. Am. Chem. Soc., 1999, 121, 6090.
J. Am. Chem. Soc., 1998, 120, 9722.
J. Am. Chem. Soc., 1999,121, 6090.
Elmori, Abdelhakim et al: "A novel synthesis of 6-demethoxyacronycine" Heterocycles (1992), 34(4), 799–806, XP001031143, p. 801; figure 12, p. 804, paragraph 1.
Loughhead, David G.: "Synthesis of des–N–methylacronycine and acronycine" J. Org. Chem. (1990), 55(7), 2245–6, XP002181701, p. 2245; figure 2.

* cited by examiner

*Primary Examiner*—Thomas C. McKenzie
(74) *Attorney, Agent, or Firm*—Gabor L. Szekeres

(57) ABSTRACT

Compounds of the formula

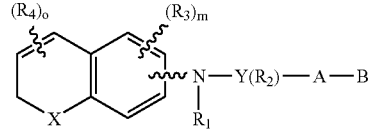

where the symbols are as defined in the specification, have retinoid agonist, antagonist or negative hormone-like biological activity.

17 Claims, No Drawings

AMINES SUBSTITUTED WITH A DIHYDRONAPHTHALENYL, CHROMENYL, OR THIOCHROMENYL GROUP, A PYRIDYL GROUP AND AN ALKYL GROUP, HAVING RETINOID-LIKE BIOLOGICAL ACTIVITY

CROSS-REFERENCE TO RELATED APPLICATION

The present application is a divisional of application Ser. No. 09/533,680, filed on Mar. 23, 2000, now U.S. Pat. No. 6,613,917.

BACKGROUND OF THE INVENTION

1. Field of the Invention

The present invention relates to novel compounds having retinoid-like biological activity. More specifically, the present invention relates to amines substituted with a dihydronaphthalenyl, chromenyl, or thiochromenyl group, an aryl or heteroaryl group and an alkyl group, which have retinoid-like, retinoid antagonist or retinoid inverse agonist-like biological activity.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis. Retinoid compounds have relatively recently been also discovered to be useful for treating type II non-insulin dependent diabetes mellitus (NIDDM).

Although pharmaceutical compositions containing retinoids have well established utility, retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_{\beta2}$ and $RAR_{\beta5}$, in RXR the subtypes are: $RXR_\alpha$, $RXR_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist) or the compound may elicit an agonist-like response on all receptor subtypes (pan-agonist). As still another alternative a compound may be a partial agonist and/or partial antagonist of certain receptor subtypes if the compound binds to but does not activate certain receptor subtype or subtypes but elicits an agonist-like response in other receptor subtype or subtypes. A pan-antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists. U.S. Pat. No. 5,877,207 titled "Synthesis and Use of Retinoid Compounds Having Negative Hormone and/or Antagonist Activities" describes the foregoing two-state model and the use of retinoid antagonist and negative hormones in detail.

Among the scientific publications Dawson and William H. Okamura, *Chemistry and Biology of Synthetic Retinoids*, published by CRC Press Inc., 1990, pages 334–335, 354 and 324–356 is of special interest as an overview of the prior art on the subject.

Among United States and foreign patents which disclose compounds having retinoid agonist, antagonist or inverse agonist like biological activity and are known to applicant the following examples include diaryl or heteroaryl substituted amines and are therefore of interest as background to the present invention: WO9845242-A1, published on Oct. 15, 1998, and French patent application number 94 05019, laid-over-to-public-inspection on Oct. 27, 1995. Published Japanese Application JP63132864 (Chemical Abstracts 110: 25516, (1988)) and United States Patent No. 4,898,872 (Chemical Abstracts 110: 231627) disclose amines substituted with a tetrahydroquinolin-6-yl and/or tetrahydroquinolinone-6-yl group and an aryl and optionally with an alkyl group, however these compounds are not described as retinoids.

Among the numerous United States and foreign patents which disclose compounds having retinoid agonist, antagonist or inverse agonist like biological activity and are known to applicant, the following examples include a dihydronaphthalene, chromen, thiochromen or dihydroquinoline ring structure and are therefore of interest as background to the present invention: U.S. Pat. Nos. 5,773,594; 5,808,083; 5,808,124; 5,877,207; 5,952,345; 5,958,954; 5,618,931; 5,489,584; 5,559,248; 5,648,514 and EPO 0 661 259 A1.

SUMMARY OF THE INVENTION

The present invention relates to compounds of Formula 1

Formula 1

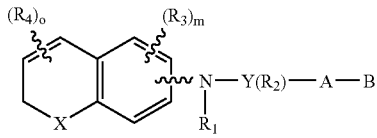

where X is O, S, or $C(R)_2$;

R is H or alkyl of 1 to 6 carbons;

$R_1$ is H, alkyl of 1 to 10 carbons, alkenyl of 2 to 6 carbons, phenyl-$C_1$–$C_6$ alkyl, or $C_1$–$C_6$-alkylphenyl;

$R_2$ is H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, $CF_3$, fluoro substituted alkyl of 1 to 6 carbons, OH, SH, alkoxy of 1 to 6 carbons, fluoroalkoxy of 1 to 6 carbons, alkylthio of 1 to 6 carbons; benxyloxy, $C_1$–$C_6$ alkyl substituted benzyloxy, halogen substituted benzyloxy, phenyloxy, $C_1$–$C_6$ alkyl substituted phenyloxy, or halogen substituted phenyloxy;

$R_4$ is independently H, alkyl of 1 to 6 carbons, or F; Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

m is an integer having the values 0 to 3;

o is an integer having the values 0 to 4;

A is $(CH_2)_q$, where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is hydrogen, COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$, is lower alkyl, phenyl or lower alkylphenyl, $R_{12}$ is lower alkyl, and $R_{13}$ is divalent alkyl radical of 2–5 carbons, or a pharmaceutically acceptable salt of said compound.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of metabolic diseases such as type II non-insulin dependent diabetes mellitus (NIDDM) and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

Alternatively, those compounds of the invention which act as antagonists or inverse agonists of one or more retinoid receptor subtypes are useful to prevent certain undesired side effects of retinoids which are administered for the treatment or prevention of certain diseases or conditions. For this purpose the retinoid antagonist and/or inverse agonist compounds of the invention may be co-administered with retinoids. The retinoid antagonist and inverse agonist compounds of the present invention are also useful in the treatment of acute or chronic toxicity resulting from overdose or poisoning by retinoid drugs or Vitamin A.

Generally speaking, the second aspect of the invention relates to the use of the novel compounds to prevent or treat diseases and conditions which are responsive to compounds that promote the expression of or bind to receptors belonging to the steroid or thyroid receptor superfamily.

This invention also relates to pharmaceutical formulations comprising a compound of Formula 1 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

BIOLOGICAL ACTIVITY, MODES OF ADMINISTRATION

Assays of Retinoid-like or Retinoid Antagonist and Inverse Agonist-like Biological Activity A classic measure of retinoic acid activity involves measuring the effects of retinoic acid on ornithine decarboxylase. The original work on the correlation between retinoic acid and a decrease in cell proliferation was done by *Verma & Boutwell*, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-O-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. "$IC_{60}$" is that concentration of the test compound which causes 60% inhibition in the ODC assay. By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$ and $RXR_\gamma$, receptors, and the ability or inability of the compounds to activate transcription of a reporter gene through these receptor subtypes can be tested. These assays are expected to demonstrate that the compounds of the present invention act as agonists of one or more of the above-described receptors. However, some of the compounds of the invention may behave as retinoid antagonists or partial antagonists and/or as inverse agonists. Because of the complex distribution of the different retinoid receptors in various organs of the mammalian body partial agonists and partial antagonists and compounds which have the characteristics of both may lend themselves to particularly useful therapeutic applications and may avoid serious side effects of conventional retinoid drugs.

As far as specific assays are concerned to demonstrate the activities of the compounds of the present invention, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et al. Biochemical Pharmacology Vol. 22 pp 3099–3108, expressly incorporated herein by reference.)

Still another transactivation assay, the "PGR assay" is described in the publication Klein et al. J. Biol. Chem. 271, 22692–22696 (1996) which is expressly incorporated herein by reference, and a detailed description is also provided below. The results of the PGR assay are also expressed in $EC_{50}$ numbers (nanomolar concentration).

RAR-P-GR holoreceptor Transactivation Assay

CV-1 cells ($4\times10^5$ cells/well).were transiently transfected with the luciferase reporter plasmid MTV-4(R5G)-Luc (0.7 ug/well) containing four copies of the R5G retinoid DNA response element along with the RXRαexpression plasmid pRS-hRXRα (0.1 ug/well) and one of the RAR-P-GR expression plasmids (0.05 ug/well) in 12 well plates via calcium phosphate precipitation Chen et al. (1987) Mol. Cell. Biol. 7, 2745–2752 as described by Klein et al. in J. Biol. Chem. 271, 22692, referenced above. The three different RAR-P-GR expression plasmids, pRS-RARα-P-GR, pcDNA3-RARβ-P-GR and pcDNA3-RARγ-P-GR, express RARα, RARβ and RARγreceptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except 1/5 of the amount of the DNA-calcium phosphate precipitant (20 µl instead of 100 µl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed with luciferase activity was measured as previously described in de Wet (1987) Mol. Cell. Biol. 7, 725–737. Luciferase values represent the mean±SEM of triplicate determinations normalized to β-galactosidase activity.

Inverse agonists are ligands that are capable of inhibiting the basal receptor activity of unliganded receptors. Recently, retinoic acid receptors (RARs) have been shown to be responsive to retinoid inverse agonists in regulating basal gene transcriptional activity. Moreover, the biological effects associated with retinoid inverse agonists are distinct from those of retinoid agonists or antagonists. For example, RAR inverse agonists, but not RAR neutral antagonists, cause a dose-dependent inhibition of the protein MRP-8 in cultured human keratinocytes differentiated with serum. MRP-8 is a specific marker of cell differentiation, which is also highly expressed in psoriatic epidermis, but is not detectable in normal human skin. Thus, retinoid inverse agonists may offer a unique way of treating diseases such as psoriasis.

The activity of retinoid inverse agonists can be tested by the procedure of Klein et al. J. Biol. Chem. 271, 22692–22696 (1996) which is expressly incorporated herein by reference. In this assay, retinoid inverse agonists are able to repress the basal activity of a RARγ-VP-16 chimeric receptor where the constituitively active domain of the herpes simplex virus (HSV) VP-16 is fused to the N-terminus of RARγ. CV-1 cells are cotransfected with RARγ-VP16, an ER-RXRα chimeric receptor and an ERE-tk-Luc chimeric reporter gene to produce a basal level of luciferase activity, as shown by Nagpal et al. EMBO J. 12, 2349–2360 (1993) expressly incorporated herein by reference. Retinoid inverse agonists are able to inhibit the basal luciferase activity in these cells in a dose dependent manner and $IC_{50}$s measured. A detailed description of the tests used for determining whether or not a compound is a retinoid antagonist or inverse agonist, and the manner of utilizing retinoid antagonists and inverse agonists is provided in U.S. Pat. No. 5,877,207, the specification of which is expressly incorporated herein by reference.

Table 1 discloses the activity of certain exemplary compounds of the invention in the above-described chimeric receptor transactivation assay, holoreceptor transactivation assay and a ligand binding assays. Particularly, the transactivation data pertaining to RAR receptors were obtained in the chimeric assay, and the data pertaining to transactivation of RXR receptors were obtained in the holoreceptor transactivation assay.

TABLE 1

| Compound Number | RAR Trans. EC$_{50}$ (nM) / RAR Bind. K$_i$ (nM) | | | RXR Trans. EC$_{50}$ (nM) / RXR Bind K$_i$ (nM) | | |
|---|---|---|---|---|---|---|
| | α | β | γ | α | β | γ |
| 88 | NA | NA | NA | 4 | 41 | 5 |
| | >10 k | >10 k | 3.5 k | (114) | (100) | (120) |
| 89 | NA | NA | NA | 3 | 12 | 21 |
| | >10 k | >100 k | 100 k | 1 | 8 | 1 |
| | | | | (108) | (93) | (105) |
| | | | | 7 | 34 | 8 |
| 90 | NA | >1 k | >1 k | 12 | 76 | 12 |
| | | (15) | (5) | (112) | (110) | (102) |
| | >10 k | >10 k | >10 k | 39 | 84 | 68 |
| 67 | NA | NA | NA | NA | NA | NA |
| | >10 k | >10 k | 10 k | 666 | >1 k | 1.3 k |
| 46 | NA | NA | NA | 1 k | >1 k | 1 k |
| | | | | (55) | (8) | (65) |
| | >10 k | >10 k | >10 k | >10 k | >10 k | >10 k |
| 52 | NA | NA | NA | 1 k | >1 k | 1 k |
| | | | | (75) | (25) | (855) |
| | >10 k | >10 k | >10 k | 1.7 k | 2.7 k | >1 k |
| 53 | NA | NA | NA | 1 k | >1 k | 1 k |
| | | | | (65) | (20) | (75) |
| | >10 k | >10 k | >10 k | 1.2 k | >1 k | >10 k |
| 44 | NA | NA | NA | >1 k | NA | >1 k |
| | | | | (30) | | (15) |
| | >10 k | >10 k | >10 k | >1 k | >1 k | >1 k |
| 45 | NA | NA | NA | 1 k | NA | >1 k |
| | | | | (50) | | (25) |
| | >10 k | >10 k | >10 k | >1 k | >1 k | >1 k |
| 47 | NA | NA | NA | 1 k | NA | 1 k |
| | | | | (65) | | (70) |
| | >10 k | >10 k | >10 k | 2.5 k | >1 k | >1 k |
| 54 | NA | NA | NA | 378 | >1 k | 1 k |
| | | | | (66) | (40) | (85) |
| | >10 k | >10 k | >10 k | 485 | >1 k | 1 k |
| 59 | NA | NA | NA | 1 k | 1 k | 1 k |
| | | | | (100) | (100) | (100) |
| | >10 k | >10 k | >10 k | 282 | 781 | >1 k |
| 60 | NA | NA | NA | 72 | 1 k | 182 |
| | | | | (88) | (60) | (124) |
| | >10 k | >10 k | 10 k | 64 | 426 | 101 |
| 23 | NA | NA | NA | 21 | 149 | 41 |
| | | | | (101) | (101) | (119) |
| | 5.3 k | 16 k | 10 k | 8 | 309 | ND |
| 25 | NA | NA | NA | <0.1 | 0.9 | 0.2 |
| | | | | (97) | (96) | (105) |
| | 3.9 k | 6.4 k | 4.4 k | 2 | 20 | ND |
| 26 | 0.5? | NA | NA | 0.3 | 4 | 0.5 |
| | (10) | | | (85) | (84) | (90) |
| | 2.2 k | 1.3 k | 4 k | 7 | 30 | ND |
| 75 | NA | NA | NA | 319 | 1 k | 1 k |
| | | | | (100) | (75) | (95) |
| | >10 k | >10 k | >10 k | 442 | 806 | ND |
| 24 | NA | NA | NA | 1 | 10 | 2 |
| | | | | (100) | (96) | (102) |
| | 7.5 k | 9.1 k | 13 k | 29 | 66 | ND |
| 153 | NA | NA | NA | NA | NA | NA |
| | 7.4 k | 4.8 k | 8.9 k | 22 | 106 | ND |
| 142 | 1.1 k? | 1 k? | >1 k? | 190 | 111 | ND |
| 145 | NA | NA | NA | NA | NA | >1 k |
| | | | | | | (10) |
| | 743? | 771? | 6 k | 229 | 475 | ND |
| 143 | NA | NA | NA | NA | NA | NA |
| | 627? | 1.7 k? | 8.4 k | 175 | 449 | ND |
| 146 | NA | NA | NA | NA | NA | NA |
| | 101? | 576? | 2.8 k | 206 | 429 | ND |
| 144 | NA | NA | NA | NA | NA | NA |
| | 3.1 k? | 2.7 k | 8.1 k | 77 | 224 | ND |
| 147 | NA | NA | NA | NA | NA | 280 |
| | | | | | | (13) |
| | 3.9 k | 4.8 k | 15 k | 241 | 501 | ND |
| 154 | NA | NA | NA | NA | NA | NA |
| | 2.8 k | 1.8 k | 6.2 k | 3 | 19 | 41 |
| 157 | NA | >1 k | NA | NA | NA | NA |
| | | (32) | | | | |
| | 3.2 k | 1.2 k | 13 k | 8 | 46 | 99 |
| 148 | NA | NA | NA | 0.5 | 8 | 2 |
| | | | | (64) | (63) | (101) |
| | 2.4 k | 7.5 k | >10 k | 5 | 15 | 37 |
| 158 | 723 | 374 | 881 | 4 | 3 | 161 |
| 155 | 165 k | 1.4 k | 2.9 k | 3 | 334? | 398? |
| 156 | NA | NA | NA | NA | NA | NA |
| | 3.9 k | 1.5 k | 4.2 k | 804 | >1 k | >1 k |

TABLE 1-continued

| Compound Number | RAR Trans. EC$_{50}$ (nM) / RAR Bind. K$_i$ (nM) | | | RXR Trans. EC$_{50}$ (nM) / RXR Bind K$_i$ (nM) | | |
|---|---|---|---|---|---|---|
| | α | β | γ | α | β | γ |
| 152 | NA | NA | NA | NA | NA | NA |
|  | 321 | 2.3 k | ND | 29 | 136 | 437 |
| 150 | NA | NA | NA | NA | NA | NA |
|  | 241 | 3.8 k | 7.9 k | 61 | 208 | 352 |
| 151 | NA | NA | NA | NA | NA | NA |
|  | 1.1 k | 1.2 k | >10 k | 54 | 155 | 248 |
| 149 | ND | ND | ND | ND | ND | ND |
| 170 | NA | NA | NA | 33 | 379 | 67 |
|  |  |  |  | (113) | (110) | (127) |
|  | >10 k | >10 k | >10 k | 64 | 190 | 61 |
| 172 | NA | NA | NA | 2 | 13 | 2 |
|  |  |  |  | (109) | (112) | (118) |
|  | 19 k | 6 k | >10 k | 0.7 | 4 | 6 |
| 173 | NA | NA | NA | 1 | 9 | 2 |
|  |  |  |  | (120) | (132) | (125) |

NA = Not Active;
ND = Not Determined
Numbers in parentheses indicate % efficacy relative to 10$^{-6}$ M ATRA (RARs) or 10$^{-6}$ M ((+)-(1'S, 2'S, 1E, 2E)-3-Methyl-5-[2'-methyl-2'-(5,5,8, 8-tetramethyl-5,6,7,8-tetrahydro-naphthalen-2-yl)-cyclopropylpenta-2,4-dienoic acid. AGN 194204) (RXRs).

As it can be seen from the foregoing assay results the preferred compounds of the invention are specific or selective agonists of RXR receptors.

Modes of Administration

The compounds of this invention may be administered systemically or topically, depending on such considerations as the condition to be treated, need for site-specific treatment, quantity of drug to be administered, and numerous other considerations.

Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form If the drug is to be administered systemically, it may be confected as a powder, pill, tablet or the like or as a syrup or elixir suitable for oral administration For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg of body weight per day would be expected to effect a therapeutic result in the treatment of many diseases for which these compounds are useful.

The partial or pan retinoid antagonist and/or retinoid inverse agonist compounds of the invention, when used to take advantage of their antagonist and/or inverse agonist property, can be co-administered to mammals, including humans, with retinoid agonists and, by means of pharmacological selectivity or site-specific delivery, preferentially prevent the undesired effects of certain retinoid agonists. The antagonist and/or inverse agonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist and/or inverse agonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist or inverse agonist compounds of the present invention block or diminish RAR activation, they are suitable for treating the foregoing toxicities.

Generally speaking, for therapeutic applications in mammals, the antagonist and/or inverse agonist compounds of the invention can be administered enterally or topically as an antidote to vitamin A, or antidote to retinoid toxicity resulting from overdose or prolonged- exposure, after intake of the causative factor (vitamin A, vitamin A precursor, or other retinoid) has been discontinued. Alternatively, the antagonist and/or inverse agonist compounds of the invention are co-administered with retinoid drugs, in situations where the retinoid provides a therapeutic benefit, and where the co-administered antagonist and/or inverse agonist compound alleviates or eliminates one or more undesired side effects of the retinoid. For this type of application the antagonist and/or inverse agonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions suspensions, creams, ointments, gels, salves, lotions and the like, using such pharmaceutically acceptable excipients and vehicles which per se are well known in the art. For topical application, the antagonist and/or inverse agonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

The antagonist and/or inverse agonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist and/or inverse agonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of the active compound per mililiter of formulation will constitute a therapeutically effective concentration for total application. If administered systemically, an amount between 0.01 and 5 mg per kg per day of body weight would be expected to effect a therapeutic result.

GENERAL EMBODIMENTS AND SYNTHETIC METHODOLOGY

Definitions

The term alkyl refers to and covers any and all groups which are known as normal alkyl, b ranched-chain alkyl, cycloalkyl and also cycloalkyl-alkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Unless specified otherwise, lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo- lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound failing within the definition of that term as classically used in organic chemistry. It includes organic and inorganic esters. Where B of Formula 1 is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$, is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

The term amides has the meaning classically accorded that term in organic chemistry. In this instance it includes the unsubstituted amides and all aliphatic and aromatic mono- and di- substituted amides. Unless stated otherwise in this application, preferred amides are the mono- and di-substituted amides derived from the saturated aliphatic radicals often or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted or unsubstituted phenyl or lower alkylphenyl amines. Unsubstituted amides are also preferred.

Acetals and ketals include the radicals of the formula-CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Some compounds of the present invention may have trans and cis (E and Z) isomers. Unless specific orientation of substituents relative to a double bond or a ring is indicated in the name of the respective compound, and/or by specifically showing in the structural formula the orientation of the substituents relative to the double bond or ring the invention covers trans as well as cis isomers.

Some of the compounds of the present invention may contain one or more chiral centers and therefore may exist in enantiomeric and diastereomeric forms. The scope of the present invention is intended to cover all isomers per se, .as well as mixtures of cis and trans isomers, mixtures of diastereomers and racemic mixtures of enantiomers (optical isomers) as well.

The compounds of the invention, can generally speaking be obtained by a series of reactions as disclosed in Reaction Scheme 1. Referring now to Reaction Scheme 1, the starting compound in this synthetic route is a dihydronaphthalene, chromen, thiochromen or dihdroquinoline of Formula 2 where the symbols X, R$_3$ and R$_4$ are defined as in connection with Formula 1, and where X$_1$ represents a leaving group, such as chloro, bromo or trifluoromethylsulfonyloxy (CF$_3$SO$_3$, triflate) group. Generally speaking the starting dihydronaphthalene compound is available in accordance with the chemical scientific or patent literature, or can be prepared by such modifications of published procedures which are readily within the skill of the practicing organic chemist. The ensuing detailed description provides the literature sources of or synthetic procedures for preparing certain examples of the starting compounds of Formula 2. Examples of chroman-4-one and thiochroman-4-one derivatives which can be readily converted into the chromen and thiochromen derivatives within the scope of Formula 2 or Formula 5 can be found in the patent or other chemical literature, for example in the publication Johnson et al.

Biorganic and Medicinal Chemistry 7 (1999) 1321–1338 (e. g. 6-methoxy-2,2-dimethyl-thiochroman-4-one; 2,2-dimethyl-4-oxo-thiochroman-6-yl trifluoromethanesulfonate; 2,2-dimethyl-6-bromo-thiochroman-4-one; 6-methoxy-2,2-dimethyl-chroman-4-one; 2,2-dimethyl-4-oxo-chroman-6-yl trifluoromethanesulfonate; 2,2-dimethyl-6-bromo-chroman-4-one; 6-methoxy-thiochroman-4-one; 4-oxo-thiochroman-6-yl trifluoromethanesulfonate; 6-bromo-thiochroman-4-one; 6-methoxy-chroman-4-one; 4-oxo-chroman-6-yl trifluoromethanesulfonate; 6-bromo-chroman-4-one).

Referring now to Reaction Scheme 1, the dihydronaphthalene, chromen or thiochromen derivative of Formula 2 is reacted with an aromatic or heteroaromatic amine of Formula 3, where the symbols Y, $R_2$, A and B are defined as in connection with Formula 1. Examples for the aryl or heteroaryl amines of Formula 3 are ethyl 4-aminobenzoate, ethyl 3-aminobenzoate, ethyl 6-aminopyridine-3-carboxylate, ethyl 6-aminopyridine-2-carboxylate, ethyl 5-aminothiophen-3-carboxylate, ethyl 5-aminothiophen-2-carboxylate, ethyl 5-aminofuran-3-carboxylate and ethyl 5-aminofuran-2-carboxylate. Generally speaking the aryl or heteroaryl amines of Formula 3 are available from the chemical literature, or can be made by such modifications of known processes which are readily apparent to the practicing synthetic organic chemist. The compound of Formula 2 is reacted with the aryl or heteroaryl amine of Formula 3 by heating, preferably in an aprotic solvent such as toluene and preferably in the presence of a catalysts, such as palladium(2) acetate ($Pd(OAc)_2$) and (S)—(—)—2,2'-bis(diphenylphosphino)1,1'-binaphthyl (BINAP) and an acid acceptor such as cesium carbonate ($CsCO_3$). The result of this type of reaction is a dihydronaphthalenyl, chromenyl or thichromenyl and aryl or heteroaryl substituted amine of Formula 4.

REACTION SCHEME 1

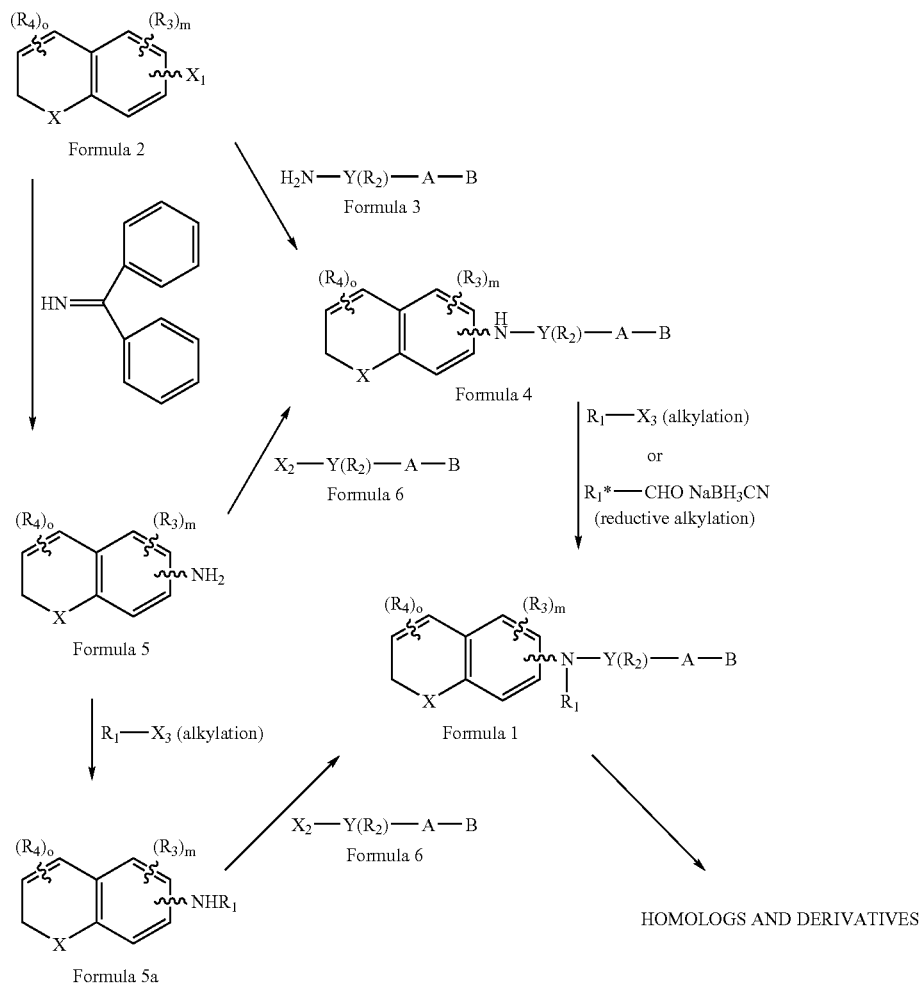

Still, as it is shown in Reaction Scheme 1, the secondary amine of Formula 4 can also be obtained by reacting a dihydronaphthalenyl, chromenyl or thiochromenyl amine of Formula 5 with a reagent of Formula 6 where $X_2$ represents a halogen, preferably iodine or bromine, and the remaining symbols are defined as in connection with Formula 1. The reagents of Formula 6 are halogen substituted aryl or heteroaryl compounds which, generally speaking, can be obtained by reactions well known in the art. An example of such a compound is ethyl 4-iodobenzoate which is obtainable, for example, by esterification of 4-iodobenzoic acid. This esterification reaction is described in U.S. Pat. No. 5,616,712 incorporated herein by reference. Other examples for the reagents of Formula 6 are ethyl 4-bromobenzoate, ethyl 6-iodonicotinate (obtainable by halogen exchange reaction on 6-chloronicotinic acid followed by esterification), ethyl 6-fluoronicotinate, ethyl 6-chloronicotinate, ethyl 5-iodo or 5-bromothiophene-2-carboxylate and ethyl 5-iodo or 5-bromofuran-2-carboxylate. The reaction of the amine of Formula 5 with the halogen substituted aryl or heteroaryl compound of Formula 6 is preferably conducted in the presence of the catalysts tris(dibenzylideneacetone)dipalladium(0) ($Pd_2(dba)_3$), and (S)—(—)-2,2'-bis(diphenylphosphino)1, 1'-binaphthyl (BINAP) in the presence of an acid acceptor, such as cesium carbonate, while being heated in an inert solvent (toluene) in an inert gas atmosphere.

The resulting aryl or heteroaryl, dihydronaphthalenyl amines (disubstituted amines) of Formula 4 are within the scope of the invention, but can be converted to the preferred trisubstituted amines of Formula 1, also within the scope of the invention, by reaction with a reagent of the formula

where $R_1$ is defined as in connection with Formula 1, and $X_3$ is halogen, preferably iodine or bromine. The reaction of the disubstituted amines of Formula 4 with the reagent

will be recognized by those skilled in the art as an "alkylation" or analogous reaction, and is preferably conducted by heating in an aprotic polar solvent, such as dimethylacetamide, in the presence of an acid acceptor, such as potassium carbonate. Alternatively, the secondary amines of Formula 4 are converted into the preferred tertiary amines of Formula 1 by a reductive alkylation reaction that employs the aldehyde reagent $R_1^*$—CHO, sodium cyanoborohydride and acetic acid usually in acetonitrile or tetrahydrofuran (THF) as the solvent. The group $R_1^*$—is defined to the extent it can be made applicable, as the group $R_1$ in Formula 1 with one less $CH_2$ unit, that is a homolog having one $CH_2$ unit (carbon atom) less than the group $R_1$.

The primary amine compounds of Formula 5 can be obtained from the compounds of Formula 2 by reactions known in the art, for example by reaction of the compounds of Formula 2 with benzophenone imine, as is shown in the reaction scheme.

Still another alternative route for the synthesis of the tertiary amines of Formula 1 is through alkylation of the compounds of Formula 5 with the reagent

(or reductive alkylation with the reagent R*—CHO) to yield the 17 dihydronapthalenyl, chromenyl or thiochromenyl alkyl amines of Formula 5a, which are thereafter reacted with the reagent of Formula 6.

The trisubstituted amine compounds of Formula 1 can be converted into further homologs and derivatives, still within the scope of the invention, by such reactions as esterification, saponification, homologation, reduction to aldehyde or alcohol stage and the like, which per se are well known in the art. These reactions usually involve transformations of the groups designated A and B in the formulas but are not necessarily limited to those. Some of the known and published general principles and synthetic methodology employed in the transformations of the A and B groups are briefly described below.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about –10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

SPECIFIC EMBODIMENTS

The preferred compounds of the invention are dihydronaphthalene derivatives $$(X=C(R)_2)$$

and R is preferably methyl. With reference to the symbol Y in Formula 1 the preferred compounds of the invention are those where Y is phenyl, naphthyl, pyridyl, thienyl or furyl. Even more preferred are compounds where Y is phenyl or pyridyl. As far as substitutions on the Y (phenyl) and Y (pyridyl) groups are concerned, compounds are preferred where the phenyl group is 1,4 (para) substituted and where the pyridine ring is 2,5 substituted. (Substitution in the 2,5 positions in the "pyridine" nomenclature corresponds to substitution in the 6-position in the "nicotinic acid" nomenclature.) In the presently preferred compounds of the invention there is no $R_2$ substituent (other than hydrogen) on the Y group. When there is an $R_2$ substituent it is preferably lower alkyl or halogen.

The A-B group of the preferred compounds is $(CH_2)_q COOH$ or $(CH_2)_q-COOR_8$, where $R_8$ is defined as above. Even more preferably q is zero and $R_8$ is lower alkyl or the compound is a carboxylic acid, or a pharmaceutically acceptable salt thereof.

$R_1$ is preferably an alkyl or allyl group, Among the alkyl groups methyl, ethyl, branched-chain alkyl and cyclopropylmethyl groups are preferred. In this regard it should be noted that in the definition of this invention the term alkyl includes cycloalkyl and cycloalkylalkyl groups as well.

The integer m is preferably 0 (zero) meaning that there is no $R_3$ substituent, or m=1 and in such case the $R_3$ substituent is preferably lower alkyl, or alkoxy even more preferably methyl, methoxy or ethoxy. The $R_3$ substituent is preferably in the 2 or 3 position of the dihydronaphthalene nucleus, as these positions arc indicated in Formula 7 below. The substituted amino groups are preferably in the otherwise unoccupied 2 or 3 position of the dihydronaphthalene nucleus, as these positions are indicated in Formula 7 below. Those skilled in the art will recognize that when the compounds of the invention and the intermediates leading thereto are given appropriate chemical names these positions may have a different number. However, the precise structures of the compounds of the invention are disclosed clearly with reference to the structural formulas provided below.

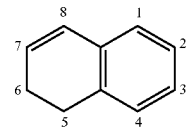

Formula 7

Referring now to the integer o in Formula 1, preferably o=1. In other words, the non-aromatic ring of the dihydronaphthalene moiety is preferably substituted with an $R_4$ group in the 8 position. It is also preferably substituted with geminal dimethyl groups in the 5 position (as indicated in Formula 7). A lower alkyl group for the 8 position, ($R_4$) is particularly preferred.

The most preferred compounds of the invention are disclosed in Table 2 with reference to Formulas 8 and 9.

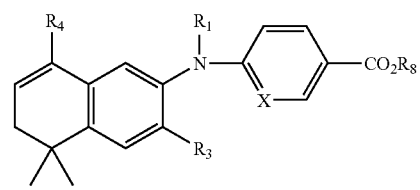

Formula 8

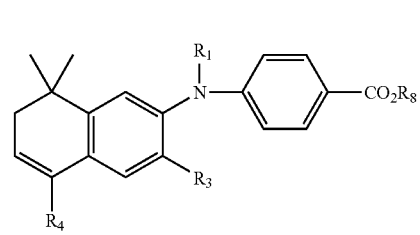

Formula 9

TABLE 2

| Compound No. | X  | Formula | $R_4$    | $R_3$  | $R_1$             | $R_8$ |
|--------------|----|---------|----------|--------|-------------------|-------|
| 84           | CH | 8       | t-butyl  | H      | H                 | ethyl |
| 85           | CH | 8       | t-butyl  | H      | ethyl             | ethyl |
| 88           | CH | 8       | t-butyl  | H      | ethyl             | H     |
| 86           | CH | 8       | t-butyl  | H      | n-propyl          | ethyl |
| 89           | CH | 8       | t-butyl  | H      | n-propyl          | H     |
| 87           | CH | 8       | t-butyl  | H      | allyl             | ethyl |
| 90           | CH | 8       | t-butyl  | H      | allyl             | H     |
| 65           | CH | 9       | methyl   | H      | H                 | ethyl |
| 66           | —  | 9       | methyl   | H      | methyl            | ethyl |
| 67           | —  | 9       | methyl   | H      | methyl            | H     |
| 42           | —  | 9       | methyl   | methyl | n-propyl          | ethyl |
| 46           | —  | 9       | methyl   | methyl | n-propyl          | H     |
| 48           | —  | 9       | i-propyl | methyl | H                 | ethyl |
| 49           | —  | 9       | i-propyl | methyl | methyl            | ethyl |
| 52           | —  | 9       | i-propyl | methyl | methyl            | H     |
| 50           | —  | 9       | i-propyl | methyl | ethyl             | ethyl |
| 53           | —  | 9       | i-propyl | methyl | ethyl             | H     |
| 39           | —  | 9       | methyl   | methyl | H                 | ethyl |
| 40           | —  | 9       | methyl   | methyl | methyl            | ethyl |
| 44           | —  | 9       | methyl   | methyl | methyl            | H     |
| 41           | —  | 9       | methyl   | methyl | ethyl             | ethyl |
| 45           | —  | 9       | methyl   | methyl | ethyl             | H     |
| 43           | —  | 9       | methyl   | methyl | cyclopropylmethyl | ethyl |

TABLE 2-continued

| Compound No. | X | Formula | R₄ | R₃ | R₁ | R₈ |
|---|---|---|---|---|---|---|
| 47 | — | 9 | methyl | methyl | cyclopropylmethyl | H |
| 51 | — | 9 | i-propyl | methyl | n-propyl | ethyl |
| 54 | — | 9 | i-propyl | methyl | n-propyl | H |
| 55 | — | 9 | ethyl | methyl | H | ethyl |
| 57 | — | 9 | ethyl | methyl | ethyl | ethyl |
| 59 | — | 9 | ethyl | methyl | ethyl | H |
| 56 | — | 9 | t-butyl | methyl | H | ethyl |
| 58 | — | 9 | t-butyl | methyl | ethyl | ethyl |
| 60 | — | 9 | t-butyl | methyl | ethyl | H |
| 15 | CH | 8 | methyl | methyl | H | ethyl |
| 19 | CH | 8 | methyl | methyl | ethyl | ethyl |
| 23 | CH | 8 | methyl | methyl | ethyl | H |
| 17 | CH | 8 | i-propyl | methyl | H | ethyl |
| 21 | CH | 8 | i-propyl | methyl | ethyl | ethyl |
| 25 | CH | 8 | i-propyl | methyl | ethyl | H |
| 18 | CH | 8 | t-butyl | methyl | H | ethyl |
| 22 | CH | 8 | t-butyl | methyl | ethyl | ethyl |
| 26 | CH | 8 | t-butyl | methyl | ethyl | H |
| 73 | — | 9 | ethyl | H | H | ethyl |
| 74 | — | 9 | ethyl | H | ethyl | ethyl |
| 75 | — | 9 | ethyl | H | ethyl | H |
| 16 | CH | 8 | ethyl | methyl | H | ethyl |
| 20 | CH | 8 | ethyl | methyl | ethyl | ethyl |
| 24 | CH | 8 | ethyl | methyl | ethyl | H |
| 68 | — | 9 | methyl | H | ethyl | ethyl |
| 69 | — | 9 | methyl | H | ethyl | H |
| 80 | — | 9 | i-propyl | H | ethyl | ethyl |
| 81 | | 9 | i-propyl | H | ethyl | H |
| 79 | — | 9 | i-propyl | H | H | ethyl |
| 125 | CH | 8 | Me | n-hexyloxy | ethyl | Et |
| 142 | CH | 8 | Me | n-hexyloxy | ethyl | H |
| 126 | CH | 8 | Me | n-heptyloxy | ethyl | Et |
| 143 | CH | 8 | Me | n-heptyloxy | ethyl | H |
| 127 | CH | 8 | Me | benzyloxy | ethyl | Et |
| 144 | CH | 8 | Me | benzyloxy | ethyl | H |
| 128 | CH | 8 | Me | n-hexyloxy | n-propyl | Et |
| 145 | CH | 8 | Me | n-hexyloxy | n-propyl | H |
| 129 | CH | 8 | Me | n-heptyloxy | n-propyl | Et |
| 146 | CH | 8 | Me | n-heptyloxy | n-propyl | H |
| 130 | CH | 8 | Me | benzyloxy | n-propyl | Et |
| 147 | CH | 8 | Me | benzyloxy | n-propyl | H |
| 131 | CH | 8 | i-propyl | methoxy | ethyl | Et |
| 148 | CH | 8 | i-propyl | methoxy | ethyl | H |
| 132 | CH | 8 | i-propyl | ethoxy | ethyl | Et |
| 149 | CH | 8 | i-propyl | ethoxy | ethyl | H |
| 133 | CH | 8 | i-propyl | n-propyloxy | ethyl | Et |
| 150 | CH | 8 | i-propyl | n-propyloxy | ethyl | H |
| 134 | CH | 8 | i-propyl | i-propyloxy | ethyl | Et |
| 151 | CH | 8 | i-propyl | i-propyloxy | ethyl | H |
| 135 | CH | 8 | i-propyl | n-butyloxy | ethyl | Et |
| 152 | CH | 8 | i-propyl | n-butyloxy | ethyl | H |
| 136 | CH | 8 | i-propyl | n-hexyloxy | ethyl | Et |
| 153 | CH | 8 | i-propyl | n-hexyloxy | ethyl | H |
| 137 | CH | 8 | i-propyl | benzyloxy | ethyl | Et |
| 154 | CH | 8 | i-propyl | benzyloxy | ethyl | H |
| 138 | CH | 8 | i-propyl | 4-methylbenzyloxy | ethyl | Et |
| 155 | CH | 8 | i-propyl | 4-methylbenzyloxy | ethyl | H |
| 139 | CH | 8 | i-propyl | 3,5-di-t-butylbenzyloxy | ethyl | Et |
| 156 | CH | 8 | i-propyl | 3,5-d-t-butylbenzyloxy | ethyl | H |
| 140 | CH | 8 | i-propyl | benzyloxy | n-propyl | Et |
| 157 | CH | 8 | i-propyl | benzyloxy | n-propyl | H |
| 141 | CH | 8 | t-butyl | benzyloxy | ethyl | Et |
| 158 | CH | 8 | t-butyl | benzyloxy | ethyl | H |
| 170 | N | 8 | methyl | H | ethyl | H |
| 171 | N | 8 | ethyl | H | ethyl | H |
| 172 | N CH | 8 | i-propyl | H | ethyl | H |
| 173 | N CH | 8 | t-butyl | H | ethyl | H |

REACTION SCHEME 2

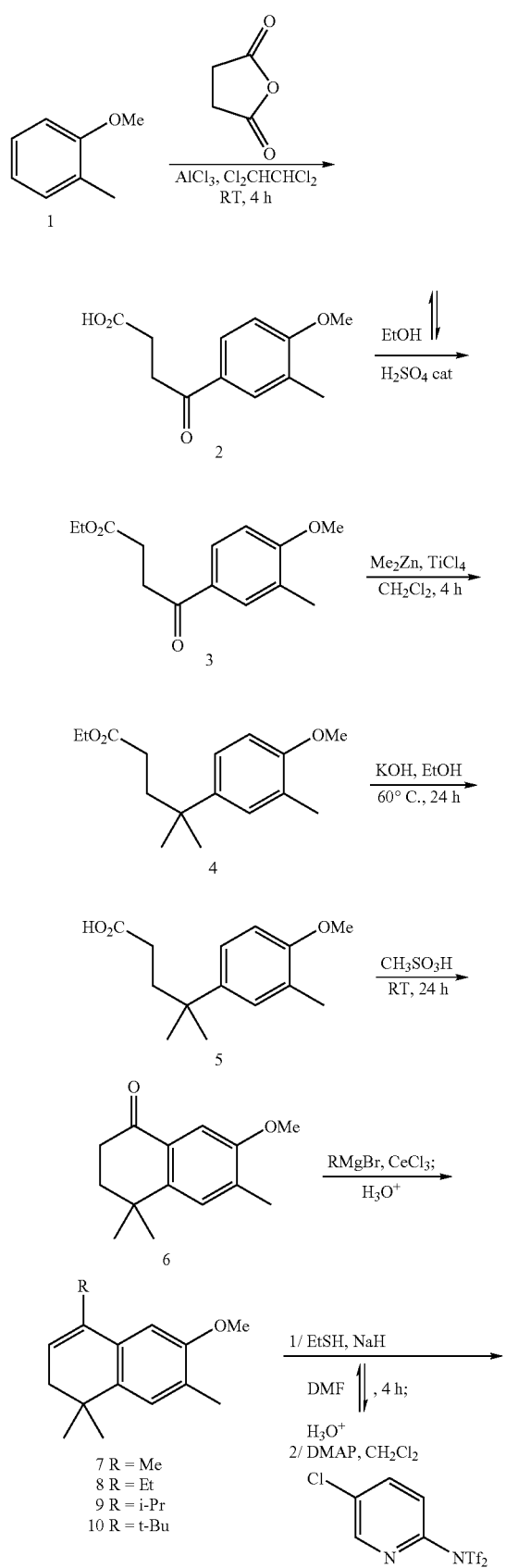
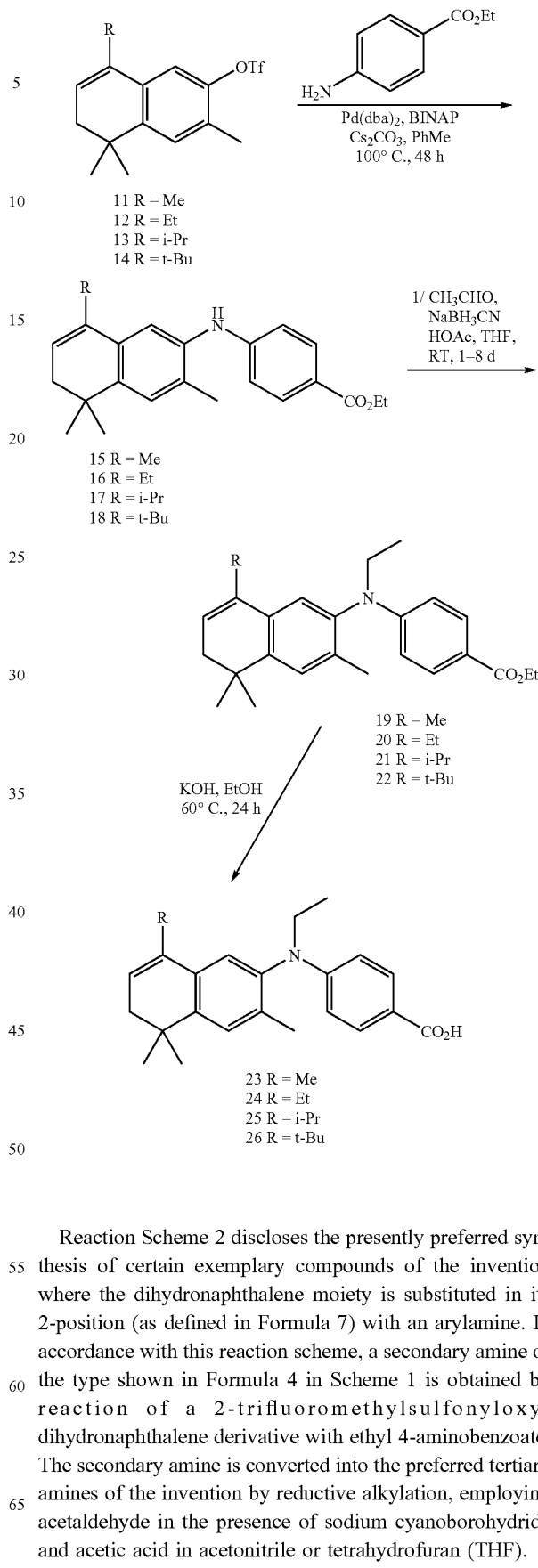

Reaction Scheme 2 discloses the presently preferred synthesis of certain exemplary compounds of the invention where the dihydronaphthalene moiety is substituted in its 2-position (as defined in Formula 7) with an arylamine. In accordance with this reaction scheme, a secondary amine of the type shown in Formula 4 in Scheme 1 is obtained by reaction of a 2-trifluoromethylsulfonyloxy-dihydronaphthalene derivative with ethyl 4-aminobenzoate. The secondary amine is converted into the preferred tertiary amines of the invention by reductive alkylation, employing acetaldehyde in the presence of sodium cyanoborohydride and acetic acid in acetonitrile or tetrahydrofuran (THF).

Reaction Scheme 3 discloses another example of a synthetic route leading to certain preferred compounds of the invention where the dihydronaphthalene moiety is substituted in its 2- and 8- positions with a methyl group and in the 3-position with an arylamine. In this exemplary synthetic route also, the secondary amines of the type of Formula 4 in Scheme 1 are obtained by reaction of the corresponding trifluoromethylsulfonyloxy-dihydronaphthalene derivatives, (3-trifluoromethylsulfonyloxy-dihydronaphthalene derivatives) with ethyl 4-aminobenzoate. The secondary amine is converted into the exemplary preferred tertiary amines of the invention by reductive alkylation, employing formaldehyde, acetaldehyde, propionaldehyde and cyclopropylformaldehyde, respectively. Reaction Scheme 4 discloses the synthesis of examples analogous to those shown in Scheme 3, however in Scheme 4 the dihydronaphthalene moiety is substituted with a methyl group in its 2-position and respectively with iso-propyl, ethyl and tertiary-butyl groups on its 8-position. In this scheme also, the secondary amines are obtained by displacement of 3-trifluoromethylsulfonyloxy-dihydronaphthalene derivatives with ethyl 4-aminobenzoate and the secondary amines are converted into the exemplary preferred tertiary amines of the invention by reductive alkylation.

REACTION SCHEME 3

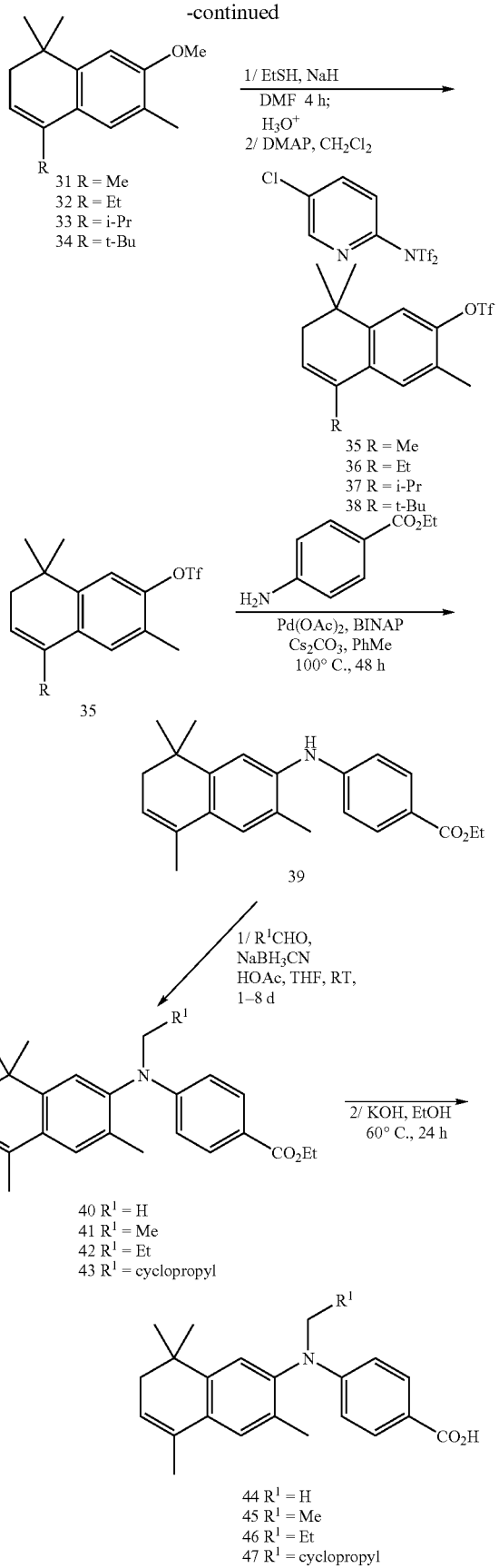

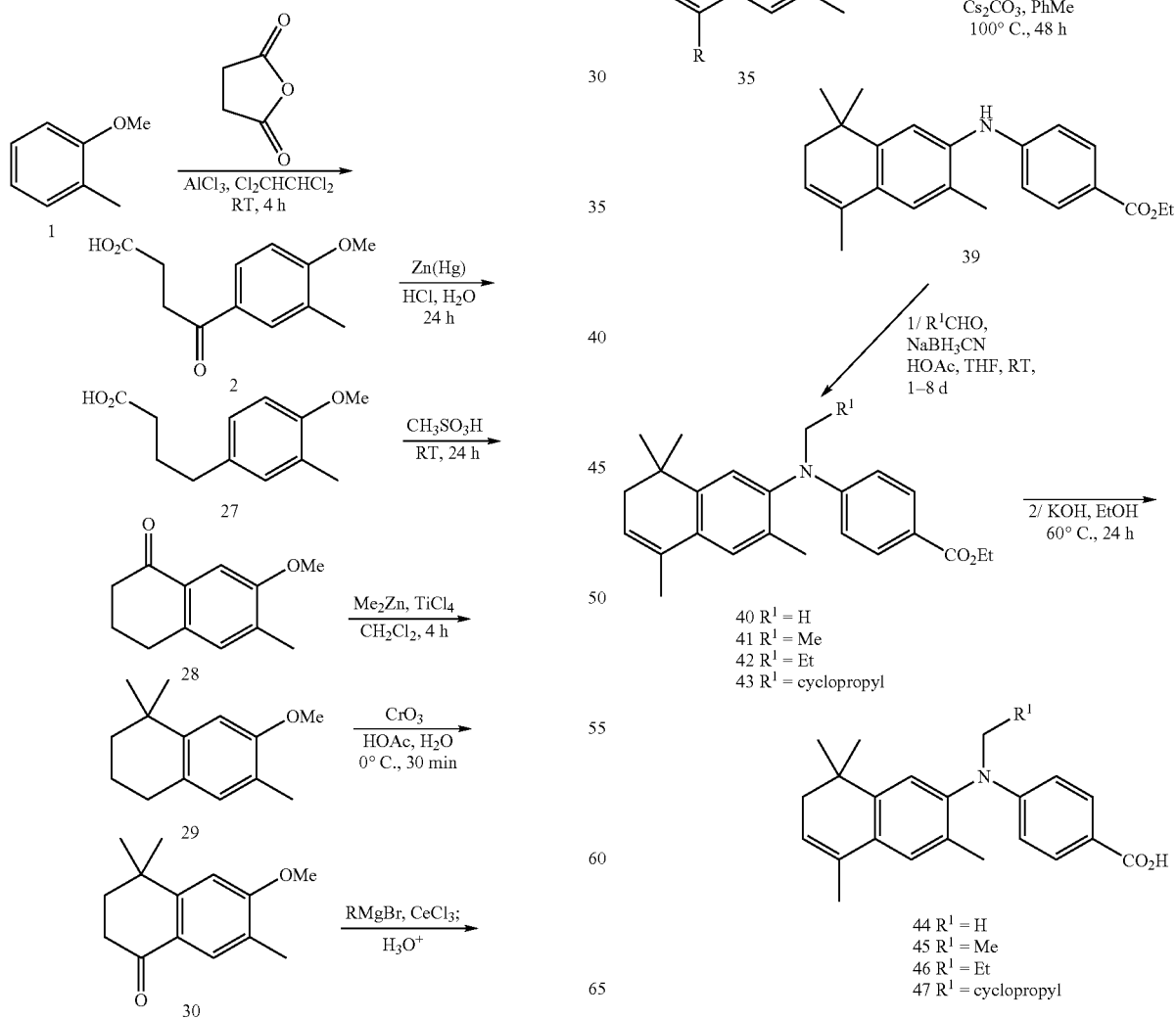

REACTION SCHEME 4

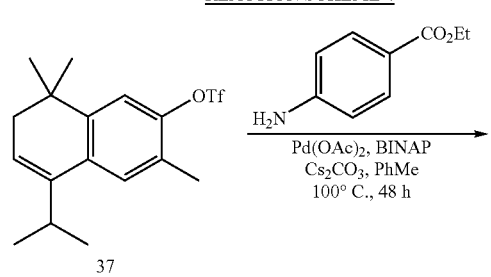

37

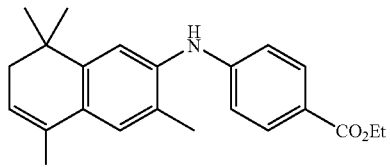

55 R = Et
56 R = t-butyl

1/ CH₃CHO, NaBH₃CN
HOAc, THF, RT, 1–8 d

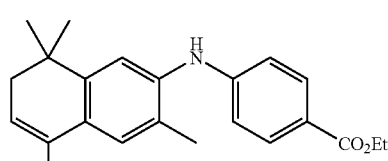

48

1/ R¹CHO, NaBH₃CN
HOAc, THF, RT, 1–8 d

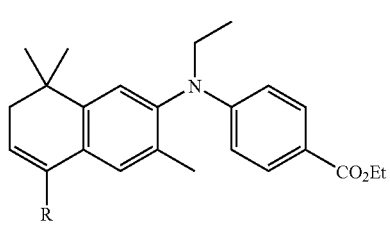

57 R = Et
58 R = t-butyl

2/ KOH, EtOH
60° C., 24 h

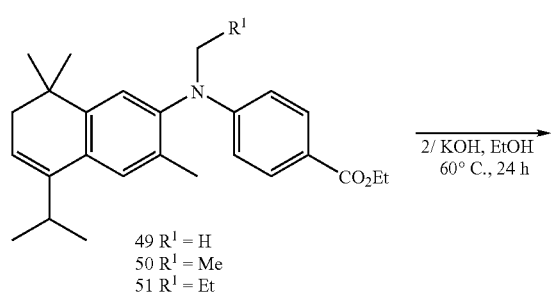

49 R¹ = H
50 R¹ = Me
51 R¹ = Et

2/ KOH, EtOH
60° C., 24 h

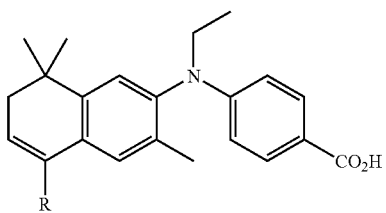

59 R = Et
60 R = t-butyl

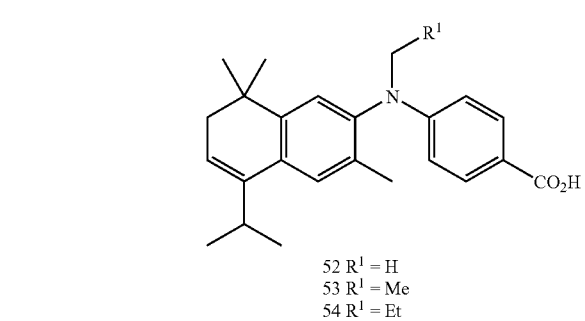

52 R¹ = H
53 R¹ = Me
54 R¹ = Et

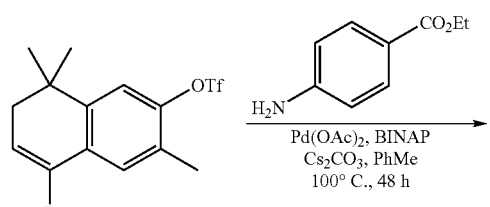

36 R = Et
38 R = t-butyl

Reaction Scheme 5 discloses presently preferred synthetic routes for making certain preferred compounds of the invention where the dihydronaphthalene moiety is substituted in its 3-position with an arylamine and where the 2-position is unsubstituted. In these examples of synthesis the starting compound is 6-bromo-4,4-dimethyl-1,2,3,4-tetrahydronaphthalene-1—one which is available in accordance with U.S. Pat. No. 5,489,584, the specification of which is expressly incorporated herein by reference. After an alkyl substituent is introduced into the dihydronaphthalene nucleus by subjecting the carbonyl carbon to a Grignard (or like) reaction, the bromo atom is replaced with an $NH_2$ group by reaction with benzophenoneimine in the presence of the catalysts tris(dibenzylideneacetone)dipalladium(0) ($Pd_2(dba)_3$), (S)—(—)-2,2'-bis(diphenylphosphino)1,1'-binaphthyl (BINAP) and sodium tertiary-butoxide. The preferred tertiary amines of the invention are also obtained in this scheme by reductive alkylation.

Reaction Scheme 5
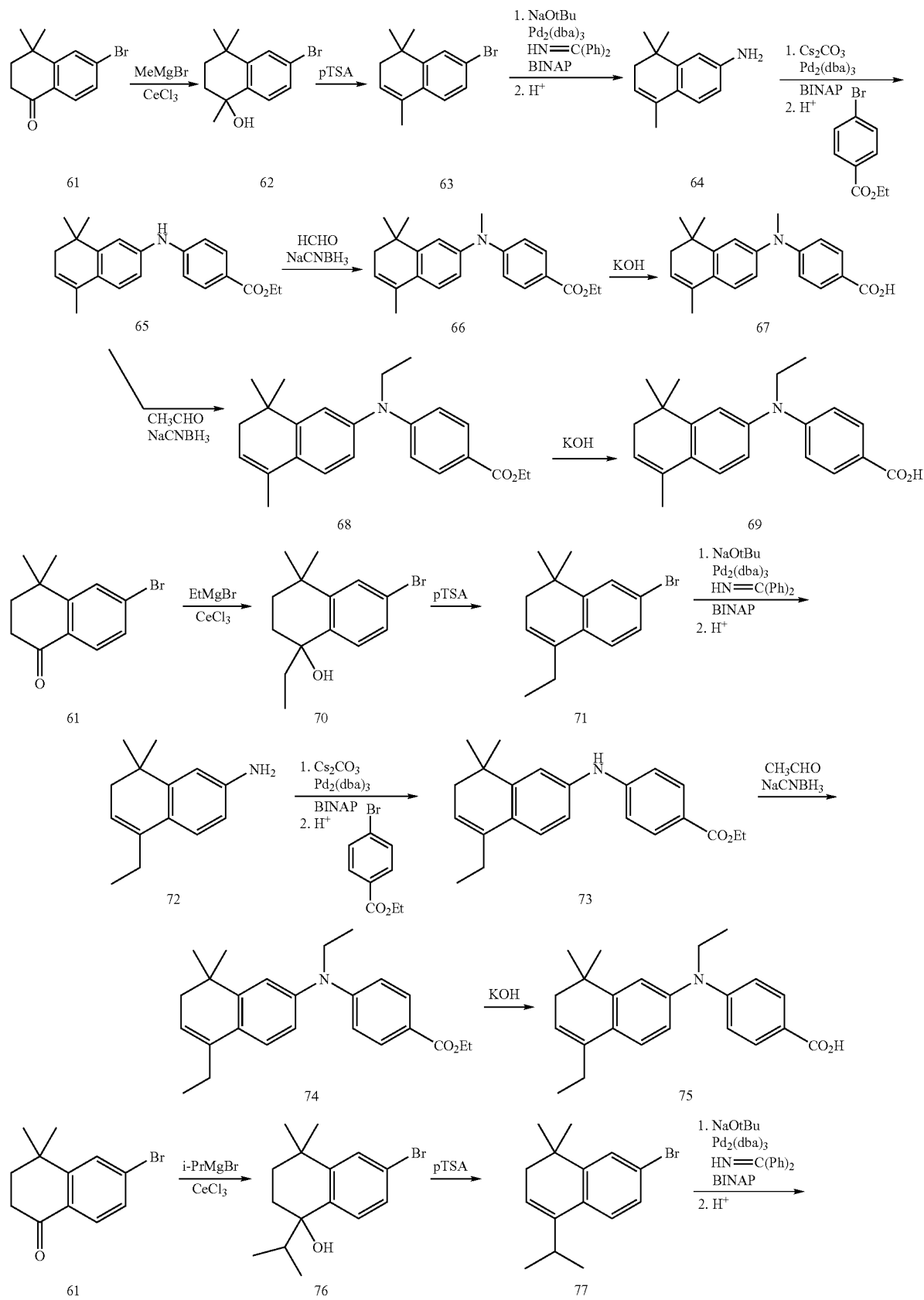

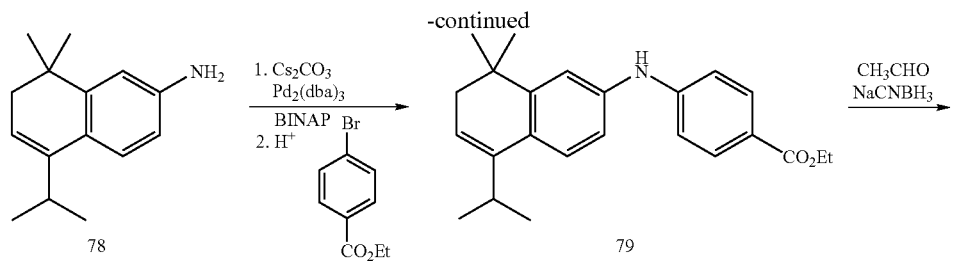

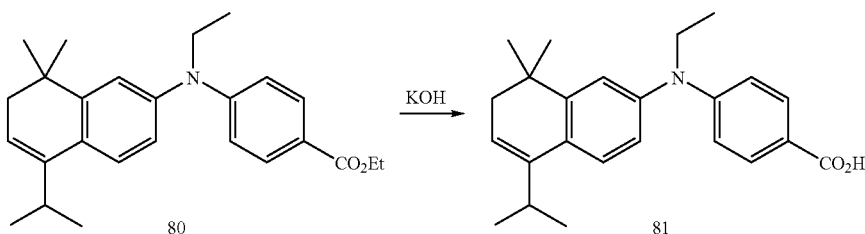

Reaction Scheme 6 provides an exemplary synthetic route for preparing preferred compounds of the invention where the dihydronaphthalene moiety is substituted with a tertiary-butyl group in its 8-position and with an arylamine in its 2-position. In this synthetic process the starting compound is 7-bromo-1-(1,1-dimethylethyl)-3,4-dihydro-4,4-dimethylnaphthalene which is available in accordance with the U.S. Pat. No. 5,763,635, the specification of which is incorporated herein by reference. This starting compound is converted into the corresponding amino derivative by reaction with benzophenoneimine, as is described above in connection with Reaction Scheme 5. The amino substituted dihydronaphthalene is thereafter reacted with ethyl 4-iodobenzoate in the presence of the catalysts tris(dibenzylideneacetone)dipalladium(0) (Pd$_2$(dba)$_3$), (S)—(—)-2,2'-bis(diphenylphosphino)1,1'-binaphthyl (BINAP) and cesium carbonate. The resulting secondary amines are converted into the preferred tertiary amines of the invention by alkylation with ethyl iodide, n-propyliodide and allyl bromide, respectively.

Reaction Scheme 7 provides an exemplary synthetic route for preparing preferred compounds of the invention where the dihydronaphthalene moiety is substituted with methyl, ethyl, iso-propyl and tertiary-butyl groups, respectively, in its 8-position, with an arylamine in its 2-position and with an O-alkyl group in its 3 position. The starting compound for this synthetic route is methoxyphenol (anisol). The coupling reaction of a 2-bromo-dihydronaphthalene derivative with ethyl 4-aminobenzoate is conducted in the presence of the catalysts tris(dibenzylideneacetone)dipalladium(0) (Pd$_2$(dba)$_3$) and 2-dicyclohexylphosphino-2'-(N,N-dimethylamino)biphenyl (Cy—MAP) which is commercially available from Strem Chemicals Inc. Newburtyport Mass. (see also J. Am. Chem. Soc., 1998, 120, 9722 and J. Am. Chem. Soc., 1999, 121, 6090.)

Reaction Scheme 8 provides an exemplary synthetic route for preparing preferred compounds of the invention where the dihydronaphthalene moiety is substituted with methyl, ethyl, iso-propyl and tertiary-butyl groups, respectively, in its 8-position, and with a 6-amino-pyridine-3-carboxylic acid residue in the 2 position. The starting compounds for these syntheses are the 2-bromo-8-methyl-,.2-bromo-8-ethyl-, 2-bromo-8-i-propyl-, and 2-bromo-8-t-butyl-5,6-dihydronaphtalenes which are available in accordance with the state of the art. The tertiary-butyl compound is described for example in U.S. Pat. No. 5,763,635, incorporated herein by reference. The 2-bromo-8-methyl-, 2-bromo-8-ethyl-, 2-bromo-8-i-propyl-, and 2-bromo-8-t-butyl-5,6-dihydronaphtalenes, respectively, are converted to the 2-amino derivatives by reaction with benzophenone-imine, and this is followed by acetylation of the primary amino group to provide the corresponding acetamides. The acetamides are reduced with LiAlH$_4$ to give the corresponding 2-dihydronaphtalenyl-ethyl amides, and these are reacted with 6-fluoro-pyridine-3-carboxylic acid by heating in an aprotic solvent, such as toluene, to provide exemplary preferred compounds of the invention which are nicotinic acid derivatives.

Detailed description of the steps of the processes illustrated in Reaction Schemes 2–8 are provided below in the experimental section.

REACTION SCHEME 6

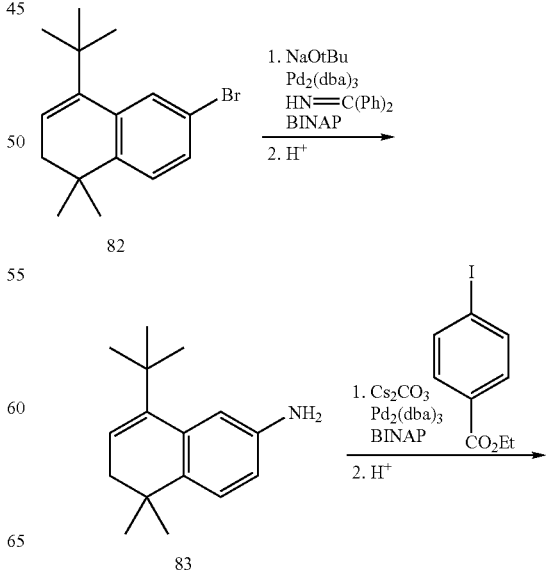

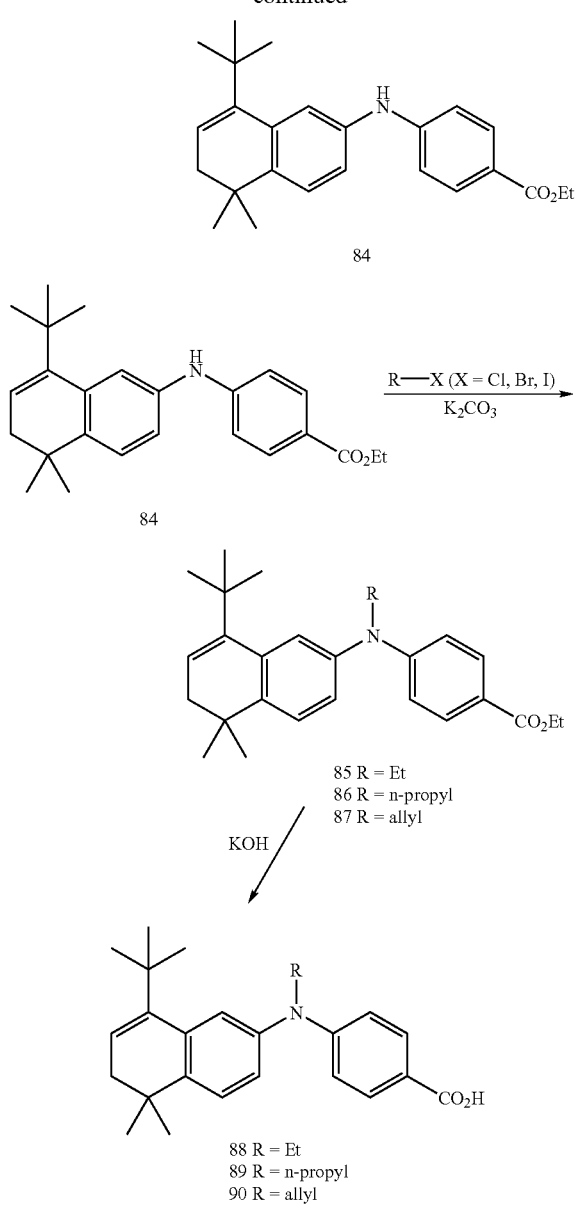
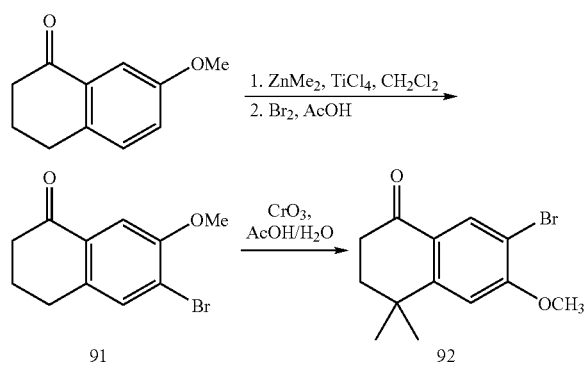
Reaction Scheme 7
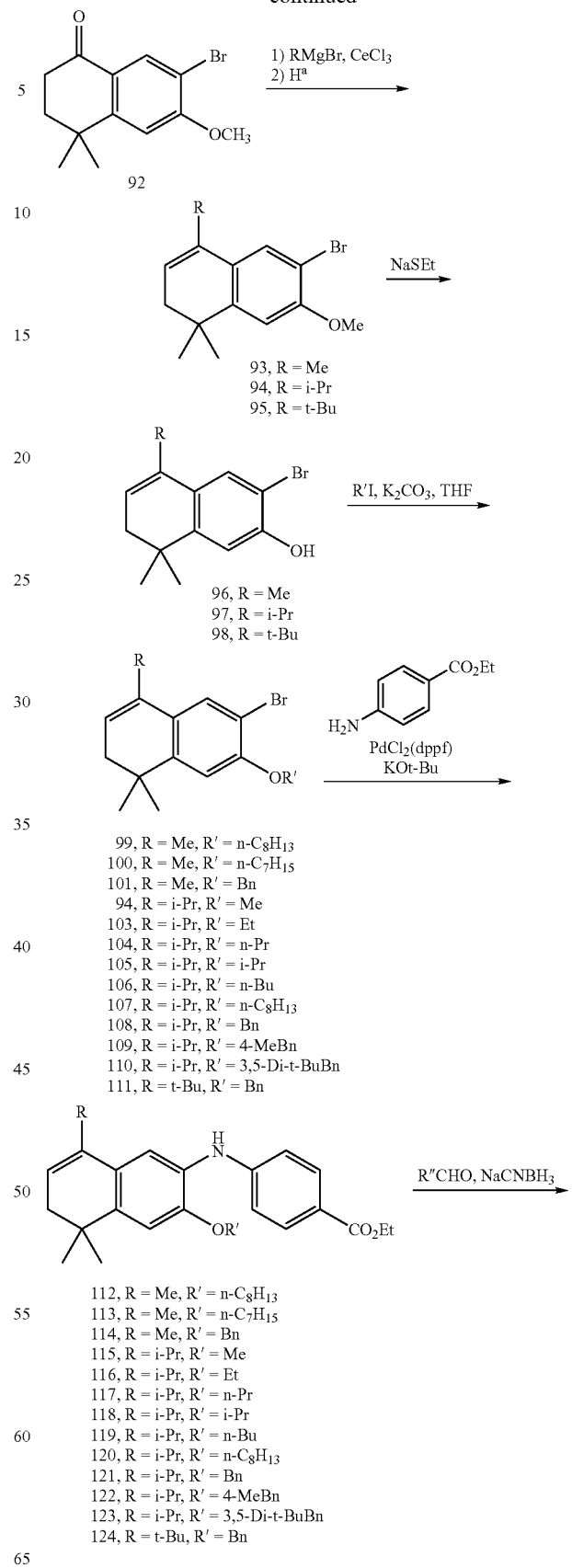

33
-continued

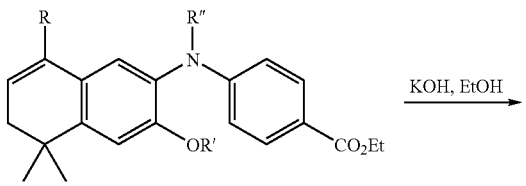

125, R = Me, R' = n-C$_8$H$_{13}$, R'' = Et
126, R = Me, R' = n-C$_7$H$_{15}$, R'' = Et
127, R = Me, R' = Bn, R'' = Et
128, R = Me, R' = n-C$_8$H$_{13}$, R'' = n-Pr
129, R = Me, R' = n-C$_7$H$_{15}$, R'' = n-Pr
130, R = Me, R' = Bn, R'' = n-Pr
131, R = i-Pr, R' = Me, R'' = Et
132, R = i-Pr, R' = Et, R'' = Et
133, R = i-Pr, R' = n-Pr, R'' = Et
134, R = i-Pr, R' = i-Pr, R'' = Et
135, R = i-Pr, R' = n-Bu, R'' = Et
136, R = i-Pr, R' = n-C$_8$H$_{13}$, R'' = Et
137, R = i-Pr, R' = Bn, R'' = Et
138, R = i-Pr, R' = 4-MeBn, R'' = Et
139, R = i-Pr, R' = 3,5-Di-t-BuBn, R'' = Et
140, R = i-Pr, R' = Bn, R'' = n-Pr
141, R = t-Bu, R' = Bn, R'' = Et

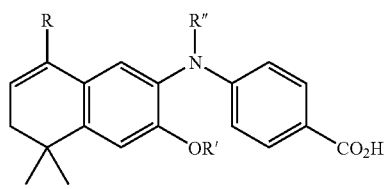

142, R = Me, R' = n-C$_8$H$_{13}$, R'' = Et
143, R = Me, R' = n-C$_7$H$_{15}$, R'' = Et
144, R = Me, R' = Bn, R'' = Et
145, R = Me, R' = n-C$_8$H$_{13}$, R'' = n-Pr
146, R = Me, R' = n-C$_7$H$_{15}$, R'' = n-Pr
147, R = Me, R' = Bn, R'' = n-Pr
148, R = i-Pr, R' = Me, R'' = Et
149, R = i-Pr, R' = Et, R'' = Et
150, R = i-Pr, R' = n-Pr, R'' = Et
151, R = i-Pr, R' = i-Pr, R'' = Et
152, R = i-Pr, R' = n-Bu, R'' = Et
153, R = i-Pr, R' = n-C$_8$H$_{13}$, R'' = Et
154, R = i-Pr, R' = Bn, R'' = Et
155, R = i-Pr, R' = 4-MeBn, R'' = Et
156, R = i-Pr, R' = 3,5-Di-t-BuBn, R'' = Et
157, R = i-Pr, R' = Bn, R'' = n-Pr
158, R = t-Bu, R' = Bn, R'' = Et

REACTION SCHEME 8

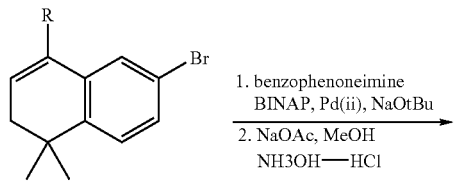

82
R = Me
R = Et
R = iPr
R = tBu

34
-continued

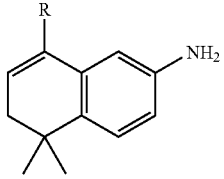

159 R = Me
160 R = Et
161 R = iPr
83 R = tBu

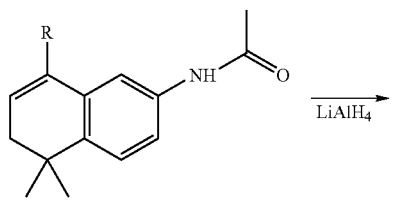

162 R = Me
163 R = Et
164 R = iPr
165 R = tBu

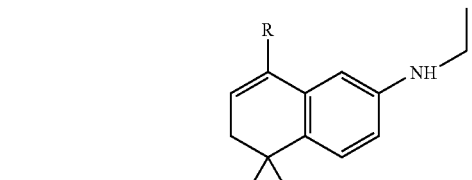

166 R = Me
167 R = Et
168 R = iPr
169 R = tBu

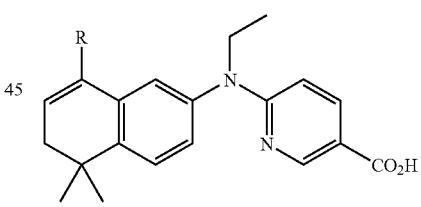

170 R = Me
171 R = Et
172 R = iPr
173 R = tBu

SPECIFIC EXAMPLES
4-(4-Methoxy-3-methylphenyl)-4-oxobutyric acid (Compound 2)

To a solution of succinic anhydride (12.0 g, 122.0 mmol) and 50 mL of 1,1,2,2,-tetrachloroethane at room temperature was added AlCl$_3$ (21.5 g, 161.2 mmol) and 2-methylanisole (Compound 1, 10 mL, 81.0 mmol). The resulting solution was stirred for 4 h at room temperature, then poured into a solution of concentrated HCl (20 mL) in water (50 mL) and ice. Dichloromethane was added, and the bottom layer was separated. The solvents were removed under reduced pressure, and the residue was dissolved in a boiling solution of sodium carbonate (30 g $Na_2CO_3$ in 160 mL $H_2O$) for 10 min, and filtered. The filtrate was acidified with concentrated HCl to pH=0–1, and crystallized in a salt ice bath. The solid product was filtered and washed with cold water, and dried in the air to give 13.7 g (76%) of the title compound as an off-white solid.

PNMR (300 MHz, $CDCl_3$) δ 2.25 (s, 3 H), 2.82 (t, 2 H, J=7.5 Hz), 3.28 (t, 2 H, J=7.5 Hz), 3.89 (s, 3 H), 6.86 (d, 1 H, J=8.0 Hz), 7.78 (s, 1 H), 7.87 (d, 1 H, J=8.0 Hz).

4-(4-Methoxy-3-methylphenyl)-4-oxo-butyric acid ethyl ester (Compound 3)

To a solution of 4-(4-methoxy-3-methylphenyl)-4-oxobutyric acid (Compound 2, 21.75 g, 98.0 mmol) in absolute ethanol (200 mL) was added 10 drops of concentrated $H_2SO_4$. The resulting solution was refluxed for 3 days, then cooled to room temperature, treated with 30 mL of NaOH 2 N, diluted with 50 mL of water, and extracted 3 times with EtOAc. The combined organic layers were washed with brine, and dried over $MgSO_4$, and filtered. The solvent was removed to afford 20.6 g (84%) of the title compound as a yellow solid.

PNMR (300 MHz, $CDCl_3$) δ 1.24 (t, 3 H, J=6.7 Hz), 2.24 (s, 3 H), 2.73 (t, 2 H, J=6.67 Hz), 3.26 (t, 2 H, J=6.7 Hz), 3.90 (s, 3 H), 4.14 (t, 2 H, J=7.0 Hz), 6.84 (d, 1 H, J=8.6 Hz), 7.79 (s, 1 H), 7.85 (d, 1 H, J=8.5 Hz).

4-(4-Methoxy-3-methylphenyl)-4-methyl-pentanoic acid ethyl ester (Compound 4)

To a solution of $TiCl_4$ 1 M in $CH_2Cl_2$ (50 mL, 50 mmol) at −40° C. under the argon atmosphere was added a solution of $Me_2Zn$ 2 M in toluene (43 mL, 85 mmol), and the resulting dark brown cloudy mixture was stirred for 15 min. A solution of 4-(4-methoxy-3-methylphenyl)-4-oxo-butyric acid ethyl ester (Compound 3, 7.1 g, 28.4 mmol) and 20 mL of dichloromethane was then added, and the temperature was raised to 0° C., then to room temperature. After 4 h, the reaction was cooled to 0° C., quenched with methanol until no more bubbling was observed. Saturated $NH_4Cl$ was added, and the reaction mixture was extracted three times with dichloromethane, washed with $NaHCO_3$ 1 N, brine, and dried over $MgSO_4$, and filtered. The solvent was removed to give 6.8 g (91%) of the title compound as an amber oil.

PNMR (300 MHz, $CDCl_3$) δ 1.25 (t, 3 H, J=7.1 Hz), 1.30 (s, 6 H),. 1.96 (m, 2 H), 2.08 (m, 2 H), 2.22 (s, 3 H), 3.83 (s, 3 H), 4.06 (q, 2 H, J=7.1 Hz), 6.75 (d, 1 H, J=12.5 Hz), 7.09 (s, 2 H).

4-(4-Methoxy-3-methylphenyl)-4-methyl-pentanoic acid (Compound 5)

To a solution of 4-(4-methoxy-3-methylphenyl)-4-methyl-pentanoic acid ethyl ester (Compound 4, 6.8 g, 25.8 mmol) and 20 mL of absolute ethyl alcohol was added aqueous 5 M KOH (6 mL). The resulting solution was heated in an 60° C. bath for 24 h. The solution was cooled to room temperature, diluted with water and washed once with 2:1 hexane:ethyl acetate solution, and the layers were separated. The aqueous layer was acidified with HCl 2 N to pH=0–1 and the product extracted three times with ethyl acetate. The combined organic extracts were washed with brine, and dried over $MgSO_4$, and filtered. The solvent was removed to give 5.9 g (97%) of the title compound as a dark oil.

PNMR (300 MHz, $CDCl_3$) δ 1.30 (s, 6 H), 1.96 (m, 2 H), 2.10 (m, 2 H), 2.22 (s, 3 H), 3.80 (s, 3 H), 6.76 (d, 1 H, J=12.5 Hz), 7.09 (s, 2 H). ps 7-Methoxy-4,4,6-trimethyl-3,4-dihydro-2H-naphthalen-1-one (Compound 6)

A solution of 4-(4-methoxy-3-methylphenyl)-4-methyl-pentanoic acid (Compound 5, 7.8 g, 33 mmol) and 150 mL of methanesulfonic acid was stirred at room temperature under an argon atmosphere for 24 h, then poured into ice, extracted three times with ethyl acetate, washed with $NaHCO_3$ 1 N, brine, and dried over $MgSO_4$, and filtered. The solvent was removed, and the residue was purified by flash chromatography (Hexane:Ethyl Acetate=4:1) to afford 3.9 g (54%) of the title compound as a yellow solid.

PNMR (300 MHz, $CDCl_3$) δ 1.32 (s, 6 H), 1.94 (t, 2 H, J=7.5 Hz), 2.22 (s, 3 H), 2.68 (t, 2 H, J=7.5 Hz), 3.82 (s, 3 H), 7.14 (s, 1 H), 7.41 (s, 1 H).

6-Methoxy- 1,1,4,7-tetramethyl- 1,2-dihydro-naphthalene (Compound 7)

General Procedure A $CeCl_3$ 7 $H_2O$ (1.28 g, 3.4 mmol) was heated in an oil bath to 140–150° C. under high vacuum without stirring for 2 h, and then with stirring for 2 h. Argon was then introduced, and the flask was cooled to room temperature. Tetrahydrofuran (10 mL) was added, and the resulting slurry solution was stirred at room temperature under the argon atmosphere for 3 h. A solution of 7-methoxy-4,4,6-trimethyl-3,4-dihydro-2H-naphthalen-1-one (Compound 6, 0.53 g, 2.3 mmol) and 5 mL of tetrahydrofuran was added, and the reaction mixture was stirred for 1 h, then cooled to 0° C. A solution of 3 M MeMgBr in diethyl ether (1.2 mL, 3.4 mmol) was added, and the ice bath was removed. After 1 h, the reaction was poured into concentrated sulfuric acid in ice, extracted with ethyl acetate, washed with IN $NaHCO_3$, brine, dried over $MgSO_4$, and filtered. The solvent was removed to give 0.42 g (80%) of the title compound as an orange oil.

PNMR (300 MHz, $CDCl_3$) δ 1.23 (s, 6 H), 2.07 (s, 3 H), 2.10 (d, 2 H, J=4.0 Hz) 2.23 (s, 3 H) 3.85 (s, 3 H) 5.73 (s, 1 H), 6.75 (s, 1 H), 7.08 (s, 1 H).

4-Ethyl-6-methoxy- 1,1,7-trimethyl-1,2-dihydro-naphthalene (Compound 8)

Following General Procedure A, 7-methoxy-4,4,6-trimethyl-3,4-dihydro-2H-naphthalen-1-one (Compound 6, 0.5 g, 2.3 mmol) was reacted with a solution of 3 M EtMgBr (2.3 mL, 6.9 mmol), and the crude product was purified by flash chromatography (hexane:ethyl acetate=4:1) to give 0.33 g (63%) of the title compound as a clear oil. PNMR (300 MHz, $CDCl_3$) δ 1.32 (t,3 H, J=6.3 Hz), 1.38 (s, 6 H), 2.32 (d, 2 H, J=4.5 Hz), 2.42 (s, 3 H), 2.65 (m, 2 H), 3.98 (s, 3 H), 5.88 (t, 1 H, J=2.5 Hz), 6.96 (s, 1 H), 7.28 (s, 1 H).

4-Isopropyl-6-methoxy- 1,1,7-trimethyl-1,2-dihydronaphthalene (Compound 9)

Following General Procedure A, 7-methoxy4,4,6-trimethyl-3,4-dihydro-2H-naphthalen-1-one (Compound 6, 1.0 g, 4.6 mmol) was reacted with a solution of 2 M isopropylmagnesium chloride (12 mL, 22.9 mmol) to give 1.1 g (100%) of the title product as a yellow oil.

PNMR (300 MHz, $CDCl_3$) δ 1.43 (s, 6 H), 1.45 (d, 6 H, J=3.4 Hz), 2.38 (d, 2 H, J=4.6 Hz), 2.45 (s, 3 H), 3.20 (m, 1 H), 4.05 (s, 3 H), 5.97 (t, 1 H, J=4.4 Hz), 7.09 (s, 1 H), 7.34 (s, 1 H).

4-tert-Butyl-6-methoxy-1,1,7-trimethyl-1,2,-dihydronaphthalene (Compound 10)

Following General Procedure A, 7-methoxy-4,4,6-trimethyl-3,4-dihydro-2H-naphthalen-1-one (Compound 6, 1.5 g, 6.9 mmol) was reacted with a solution of 2 M tert-butylmagnesium chloride (12 mL, 23 mmol), and the crude product was purified by flash column (hexane:ethyl acetate=4:1) to give 0.63 g (36%) of the title product as a clear oil.

PNMR (300 MHz, $CDCl_3$,) δ 1.48 (s, 6 H), 1.62 (s, 9 H), 2.38 (d, 2 H, J=4.6 Hz), 2.50 (s, 3 H), 4.08 (s, 3 H), 6.18 (t, 1 H, J=4.4 Hz), 7.35 (s, 1 H), 7.45 (s, 1 H).

1,1,1-Trifluoromethanesulfonic acid 3,5,5,8-tetramethyl-5,6-dihydronaphthalen-2-yl ester (Compound 11)

General Procedure B To a solution of sodium hydride 60% w/w (0.27 g, 6.8 mmol) and 10 mL of DMF under the argon atmosphere was added slowly ethanethiol (0.50 mL, 6.8 mmol), and the resulting solution was stirred for 15 min. A solution of 6-methoxy-1,1,4,7-tetramethyl-1,2-dihydro-naphthalene (Compound 7, 0.42 g, 1.9 mmol) and 5 mL of DMF was then added, and the reaction mixture was refluxed for 4 h, cooled to room temperature, acidified with HCl 2 N, diluted with water, extracted with ethyl acetate, washed with brine, dried over $MgSO_4$, and filtered. The solvent was removed under reduced pressure, and the residue was dissolved in 5 mL of dichloromethane. DMAP (0.48 g, 3.9 mmol) was added, followed by 2-[N,N-bis(trifluoromethylsulfonyl)amino]-5-chloropyridine (1.2 g, 2.9 mmol), and the resulting reaction mixture was stirred for 24 h, then diluted with water, extracted with ethyl acetate, washed with brine, dried over $MgSO_4$, and filtered. The solvent was removed, and the residue was purified by flash column (hexane:ethyl acetate=4:1) to give 0.63 g (97%) of the title compound as a clear oil.
PNMR (300 MHz, $CDCl_3$) δ 1.28 (s, 6 H), 2.05 (s, 3 H), 2.21 (d, 2 H, J=4.4 Hz), 2.39 (s, 3 H), 5.83 (s, 1 H), 7.08 (s, 1 H), 7.22 (s, 1 H).

1,1,1-Trifluoromethanesulfonic acid 8-ethyl-3,5,5-trimethyl-5,6-dihydronaphthalen-2-yl ester (Compound 12)

Following General Procedure B, 4-ethyl-6-methoxy-1,1,7-trimethyl-1,2-dihydro-naphthalene (Compound 8, 0.33 g, 1.4 mmol) was reacted to give 0.32 g (64%) of the title compound as a clear oil.
PNMR (300 MHz, $CDCl_3$) δ 1.20 (t, 3 H, J=6.0 Hz), 1.26 (s, 6 H), 2.22 (d, 2 H, J=4.5 Hz), 2.40 (s, 3 H), 2.45 (m, 2 H), 5.82 (t, 1 H, J=4.5 Hz), 7.12 (s, 1 H), 7.22 (s, 1 H).

1,1,1-Trifluoromethanesulfonic acid-8-isopropyl-3,5,5-trimethyl-5,6-dihydronaphthalen-2-yl ester (Compound 13)

Following General Procedure B, 4-isopropyl-6-methoxy-1,1,7-trimethyl-1,2-dihydronaphthalene (Compound 9, 1.2 g, 4.7 mmol) was reacted to give 0.85 g (49%) of the title compound as a clear yellow oil.
PNMR (300 MHz, $CDCl_3$) δ 1.19 (d, 6 H, J=6.8 Hz), 1.26 (s, 6 H), 2.21 (d, 2 H, J=4.5 Hz), 2.40 (s, 3 H), 2.85 (m, 1 H), 5.92 (t, 1 H, J=4.4 Hz), 7.19 (s, 1 H), 7.24 (s, 1 H).

1,1,1-Trifluoromethanesulfonic acid-8-t-butyl-3,5,5-trimethyl-5,6-dihydronaphthalen-2-yl ester (Compound 14)

Following General Procedure B, 4-tert-butyl-6-methoxy-1,1,7-trimethyl-1,2,-dihydronaphthalene (Compound 10, 0.92 g, 3.6 mmol) was reacted to give 0.45 g (35%) of the title compound as a clear oil.
PNMR (300 MHz, $CDCl_3$) δ 1.22 (s, 6 H), 1.35 (s, 9 H), 2.18 (d, 2 H, J=4.5 Hz), 2.38 (s, 3 H), 6.02 (t, 1 H, J=4.4 Hz), 7.20 (s, 1 H), 7.52 (s, 1 H).

Ethyl 4-(3,5,5,8-tetramethyl-5,6-dihydronaphthalen-2-yl)amino]benzoate (Compound 15)

General Procedure C A solution of 1,1,1-trifluoromethanesulfonic acid 3,5,8,8-tetramethyl-5,6-dihydronaphthalen-2-yl ester (Compound 11, 0.21 g, 0.62 mmol), $Pd(dba)_2$ (0.034 g, 0.06 mmol), BINAP (0.11 g, 0.18 mmol), $Cs_2CO_3$ (0.30 g, 0.92 mmol), ethyl 4-aminobenzoate (0.15 g, 0.92 mmol) and 5 mL of toluene was flushed with argon for 10 min, then stirred at 100° C. in a sealed tube for 48 h. After the reaction mixture was cooled to room temperature, the solvent was removed, and the residue was purified by flash chromatography (hexane:ethyl acetate=4:1) to give 0.23 g (100%) of the title compound as a light yellow solid.
PNMR (300 MHz, $CDCl_3$) δ 1.25 (s, 6 H), 1.38 (t, 3 H, J=7.5 Hz), 2.16 (s, 3 H), 2.20 (d, 2 H, J=4.5 Hz), 2.25 (s, 3 H), 4.32 (q, 2 H, J=7.1 Hz), 5.72 (s, 1 H), 5.98 (s, 1 H), 6.74 (d, 2 H, J=8.7 Hz), 7.15 (s, 1 H), 7.18 (s, 1 H), 7.90 (d, 2 H, J=8.7 Hz).

Ethyl 4-[(8-Ethyl-3,5,5-trimethyl-5,6-dihydronaphthalen-2-yl)amino]benzoate (Compound 16)

Following General Procedure C, 1,1,1-trifluoromethanesulfonic acid 8-ethyl-3,5,5-trimethyl-5,6-dihydronaphthalen-2-yl ester (Compound 12, 0.32 g, 0.92 mmol) was reacted to give 0.25 g (75%) of the title compound as a yellow solid.
PNMR (300 MHz, $CDCl_3$) δ 1.15 (t, 3 H, J=6.5 Hz), 1.30 (s, 6 H), 1.40 (t, 3 H, J=6.5 Hz), 2.22 (d, 2 H, J=2.5 Hz), 2.26 (s, 3 H), 2.42 (q, 2 H, J=6.5 Hz), 4.36 (q, 2 H, J=7.1 Hz), 5.40 (s, 1 H), 5.78 (t, 1 H, J=4.4 Hz), 6.80 (d, 2 H, J=8.7 Hz), 7.22 (s, 2 H), 7.92 (d, 2 H, J=8.7 Hz).

Ethyl 4-[(8-isopropyl-3,5,5-trimethyl-5,6-dihydronanaphthalen-2-yl)amino]benzoate (Compound 17)

Following General Procedure C, 1,1,1-trifluoromethanesulfonic acid 8-isopropyl-3,5,5-trimethyl-5,6-dihydronaphthalen-2-yl ester (Compound 13, 0.85 g, 2.3 mmol) was reacted to give 0.48 g (55%) of the title compound as a yellow solid.
PNMR (300 MHz, $CDCl_3$) δ 1.13 (d, 6 H, J=6.8 Hz), 1.25 (s, 6 H), 1.35 (t, 3 H, J=7.0 Hz), 2.19 (d, 2 H, J=4.4 Hz), 2.24 (s, 3 H), 2.80 (m, 1 H), 4.35 (q, 2 H, J=7.1 Hz), 5.66 (s, 1 H), 5.77 (t, 1 H, J=4.4 Hz), 6.75 (d, 2 H, J=8.7 Hz), 7.19 (s, 1 H), 7.24 (s, 1 H), 7.89 (d, 2 H, J=8.7 Hz).

Ethyl 4-[(8-t-butyl-3,5,5-trimethyl-5,6-dihydronaphthalen-2yl)amino]benzoate (Compound 18)

Following General Procedure C, 1,1,1-trifluoromethanesulfonic acid 8-tert-butyl-3,5,5-trimethyl-5,6-dihydronaphthalen-2-yl ester (Compound 14, 0.45 g, 1.2 mmol) was reacted to give 0.14 g (31%) of the title compound as a light yellow solid.
PNMR (300 MHz, $CDCl_3$) δ 1.26 (s, 6 H), 1.31 (s, 9 H), 1.38 (t, 3 H, J=6.9 Hz), 2.16 (d, 2 H, J=4.9 Hz), 2.25 (s, 3 H), 4.34 (q, 2 H, J=7.0 Hz), 5.74 (s, 1 H), 5.96 (t, 1 H, J=4.7 Hz), 6.78 (d, 2 H, J=8.7 Hz), 7.20 (s, 1 H), 7.57 (s, 1 H), 7.91 (d, 2 H, J=8.7 Hz).

Ethyl 4-[ethyl(3,5,5,8-tetramethyl-5,6-dihydronaphthalen-2-yl)amino]benzoate (Compound 19)

General Procedure D To a solution of 4-[(3,5,5,8-Tetramethyl-5,6-dihydronaphthalen-2-yl)amino]benzoate (Compound 15, 0.20 g, 0.58 mmol) and 5 mL of THF was added acetaldehyde (0.30 mL, 5.8 mmol), followed by $NaBH_3CN$ (0.10 g, 1.74 mmol) and glacial acetic acid (2 mL). The resulting reaction mixture was stirred at room temperature for 24 h, then treated with water and ethyl acetate. The layers were separated, and the aqueous layer was extracted three times with ethyl acetate. The combined organic layers were washed with $NaHCO_3$ 1 N, brine, and dried over $MgSO_4$, and filtered. The solvent was removed, and the residue was purified by flash column (hexane:ethyl acetate=4:1) to give 0.19 g (88%) of the title compound as a light yellow solid.
PNMR (300 MHz, $CDCl_3$) δ 0.93 (t, 3 H, J=6.8 Hz), 1.31 (s, 6 H), 1.35 (t, 3 H, J=7.1 Hz), 2.02 (s, 3 H), 2.11 (s, 3 H), 2.24 (d, 2 H, J=4.2 Hz), 3.72 (q, 2 H, J=6.6 Hz), 4.32 (q, 2 H, J=7.1 Hz), 5.75 (s, 1 H), 6.49 (d, 2 H, J=9.0 Hz), 6.99 (s, 1 H), 7.25 (s, 1 H), 7.87 (d, 2 H, J=9.2 Hz).

Ethyl 4-[ethyl(8-ethyl-3,5,3-trimethyl-5,6-dihydronaphthalen-2-yl)amino]benzoate (Compound 20)

Following General Procedure D, ethyl 4-[(8-ethyl-3,5,5-trimethyl-5,6-dihydronaphthalen-2-yl)amino]benzoate (Compound 16, 0.25 g, 0.69 mmol) was reacted with acetaldehyde (0.8 mL, 13.8 mmol) to give 0.12 g (43%) of the title compound as a clear oil.
PNMR (300 MHz $CDCl_3$) δ1.27 (t, 3 H, J=7.5 Hz), 1.29 (m, 3 H), 1.31 (s, 6 H), 1.36 (t, 3 H, J=7.0 Hz), 2.11 (s, 3 H), 2.25 (d, 2 H, J=4.5 Hz), 2.41 (q, 2 H, J=6.1 Hz), 3.71 (q, 2 H, J=6.6 Hz), 4.32 (q, 2 H, J=7.1 Hz), 5.76 (s, 1 H), 6.49 (d, 2 H, J=8.9 Hz), 7.02 (s, 1 H), 7.26 (s, 1 H), 7.87 (d, 2 H, J=9.2 Hz).

Ethyl 4-[ethyl(8-isopropyl-3,5,5-trimethyl-5,6-dihydronaphthalen-2-yl)amino]benzoate (Compound 21)

Following General Procedure D, ethyl 4-[(8-isopropyl-3,5,5-trimethyl-5,6-dihydronaphthalen-2-yl)amino]benzoate (Compound 17, 0.48 g, 1.28 mmol) was reacted with acetaldehyde (0.9 mL, 12.8 mmol) to give 0.26 g (50%) of the title compound as a clear oil.
PNMR (300MHz, CDCl$_3$) δ 1.16 (t, 3 H, J=6.7 Hz), 1.31 (s, 6 H), 1.37 (t, 3 H, J=7.1 Hz), 2.14 (s, 3 H), 2.24 (d, 2 H, J=4.4 Hz), 2.88 (m, 1 H), 3.73 (s, 2 H), 4.34 (q, 2 H, J=7.0 Hz), 5.79 (s, 1 H), 6.52 (d, 2 H, J=8.4 Hz), 7.10 (s, 1 H), 7.28 (s, 1 H), 7.90 (d, 2 H, J=8.5 Hz).

Ethyl 4-[ethyl(8-t-butyl-3,5,5-trimethyl-5,6-dihydronaphthalen-2-yl) amino]benzoate (Compound 22)

Following General Procedure D, ethyl 4-[(8-tert-butyl-3,5,5-trimethyl-5,6-dihydronaphthalen-2yl)amino]benzoate (Compound 18, 0.14 g, 0.37 mmol) was reacted with acetaldehyde (0.40 mL, 7.4 mmol) to give 0.12 g (75%) of the title compound as a light yellow solid.
PNMR (300 MHz, CDCl$_3$) δ 1.27 (s, 6 H), 1.29 (m, 3 H), 1.31 (s, 9 H), 2.10 (s, 3 H), 2.18 (d, 2 H, J=4.9 Hz), 3.72 (q, 2 H, J=6.6 Hz), 4.33 (q, 2 H, J=7.1 Hz), 5.95 (t, 1 H, J=5.0 Hz), 6.50 (d, 2 H, J=8.9 Hz), 7.24 (s, 1 H), 7.38 (s, 1 H), 7.88 (d, 2 H, J=9.0 Hz).

4-[Ethyl(3,5,5,8-tetramethyl-5,6-dihydronaphthalen-2-yl)amino]benzoic acid (Compound 23)

General Procedure E To a solution of ethyl 4-[ethyl(3,5,8,8-tetramethyl-5,6-dihydronaphthalen-2-yl)amino]benzoate, (Compound 19, 0.17 g, 0.45 mmol) and 5 mL of absolute ethyl alcohol was added aqueous 5 M KOH (2 mL). The resulting solution was heated in an 60° C. bath for 24 h. The solution was cooled to room temperature, diluted with water and washed once with 2:1 hexane:ethyl acetate solution, and the layers were separated. The aqueous layer was acidified with HCl 2 N to pH=0–1 and the product extracted three times with ethyl acetate. The combined organic extracts were washed with brine, dried over MgSO$_4$, and filtered. The solvent was removed to give 0.042 g (92%) of the title compound as an off-white solid.
PNMR (300 MHz, CDCl$_3$) δ 1.32 (s, 6 H), 1.34 (m, 3 H), 2.03 (s, 3 H), 2.13 (s, 3 H), 2.25 (d, 2 H, J=2.4 Hz), 3.75 (s,2 H), 5.78 (s, 1 H), 6.51 (d, 2 H, J=8.8 Hz), 7.00 (s, 1 H), 7.26 (s, 1 H), 7.93 (d, 2 H, J=9.0 Hz).

4-Ethyl(8-ethyl-3,5,5-trimethyl-5,6-dihydronaphthalen-2-yl)amino]benzoic acid (Compound 24)

Following General Procedure E, ethyl 4-[ethyl(8-ethyl-3,5,5-trimethyl-5,6-dihydronaphthalen-2-yl)amino]benzoate (Compound 20, 0.12 g, 0.30 mmol) was reacted to give 0.13 g (100%) of the title compound as an off-white solid.
PNMR (300 MHz, CDCl$_3$) δ 1.15 (t, 3 H, J=7.3 Hz), 1.28 (m, 3 H), 1.30 (s, 6 H), 2.11 (s, 3 H), 2.14 (s, 3 H), 2.23 (d, 2 H, J=4.4 Hz), 2.41 (q, 2 H, J=7.7 Hz), 3.72 (s, 2 H), 5.77 (s, 1 H), 6.49 (d, 2 H, J=8.8 Hz), 7.01 (s, 1 H), 7.26 (s, 1 H), 7.90 (d, 2 H, J=8.9 Hz).

4-[Ethyl(8-isopropyl-3,5,5-trimethyl-5,6-dihydronaphthalen-2-yl)amino]benzoic acid (Compound 25)

Following General Procedure E, ethyl 4-[ethyl(8-isopropyl-3,5,5-trimethyl-5,6-dihydronaphthalen-2-yl)amino]benzoate (Compound 21, 0.24 g, 0.60 mmol) was reacted to give 0.23 g (100%) of the title compound as an off-white solid.
PNMR (300 MHz, CDCl$_3$) δ 1.14 (d, 6 H, J=6.7 Hz), 1.27 (m, 3 H), 1.29 (s, 6 H), 2.12 (s, 3 H), 2.14 (s, 3 H), 2.23 (d, 2 H, J=4.4 Hz), 2.85 (m, 1 H), 3.73 (s, 2 H), 5.78 (t, 1 H, J=4.4 Hz), 6.51 (d, 2 H, J=8.8 Hz), 7.06 (s, 1 H), 7.26 (s, 1 H), 7.91 (d, 2 H, J=9.0 Hz).

4-[Ethyl(8-t-butyl-3,5,5-trimethyl-5,6-dihydronaphthalen-2-yl)amino]benzoic acid (Compound 26)

Following General Procedure E, 4-ethyl 4[ethyl(8-tert-butyl-3,5,5-trimethyl-5,6-dihydronaphthalen-2-yl)amino)]benzoate (Compound 22, 0.12 0.27 mmol) was reacted to give 0.13 g (100%) of the title compound as an off-white solid.
PNMR (300 MHz, CDCl$_3$) δ 1.26 (s, 6 H), 1.29 (s, 9 H), 1.31 (m, 3 H), 2.09 (s, 3 H), 2.12 (s, 3 H), 2.18 (d, 2 H, J=4.9 Hz), 3.72 (s, 2 H), 5.95 (t, 1 H, J=6.4 Hz), 6.50 (d, 2 H, J=9.0 Hz), 7.24 (s, 1 H), 7.36 (s, 1 H), 7.89 (d, 2 H, J=9.1 Hz).

4-(4-Methoxy-3-methylphenylbutyric acid (Compound 27)

Zinc dust (40.0 g) was washed with HCl 10% and shaken for 2 min, and the water was decanted. HgCl$_2$ (6.0 g) was then added, followed by water (60 mL) and concentrated HCl (2 mL). The mixture was shaken for 5 min, the water was decanted, and covered with water (30 mL) and concentrated HCl (70 mL). Toluene (20 mL) was added, followed by 4-(4-methoxy-3-methylphenyl)-4-oxobutyric acid (Compound 2, 11.7 g, 52.7 mmol). The resulting solution was refluxed vigorously for 24 h with addition of concentrated HCl (3×20 mL every 3 h). After being cooled down to room temperature, the two layers were separated, and the aqueous layer was washed three times with diethyl ether. The combined organic layers were washed with brine, dried over MgSO$_4$, and filtered. The solvent was removed to give 10.7 g (98%) of the title compound as a light yellow solid.
PNMR (300 MHz, CDCl$_3$) δ 1.95 (quin, 2 H, J=7.5 Hz), 2.22 (s, 3 H), 2.37 (t, 2 H, J=7.5 Hz), 2.60 (t, 2 H, J=7.5 Hz), 3.82 (s, 3 H), 6.75 (d, 1 H, J=8.0 Hz), 6.97 (d, 2 H, J=5.0 Hz).

7-Methoxy-6-methyl-3,4-dihydro-2H-naphthalen-1-one (Compound 28)

A solution of 4-(4-methoxy-3-methylphenyl)butyric acid (Compound 27, 24.0 g, 115.4 mmol) and 400 mL of methanesulfonic acid was stirred at room temperature under the argon atmosphere for 24 h, then poured into ice, extracted three times with ethyl acetate, washed with NaHCO$_3$ 1 N, brine, dried over MgSO$_4$, and filtered. The solvent was removed to give 19.2 g (88%) of the title compound as a dark brown solid.
PNMR (300 MHz, CDCl$_3$) δ 2.12 (quin, 2 H, J=6.0 Hz), 2.27 (s, 3 H), 2.62 (t, 2 H, J=7.5 Hz), 2.87 (t, 2 H, J=7.5 Hz), 3.88 (s, 3 H), 7.02 (s, 1 H), 7.48 (s, 1 H).

7-Methoxy-1,1,6-trimethyl-1,2,3,4-tetrahydronaphthalene (Compound 29)

To a solution of TiCl$_4$ 1 M in CH$_2$Cl$_2$ (60 mL, 60 mL) at −40° C. under the argon atmosphere was added a solution of Me$_2$Zn 2 M in toluene, and the resulting dark brown cloudy mixture was stirred for 15 min. A solution of 7-methoxy-6-methyl-3,4-dihydro-2H-naphthalen-1-one (Compound 28, 6.4 g, 33.5 mmol) and 20 mL of dichloromethane was then added, and the temperature was raised to 0° C., then to room temperature. After 5 h, the reaction was cooled to 0° C., quenched with methanol until no more bubbling was observed. Saturated NH$_4$Cl was added, and the reaction mixture was extracted three times with dichloromethane, washed with NaHCO$_3$ 1 N, brine, dried over MgSO$_4$, and filtered. The solvent was removed to give 6.1 g (90%) of the title compound as an amber oil.
PNMR (300 MHz, CDCl$_3$) δ 1.29 (s, 6 H), 1.64 (t, 2 H, J=5.3 Hz), 1.79 (m, 2 H), 2.18 (s, 1 H), 3.83 (s, 3 H), 7.20 (d, 1 H, J=6.8 Hz), 7.26 (d, 1 H, J=6.8 Hz).

6-Methoxy-4,4,7-trimethyl-3,4-dihydro-2H-naphthalen-1-one (Compound 30)

To a solution of 7-methoxy-1,1,6-trimethyl- 1,2,3,4-tetrahydronaphthalene (Compound 29, 14.7 g, 72.1 mmol) and 30 mL of glacial acetic acid at 0° C. was added a cold solution of $CrO_3$ (14.5 g, 144.2 mmol) in 30 mL of glacial acetic acid and 15 mL of water. The resulting dark solution was stirred at 0° C. for 1 h, then quenched with NaOH 2 N, extracted with diethyl ether, washed with brine, dried over $MgSO_4$, and filtered. The solvent was removed to give 11.3 g (72%) of the title compound as a dark brown solid. PNMR (300 MHz, $CDCl_3$) δ 1.38 (s, 6 H), 1.98 (t, 2 H, J=7.5 Hz), 2.10 (s, 3 H), 2.68 (t, 2 H, J=7.5 Hz), 3.90 (s, 3 H), 6.76 (s, 1 H), 7.83 (d, 1 H).

7-Methoxy- 1,1,4,6-tetramethyl-1,2-dihydro-naphthalene (Compound 31)

General Procedure F $CeCl_3 \cdot 7H_2O$ (2.6 g, 6.9 mmol) was heated in an oil bath at 140–150° C. under high vacuum without stirring for 1 h, and then with stirring for 2 h. Argon was then introduced, and the flask was cooled to room temperature. Tetrahydrofuran (15 mL) was added, and the resulting slurry solution was stirred at room temperature under the argon atmosphere for 16 h. A solution of 6-methoxy-4,4,7-trimethyl-3,4-dihydro-2H-naphthalen-1-one (Compound 30, 1.0 g, 4.6 mmol) and 5 mL of tetrahydrofuran was added, and the reaction mixture was stirred for 1 h, then cooled to 0° C. A solution of 3 M MeMgBr in diethyl ether (2.3 mL, 6.9 mmol) was added, and the ice bath was removed. After 1 h, the reaction was poured into concentrated sulfuric acid in ice, extracted with ethyl acetate, washed with $NaHCO_3$ 1 N, brine, dried over $MgSO_4$, and filtered. The solvent was removed to give 1.0 g (100%) of the title compound as an orange oil. PNMR (300 MHz, $CDCl_3$) δ 1.52 (s, 6 H), 2.28 (s, 3 H), 2.42 (d, 2 H, J=3.4 Hz), 2.49 (s, 1 H), 4.07 (s, 3 H), 5.86 (t, 1 H, J=2.5 Hz), 7.08 (s, 1 H), 7.30 (s, 1 H).

4-Ethyl-7-methoxy-1,1,6-trimethyl-1,2-dihydro-naphthalene (Compound 32)

Following General Procedure F, 6-methoxy-4,4,7-trimethyl-3,4-dihydro-2H-naphthalen-1-one (compound 30, 1.0 g, 4.6 mmol) was reacted with a solution of 3 M EtMgBr (8 mL, 23.0 mmol), and the crude product was purified by flash column (hexane:ethyl acetate=96:4) to give 0.42 g (40%) of the title compound as a clear oil. PNMR (300 MHz, $CDCl_3$) δ 1.36 (t, 3 H, J=6.0 Hz), 1.46 (s, 6 H), 2.35 (d, 2 H, J=4.5 Hz), 2.42 (s, 3 H), 2.65 (q, 2 H, J=7.5 Hz), 4.03 (s, 3 H), 5.82 (t, 1 H, J=2.5 Hz), 7.02 (s, 1 H), 7.28 (s, 1 H).

4-Isopropyl-7-methoxy-1,1,6-trimethyl-1,2-dihydronaphthalene (Compound 33)

Following General Procedure F, 6-methoxy-4,4,7-trimethyl-3,4-dihydro-2H-naphthalen-1-one (compound 30) (1.5 g, 6.9 mmol) was reacted with a solution of 2 M isopropylmagnesiumchloride (17 mL, 34.5 mmol), and the crude product was purified by flash column (hexane:ethyl acetate=4:1) to give 0.88 g (53%) of the title product as a yellow oil. PNMR (300 MHz, $CDCl_3$) δ 1.36 (d, 6 H, J=7.5 Hz), 1.55 (s, 6 H), 2.45 (d, 2 H, J=4.5 Hz), 2.52 (s, 3 H), 3.25 (m, 1 H), 4.10 (s, 3 H), 5.82 (t, 1 H, J=2.5 Hz), 7.12 (s, 1 H), 7.42 (s, 1 H).

4-t-Butyl-7-methoxy- 1,1,6-trimethyl-1,2,-dihydronaphthalene (Compound 34)

Following General Procedure F, 6-methoxy-4,4,7-trimethyl-3,4-dihydro-2H-naphthalen-1-one (Compound 30, 2.0 g, 9.2 mmol) was reacted with a solution of 2 M tert-butylmagnesiumchloride (46 mL, 92.0 mmol), and the crude product was purified by flash column (hexane:ethyl acetate=4:1) to give 0.23 g (10%) of the title product as a yellow oil.

PNMR (300 MHz, $CDCl_3$) δ 1.32 (s, 6 H), 1.42 (s, 9 H), 2.22 (d, 2 H, J=4.5 Hz), 2.35 (s, 3 H), 3.92 (s, 3 H), 5.92 (t, 1 H, J=2.5 Hz), 6.92 (s, 1 H), 7.56 (s, 1 H).

Trifluoromethanesulfonic acid 3,5,8,8-tetramethyl-7,8-dihydronaphthalen-2-yl ester (Compound 35)

General Procedure G

To a solution of sodium hydride 60% w/w (0.70 g, 17.4 mmol) and 15 mL of DMF under the argon atmosphere was added slowly ethanethiol (1.3 mL, 17.4 mmol), and the resulting solution was stirred for 15 min. A solution of 7-methoxy-1,1,4,6-tetramethyl-1,2-dihydro-naphthalene (Compound 31, 1.1 g, 5.0 mmol) and 5 mL of DMF was then added, and the reaction mixture was refluxed for 4 h, cooled to room temperature, acidified with HCl 2 N, diluted with water, extracted with ethyl acetate, washed with brine, dried over $MgSO_4$, and filtered. The solvent was removed under reduced pressure, and the residue was dissolved in 5 mL of dichloromethane. DMAP (1.71 g, 14.0 mmol) was added, followed by 2-[N,N-bis(trifluoromethylsulfonyl)amino]-5-chloropyridine (2.75 g, 7.0 mmol), and the resulting reaction mixture was stirred for 30 min, then diluted with water, extracted with ethyl acetate, washed with brine, dried over $MgSO_4$, and filtered. The solvent was 2 removed, and the residue was purified by flash column (hexane:ethyl acetate=4:1) to give 0.9 g (60%) of the title compound as a clear oil. PNMR (300 MHz, $CDCl_3$) δ 1.30 (s, 6 H), 2.10 (s, 3 H), 2.22 (d, 2 H, J=3.4 Hz), 2.42 (s, 3 H), 5.82 (s, 1 H), 7.18 (s, 2 H).

Trifluoromethanesulfonic acid 5-ethyl-3,8,8-trimethyl-7,8-dihydronaphthalen-2-yl ester (Compound 36)

Following General Procedure G, 4-ethyl-7-methoxy-1,1,6-trimethyl-1,2-dihydro-naphthalene (Compound 32, 0.42 g, 1.8 mmol) was reacted to give 0.53 g (84%) of the title compound as a clear oil.

PNMR (300 MHz, $CDCl_3$) δ 1.20 (t, 3 H, J=6.0 Hz), 1.22 (s, 6 H), 2.22 (d, 2 H, J=4.5 Hz), 2.30 (s, 3 H), 2.50 (q, 2 H, J=7.5 Hz), 5.84 (t, 1 H, J=2.5 Hz), 7.18 (s, 1 H), 7.22 (s, 1 H).

Trifluoromethanesulfonic acid 5-isopropyl-3,8,8-trimethyl-7,8-dihydronaphthalen-2-yl ester (Compound 37)

Following General Procedure G, 4-isopropyl-7-methoxy-1,1,6-trimethyl-1,2-dihydronaphthalene (Compound 33, 1.6 g, 6.6 mmol) was reacted to give 1.7 g (83%) of the title compound as a clear yellow oil.

PNMR (300 MHz, $CDCl_3$) δ 1.25 (d, 6 H, J=7.5 Hz), 1.32 (s, 6 H), 2.25 (d, 2 H, J=4.5 Hz), 2.42 (s, 3 H), 3.02 (m, 1 H), 5.92 (t, 1 H, J=2.5 Hz), 7.22 (s, 1 H), 7.32 (s, 1 H).

Trifluoromethanesulfonic acid 5-t-butyl-3,8,8-trimethyl-7,8-dihydronaphthalen-2-yl ester (Compound 38)

Following General Procedure G, 4-tert-butyl-7-methoxy-1,1,6-trimethyl-1,2,-dihydronaphthalene (Compound 34, 0.23 g, 0.87 mmol) was reacted to give 0.080 g (22%) of the title compound as a clear oil.

PNMR (300 MHz, $CDCl_3$) δ 1.22 (s, 6 H), 1.38 (s, 9 H), 2.16 (d, 2 H, J=4.5 Hz), 2.38 (s, 3 H), 6.02 (t, 1 H, J=2.5 Hz), 7.12 (s, 1 H), 7.58 (s, 1 H).

Ethyl 4-(3,5,8,8-tetramethyl-7,8-dihydro-naphthalen-2-yl-amino)benzoate (Compound 39)

General Procedure H A solution of trifluoromethanesulfonic acid 3,5,8,8-tetramethyl-7,8-dihydronaphthalen-2-yl ester (Compound 35, 0.41 g, 1.2 mmol), $Pd(OAc)_2$ (0.027 g, 0.12 mmol), BINAP (0.11 g, 0.18 mmol), $Cs_2CO_3$ (0.56 g, 1.72 mmol), ethyl 4-aminobenzoate (0.25 g, 1.5 mmol) and 5 mL of toluene was flushed with argon for 10 min, then stirred at 100° C. in a sealed tube for 48 h. After the reaction mixture had been cooled to room temperature, the solvent was removed, and the residue was purified by flash column (hexane:ethyl acetate=4:1) to give 0.34 g (80%) of the title compound as a yellowish solid.
PNMR (300 MHz, CDCl$_3$) δ1.28 (s, 6 H), 1.42 (t, 3 H, J=7.5 Hz), 2.12 (s, 3 H), 2.22 (d, 2 H, J=4.5 Hz), 2.28 (s, 3 H), 4.38 (q, 2 H, J=7.5 Hz), 5.78 (t, 1 H, J=2.5 Hz), 6.02 (s, 1 H), 6.84 (d, 2 H, J=8.0 Hz), 7.18 (s, 1 H), 7.28 (s, 1 H), 7.95 (d, 2 H, J=8.0 Hz).

Ethyl 4-(5-ethyl-3,8,8-trimethyl-7,8-dihydro-naphthalen-2-ylamino)benzoate (Compound 55)

Following General Procedure H, trifluoromethanesulfonic acid 5-ethyl-3,8,8-trimethyl-7,8-dihydronaphthalen-2-yl ester (Compound 36, 0.5 g, 1.5 mmol) was reacted to give 0.36 g (66%) of the title compound as a yellow solid.
PNMR (300 MHz, CDCl$_3$) δ_1.22 (s, 6 H), 1.42 (t, 3 H, J=7.5 Hz), 2.22 (d, 2 H, J=2.5 Hz), 2.26 (s, 3 H), 2.52 (q, 2 H, J=7.5 Hz), 4.35 (q, 2 H, J=7.5 Hz), 5.75 (t, 1 H, J=2.5 Hz), 5.86 (s, 1 H), 6.84 (d, 2 H, J=8.0 Hz), 7.20 (s, 1 H), 7.28 (s, 1 H), 7.92 (d, 2 H, J=8.0 Hz).

Ethyl 4-[(5-isopropyl-3,8,8-trimethyl-7,8-dihydro-naphthalen-2-yl)amino]benzoate (Compound 48)

Following General Procedure H, trifluoromethanesulfonic acid 5-isopropryl-3,8,8-trimethyl-7,8-dihydronaphthalen-2-yl ester (Compound 37, 0.83 g, 2.3 mmol) was reacted to give 0.29 g (34%) of the title compound as a yellow solid.
PNMR (300 MHz, CDCl$_3$) δ 1.20 (d, 6 H, J=6.0 Hz), 1.22 (s, 6 H), 1.42 (t, 3 H, J=7.5 Hz), 2.22 (d, 2 H, J=4.5 Hz), 2.26 (s, 3 H), 3.01 (m, 1 H), 4.35 (q, 2 H, J=7.5 Hz), 5.76 (t, 1 H, J=2.5 Hz), 5.88 (s, 1 H), 6.83 (d, 2 H, J=8.0 Hz), 7.22 (s, 1 H), 7.29 (s, 1 H), 7.94 (d, 2 H, J=8.0 Hz).

Ethyl 4-[(5-t-butyl-3,8,8-trimethyl-7,8-dihydro-naphthalen-2-yl)amino]benzoate (Compound 56)

Following General Procedure H, trifluoromethanesulfonic acid 5-tert-butyl-3,8,8-trimethyl-7,8-dihydronaphthalen-2-yl ester (Compound 38, 0.08 g, 0.21 mmol) was reacted to give 0.019 g (23%) of the title compound as a clear oil.
PNMR (300 MHz, CDCl$_3$) δ 1.19 (s, 6 H), 1.38 (s, 9 H), 2.15 (d, 2 H, J=4.5 Hz), 2.26 (s, 3 H), 4.36 (q, 2 H, J=7.5 Hz), 5.74 (s, 1 H), 5.94 (t, 1 H, J=2.5 Hz), 6.83 (d, 2 H, J=8.0 Hz), 7.26 (s, 1 H), 7.56 (s, 1 H), 7.92 (d, 2 H, J=8.0 Hz).

Ethyl 4-methyl(3,5,8,8-tetramethyl-7,8-dihydronaphthalen-2-ylamino]benzoate (Compound 40)

Following the previously described General Procedure D to a solution of ethyl 4-(3,5,8,8-tetramethyl-7,8-dihydronaphthalen-2-ylamino)benzoate (Compound 39, 0.10 g, 0.27 mmol) and 6 mL of THF was added an aqueous solution of formaldehyde 37% (0.20 mL, 2.7 mmol), followed by NaBH$_3$CN (0.05 g, 0.82 mmol) and glacial acetic acid (5 mL). The resulting reaction mixture was stirred at room temperature for 24 h, then treated with water and ethyl acetate. The layers were separated, and the aqueous layer was extracted three times with ethyl acetate. The combined organic layers were washed with NaHCO$_3$ 1 N, brine, and dried over MgSO$_4$, and filtered. The solvent was removed, and the residue was purified by flash column (hexane:ethyl acetate=4:1) to give 0.050 g (50%) of the title compound as a yellow solid.
PNMR (300 MHz, CDCl$_3$) δ1.24 (s, 6 H), 1.38 (t, 3 H, J=7.5 Hz), 2.09 (s, 3 H), 2.22 (d, 2 H, J=4.5 Hz), 3.30 (s, 3 H), 4.34 (q, 2 H, J=7.5 Hz), 5.82 (t, 1 H, J=2.5 Hz), 6.52 (d, 2 H, J=8.0 Hz), 7.06 (s, 1 H), 7.18 (2, 1 H), 7.88 (d, 2 H, J=8.0 Hz).

Ethyl 4-[ethyl(3,5,8,8-tetramethyl-7,8-dihydronaphthalen-2-yl)amino]benzoate (Compound 41)

Following General Procedure D, ethyl 4-(3,5,8,8-tetramethyl-7,8-dihydronaphthalen-2-ylamino)benzoate (Compound 39, 0.055 g, 0.16 mmol) was reacted with acetaldehyde (90 μL, 1.6 mmol) to give 0.035 g (58%) of the title compound as a yellow oil.
PNMR (300 MHz, CDCl$_3$) δ1.24 (s, 6 H), 1.28 (t, 3 H, J=7.5 Hz), 1.36 (t, 3 H, J=7.5 Hz), 2.10 (s, 3 H), 2.12 (s, 3 H), 2.22 (d, 2 H, J=2.5 Hz), 3.72 (q, 2 H, J=6.0 Hz), 4.32 (q, 2 H, J=7.5 Hz), 5.82 (t, 1 H, J=2.5 Hz), 6.48 (d, 2 H, J=8.0 Hz), 7.02 (s, 1 H), 7.20 (s, 1 H), 7.85 (d, 2 H, J=8.0 Hz).

Ethyl 4-[propyl(3,5,8,8-tetramethyl-7,8-dihydronaphthalen-2-yl)amino]benzoate (Compound 42)

Following General Procedure D, ethyl 4-(3,5,8,8-tetramethyl-7,8-dihydronaphthalen-2-ylamino)benzoate (Compound 39, 0.085 g, 0.24 mmol) was reacted with propionaldehyde (180 μL, 2.4 mmol) to give 0.039 g (41%) of the title compound as a clear oil.
PNMR (300 MHz, CDCl$_3$) δ_0.98 (t, 3 H, J=7.5 Hz), 1.26 (s, 6 H), 1.36 (t, 3 H, J=7.5 Hz), 1.76 (m, 2 H), 2.12 (s, 3 H), 2.14 (s, 3 H), 2.22 (d, 2 H, J=2.5 Hz), 3.58 (t, 2 H, J=6.0 Hz), 4.32 (q, 2 H, J=7.5 Hz), 5.82 (s, 1 H), 6.48 (d, 2 H, J=8.0 Hz), 7.06 (s, 1 H), 7.20 (s, 1 H), 7.86 (d,2 H, J=8.0 Hz).

Ethyl 4-[cyclopropylmethyl(3,5,8,8-tetramethyl-7,8-dihydronaphthalen-2-yl)amino]benzoate (Compound 43)

Following General Procedure D, ethyl 4-(3,5,8,8-tetramethyl-7,8-dihydronaphthalen-2-ylamino)benzoate (Compound 39, 0.085 g, 0.24 mmol) was reacted with cyclopropane carboxaldehyde (180 μL, 2.4 mmol) to give 0.042 g (43%) of the title compound as a clear oil.
PNMR (300 MHz, CDCl$_3$) δ_0.15 (d, 2 H, J=4.5 Hz), 0.52 (d, 2 H, J=7.5 Hz), 1.22 (s,6 H), 1.36 (t,3 H, J=7.5 Hz), 2.10 (s, 3 H),2.22 (d, 2 H, J=2.5 Hz), 3.50 (s, 2 H), 4.32 (q, 2 H, J=7.5 Hz), 5.79 (t, 1 H, J=2.5 Hz), 6.52 (d, 2 H, J=8.0 Hz), 7.12 (s, 1 H), 7.16 (s, 1 H), 7.86 (d, 2 H, J=8.0 Hz).

Ethyl 4-[ethyl-(5-ethyl-3,8,8-trimethyl-7,8-dihydronaphthalen-2-yl)amino]benzoate (Compound 57)

Following General Procedure D, ethyl 4-(5-ethyl-3,8,8-tetramethyl-7,8-dihydronaphthalen-2-ylamino)benzoate (Compound 55, 0.37 g, 1.0 mmol) was reacted with acetaldehyde (0.56 mL, 10.0 mmol) to give 0.25 g (63%) of the title compound as a clear oil.
PNMR (300 MHz, CDCl$_3$) δ_1.22 (s, 6 H), 1.24 (t, 3 H, J=7.5 Hz), 1.38 (t, 3 H, J=7.5 Hz), 2.12 (s, 3 H), 2.22 (d, 2 H, J=2.5 Hz), 2.54 (q, s H, J=7.5 Hz),3.84 (q,2 H, J=7.5 Hz), 4.35 (q, 2 H, J=7.5 Hz),5.82 (t, 1 H, J=2.5 Hz), 6.52 (d, 2 H, J=8.0 Hz), 7.08 (s, 1 H), 7.26 (s, 1 H), 7.90 (d, 2 H, J=8.0 Hz).

Ethyl 4-[methyl-(5-isopropyl-3,8,8-trimethyl-7,8-dihydronaphthalen-2-yl)amino]benzoate (Compound 49)

Following General Procedure D, ethyl 4-(5-isopropyl-3,8,8-trimethyl-7,8-dihydronaphthalen-2-ylamino)benzoate (Compound 48, 0.10 g, 0.26 mmol) was reacted with an aqueous solution of formaldehyde 37% (0.20 mL, 2.6 mmol) to give 0.10 g (100%) of the title compound as a clear oil.
PNMR (300 MHz, CDCl$_3$) δ_1.26 (s, 6 H), 1.30 (d, 6 H, J=7.5 Hz), 1.35 (t, 3 H, J=7.5 Hz), 2.08 (s, 3 H), 2.22 (d, 2 H, J=2.5 Hz), 2.96 (m, 1 H), 3.28 (s, 3 H), 4.30 (q, 2 H, J=7.5 Hz), 5.80 (t, 1 H, J=2.5 Hz), 6.48 (d, 2 H, J=8.0 Hz), 7.03 (s, 1 H), 7.24 (s, 1 H), 7.84 (d, 2 H, J=8.0 Hz).

Ethyl 4-[ethyl-(5-isopropyl-3,8,8-trimethyl-7,8-dihydronaphthalen-2-yl)amino]benzoate (Compound 50)

Following General Procedure D, ethyl 4-(5-isopropyl-3,8,8-trimethyl-7,8-dihydronaphthalen-2-ylamino)benzoate (Compound 48, 0.10 g, 0.26 mmol) was reacted with acetaldehyde (0.15 mL, 2.6 mmol) to give 0.090 g (90%) of the title compound as a clear oil.
PNMR (300 MHz, CDCl$_3$) δ_1.18 (s, 6 H), 1.20 (d, 6 H, J=7.5 Hz), 1.28 (t, 3 H, J=7.5 Hz), 1.35 (t, 3 H, J=7.5 Hz), 2.10 (s,3 H), 2.22 (d, 2 H, J=2.5 Hz), 2.98 (m, 1 H), 4.32 (q, 2 H, J=7.5 Hz), 5.82 (t, 1 H, J=2.5 Hz), 6.48 (d, 2 H, J=8.0 Hz), 7.03 (s, 1 H), 7.23 (s, 1 H), 7.85 (d, 2 H, J=8.0 Hz).

Ethyl 4-[propyl-(5-isopropyl-3,8,8-trimethyl-7,8-dihydronaphthalen-2-yl)amino]benzoate (Compound 51)

Following General Procedure D, ethyl 4-(5-isopropyl-3,8,8-trimethyl-7,8-dihydronaphthalen-2-ylamino)benzoate (Compound 48, 0.10 g, 0.26 mmol) was reacted with propionaldehyde (0.20 mL, 2.6 mmol) to give 0.070 g (68%) of the title compound as a clear oil. PNMR (300 MHz, CDCl$_3$) δ 0.98 (t, 3 H, J=7.5 Hz), 1.22 (s, 6 H), 1.24 (d, 6 H, J=7.5 Hz), 1.36 (t, 3 H, J=7.5 Hz), 2.10 (s, 3 H), 2.22 (d, 2 H, J=2.5 Hz), 3.01 (m, 1 H), 3.58 (t, 2 H, J=7.5 Hz), 4.32 (q,2 H, J=7.5 Hz), 5.82 (t, 1 H, J=2.5 Hz), 6.48 (d, 2 H, J=8.0 Hz), 7.03 (s, 1 H), 7.23 (s, 1 H), 7.85 (d, 2 H, J=8.0 Hz).

Ethyl 4-[ethyl-(5-t-butyl-3,8,8-trimethyl-7,8-dihydronaphthalen-2-yl)amino]benzoate (Compound 58)

Following General Procedure D, ethyl 4-[(5-tert-butyl-3,8,8-trimethyl-7,8-dihydronaphthalen-2-yl)amino]benzoate (Compound 56, 0.019 g, 0.05 mmol) was reacted with acetaldehyde (0.030 mL, 0.5 mmol) to give 0.013 g (62%) of the title compound as a clear oil. PNMR (300 MHz, CDCl$_3$) δ 1.20 (s, 6 H), 1.32 (t, 3 H, J=7.5 Hz), 1.40 (s, 9 H), 2.08 (s, 3 H), 2.18 (d, 2 H, J=6.0 Hz), 3.72 (q, 2 H, J=7.5 Hz), 4.32 (q, 2 H, J=7.5 Hz), 5.98 (t 1 H, J=4.5 Hz), 6.48 (d, 2 H, J=8.0 Hz), 7.02 (s, 1 H), 7.68 (s, 1 H), 7.86 (d, 2 H, J=8.0 Hz).

4-[Methyl(3,5,8,8-tetramethyl-7,8-dihydronaphthalen-2-yl)amino]benzoic acid (Compound 44)

Following previously described General Procedure E, to a solution of ethyl 4-[methyl-(3,5,8,8-tetramethyl-7,8-dihydronaphthalen-2-yl)amino]benzoate (Compound 40, 0.05 g, 0.14 mmol) and 2 mL of absolute ethyl alcohol was added aqueous 5 M KOH (0.3 mL). The resulting solution was heated in an 60° C. bath for 24 h. The solution was cooled to room temperature, diluted with water and washed once with 2:1 hexane:ethyl acetate solution, and the layers were separated. The aqueous layer was acidified with HCl 2 N to pH=0–1 and the product extracted three times with ethyl acetate. The combined organic extracts were washed with brine, dried over MgSO$_4$, and filtered. The solvent was removed to give 0.042 g (92%) of the title compound as a dark green solid. PNMR (300 MHz, CDCl$_3$) δ 1.24 (s, 6 H), 2.12 (s, 3 H), 2.14 (s, 3 H), 2.22 (d, 2 H, J=2.4 Hz), 3.32 (s, 3 H), 5.81 (s, 1 H), 6.52 (d, 2 H, J=7.5 Hz), 7.08 (s, 1 H), 7.19 (s, 1 H), 7.92 (d, 2 H, J=7.5 Hz).

4-[Ethyl(3,5,8,8-tetramethyl-7,8-dihydronaphthalen-2-yl)amino]benzoic acid (Compound 45)

Following General Procedure E, ethyl 4-[ethyl(3,5,8,8-tetramethyl-7,8-dihydronaphthalen-2-yl)amino]benzoate (Compound 41, 0.035 g, 0.09 mmol) was reacted to give 0.027 g (83%) of the title compound as a yellow solid. PNMR (300 MHz, CDCl$_3$) δ 1.22 (s, 6 H), 1.26 (t, 3 H, J=7.5 Hz), 2.10 (s, 3 H), 2.12 (s, 3 H), 2.22 (d, 2 H, J=2.4 Hz), 3.72 (q, 2 H, J=6.0 Hz), 5.80 (t, 1 H, J=3.5 Hz), 6.48 (d, 2 H, J=7.7 Hz), 7.08 (s, 1 H), 7.19 (s, 1 H), 7.90 (d, 2 H, J=7.7 Hz).

4-[n-Propyl(3,5,8,8-tetramethyl-7,8-dihydronaphthalen-2-yl)amino]benzoic acid (Compound 46)

Following General Procedure E, ethyl 4-[n-propyl(3,5,8,8-tetramethyl-7,8-dihydronaphthalen-2-yl)amino]benzoate (Compound 42, 0.039 g, 0.10 mmol) was reacted to give 0.035 g (100%) of the title compound as a yellow solid. PNMR (300 MHz, CDCl$_3$) δ 0.98 (t,3 H, J=7.5 Hz), 1.24 (s, 6 H), 1.78 (m,2 H),2.08 (s,3 H),2.12 (s,3 H),2.22 (d,2 H, J=2.4 Hz),3.60 (s,2 H), 5.82 (t, 1 H, J=3.5 Hz), 6.48 (d, 2 H, J=7.7 Hz), 7.03 (s, 1 H), 7.20 (s, 1 H), 7.90 (d, 2 H, J=7.7 Hz).

4-[Cyclopropylmethyl(3,5,8,8-tetramethyl-7,8-dihydronaphthalen-2-yl)amino]benzoic acid (Compound 47)

Following General Procedure E, ethyl 4-[cyclopropylmethyl(3,5,8,8-tetramethyl-7,8-dihydronaphthalen-2-yl)amino]benzoate (Compound 43, 0.042 g, 0.10 mmol) was reacted to give 0.039 g (100%) of the title compound as a yellow solid. PNMR (300 MHz, CDCl$_3$) δ 0.14 (q, 2 H, J=4.5 Hz), 0.52 (q, 2 H, J=4.5 Hz), 1.24 (s, 6 H), 2.10 (m, 4 H), 2.12 (s, 3 H), 2.22 (d, 2 H, J=2.4 Hz), 3.50 (s, 2 H), 5.80 (t, 1 H, J=3.5 Hz), 6.52 (d, 2 H, J=7.7 Hz), 7.04 (s, 1 H), 7.08 (s, 1 H), 7.90 (d, 2 H, J=7.7 Hz).

4-[Ethyl(5-ethyl-3,8,8-trimethyl-7,8-dihydronaphthalen-2-yl)amino]benzoic acid (Compound 59)

Following General Procedure E, ethyl 4-[ethyl(5-ethyl-3,8,8-trimethyl-7,8-dihydronaphthalen-2-yl)amino]benzoat (Compound 57, 0.25 g, 0.63 mmol) was reacted to give 0.12 g (50%) of the title compound as a yellow solid. PNMR (300 MHz, CDCl$_3$) δ 1.25 (s, 6 H), 1.30 (m, 6 H), 2.12 (s, 3 H), 2.22 (d, 2 H, J=2.5 Hz), 2.52 (q, 2 H, J=5.3 Hz), 3.75 (q, 2 H, J=5.3 Hz), 5.80 (t, 1 H, J=3.5 Hz), 6.52 (d, 2 H, J=7.7 Hz), 7.04 (s, 1 H), 7.24 (s, 1 H), 7.92 (d, 2 H, J=7.7 Hz).

4-[Methyl-(5-isopropyl-3,8,8-trimethyl-7,8-dihydronaphthalen-2-yl)amino]benzoic acid (Compound 52)

Following General Procedure E, ethyl 4-[(5-isopropyl-3,8,8-trimethyl-7,8-dihydronaphthalen-2-yl)methylamino]benzoate, AGN 196549, (Compound 49, 0.12 g, 0.31 mmol) was reacted to give 0.074 g (66%) of the 28 title compound as a yellow solid. PNMR (300 MHz, CDCl$_3$) δ 1.24 (s, 6 H), 1.25 (d,6 H, J=7.5 Hz), 2.12 (s, 3 H), 2.22 (d, 2 H, J=2.5 Hz), 3.02 (m, 1 H), 3.32 (s, 1 H), 5.82 (t, 1 H, J=3.0 Hz), 6.52 (d, 2 H, J=7.7 Hz), 7.08 (s, 1 H), 7.28 (s, 1 H), 7.94 (d, 2 H, J=7.7 Hz).

4-[Ethyl-5-isopropyl-3,8,8-trimethyl-7,8-dihydronaphthalen-2-yl)amino]benzoic acid (Compound 53)

Following General Procedure E, ethyl 4-[(5-isopropyl-3,8,8-trimethyl-7,8-dihydronaphthalen-2-yl)methylamino]benzoate (Compound 50, 0.09 g, 0.22 mmol) was reacted to give 0.048 g (57%) of the title compound as a yellow solid. PNMR (300 MHz, CDCl$_3$) δ 1.22 (s, 6 H), 1.24 (d, 6 H, J=7.5 Hz), 1.32 (t, 3 H, J=7.5 Hz), 2.12 (s, 3 H), 2.25 (d, 2 H, J=2.5 Hz), 3.02 (m, 1 H), 3.88 (m, 2 H), 5.86 (t, 1 H, J=3.0 Hz), 6.52 (d, 2 H, J=7.7 Hz), 7.08 (s, 1 H), 7.32 (s, 1 H), 7.94 (d, 2 H, J=7.7 Hz).

4-[n-Propyl-(5-isopropyl-3,8,8-trimethyl-7,8-dihydronaphthalen-2-yl)lamino]benzoic acid (Compound 54)

Following General Procedure E, ethyl 4-[(5-isopropyl-3,8,8-trimethyl-7,8-dihydronaphthalen-2-yl)-n-propylamino]benzoate (Compound 51, 0.073 g, 0.18 mmol) was reacted to give 0.050 g (73%) of the title compound as a yellow solid. PNMR (300 MHz, CDCl$_3$) δ 0.98 (t, 3 H, J=7.5 Hz), 1.22 (s, 6 H), 1.24 (d, 6 H, J=7.5 Hz), 1.76 (m, 2 H), 2.08 (s, 3 H), 2.22 (d, 2 H, J=2.5 Hz), 3.01 (m, 1 H), 3.59 (s, 2 H), 5.82 (t, 1 H, J=3.0 Hz), 6.48 (d, 2 H, J=7.7 Hz), 7.06 (s, 1 H), 7.28 (s, 1 H), 7.89 (d, 2 H, J=7.7 Hz).

4-[Ethyl-(5-t-butyl-3,8,8-trimethyl-7,8-dihydronaphthalen-2-yl)amino]benzoic acid (Compound 60)

Following General Procedure E, ethyl 4-[(5-tert-butyl-3,8,8-trimethyl-7,8-dihydronaphthalen-2-yl)propylamino]benzoate (Compound 58, 0.013 g, 0.03 mmol) was reacted to give 0.012 g (100%) of the title compound as a yellow solid. PNMR (300 MHz, CDCl$_3$) δ 1.22 (s, 6 H), 1.30 (t, 3 H, J=7.5 Hz), 1.42 (s, 4 H), 2.12 (s, 3 H), 2.22 (d, 2 H, J=2.5

Hz), 3.72 (q, 2 H, J=7.5 Hz), 5.98 (t, 1 H, J=3.0 Hz), 6.52 (d, 2 H, J=7.7 Hz), 7.02 (s, 1 H), 7.60 (s, 1 H), 7.88 (d, 2 H, J=7.7 Hz). 6-Bromo- 1,4,4-trimethyl- 1,2,3,4-tetrahydro-naphthalen-1-ol (Compound 62)

Following General Procedure I which is described below in connection with the preparation of Compound 70, 6-Bromo-1-4,4-dimethyl-1,2,3,4-tetrahydro-naphthalen-1-one, (Compound 61, 1.0 g, 4.0 mmol), was reacted to give the title compound as a yellow oil which was used without purification in the next step. 6-Bromo-1-4,4-dimethyl-1,2,3,4-tetrahydro-naphthalen-1-one, (Compound 61) is available in accordance with the teachings of U.S. Pat. No. 5,489,584, incorporated herein by reference.

7-Bromo-1,1,4-trimethyl-1,2-dihydro-naphthalene (Compound 63)

Following General Procedure J which is described in connection with the preparation of Compound 71, 6-bromo-1,4,4-trimethyl-1,2,3,4-tetrahydro-naphthalen-1-ol (Compound 62, 0.81 g, 3.0 mmol), was reacted to give the title compound as an oil. PNMR (300 MHz, CDCl$_3$) δ 1.24 (s, 6 H), 2.03 (s, 3 H), 2.17 (d, 2 H, J=4.5 Hz), 5.77 (t, 1 H, J=4.5 Hz), 7.09 (d, 1 H, J=8.2 Hz), 7.30 (dd, 1 H, J=2.1 & 8.2 Hz), 7.40 (d, 1 H, J=2.1 Hz).

5,8,8-Trimethyl-7,8-dihydro-naphthalen-2-yl-amine (Compound 64)

Following General Procedure K which is described in connection with the preparation of Compound 72, 7-bromo-1,1,4-trimethyl-1,2-dihydro-naphthalene (Compound 63, 0.54 g, 2.1 mmol), was reacted to give the intermediate imine which was hydrolyzed using 10% HCl in tetrahydrofuran to give the title compound as an oil. PNMR (300 MHz, CDCl$_3$) δ 1.24 (s, 6 H), 2.03 (s, 3 H), 3.68 (s, 2 H, NH), 5.59 (t, 1 H, J=4.5 Hz), 6.49 (dd, 1 H, J=2.3 & 8.2 Hz), 6.69 (d, 1 H, J=2.3 Hz), 7.09 (d, 1 H, J=8.2 Hz).

4-(5,8,8-Trimethyl-7,8-dihydro-naphthalen-2-yl-amino)-benzoic acid ethyl ester (Compound 65)

General Procedure L To a solution of 5,8,8-trimethyl-7,8-dihydro-naphthalen-2-yl-amine (Compound 64, 0.33 g, 1.8 mmol) and ethyl 4-bromobenzoate (0.52 g, 2.3 mmol) in 10.0 mL of toluene while stirring under argon were added cesium carbonate (0.89 g, 2.7 mmol), tris(dibenzylideneacetone)dipalladium(0) (Pd$_2$(dba)$_3$, 33 mg, 0.04 mmol) and bis(diphenylphosphino)-1,1'-binaphthyl (BINAP, 47 mg, 0.08 mmol) consecutively. The reaction was then heated at 100° C. for 24 h. The reaction was then cooled to room temperature, diluted with water and extracted 2 times with ethyl ether. The combined organic extracts were washed with brine, dried over MgSO$_4$, filtered, and the solvents were removed in vacuo. The crude product was purified by silica gel chromatography (10% ethyl acetate in hexanes) to give the title compound as a yellow solid. PNMR (300 MHz, CDCl$_3$) δ 1.28 (s, 6 H), 1.38 (t, 3 H, J=7.1 Hz), 2.06 (s, 3 H), 2.19 (d, 2 H, J=4.3 Hz), 4.35 (q, 2 H J=7.1 Hz), 5.68 (t, 1 H, J=4.3 Hz), 6.04 (s 1 H, NH), 6.98 (overlapping d & dd, 3 H), 7.11 (d, 1 H, J=2.3 Hz), 7.21 (d, 1 H, J=8.2 Hz), 7.93 (d, 2 H, J=8.8 Hz).

4-Methyl-(5,8,8-trimethyl-7,8-dihydro-naphthalen-2-yl)-amino]-benzoic acid ethyl ester (Compound 66)

General Procedure M To a solution of 4-(5,8,8-trimethyl-7,8-dihydro-naphthalen-2-ylamino)-benzoic acid ethyl ester (Compound 65, 31 mg, 0.09 mmol) in a 10% acetic acid in acetonitrile solution (1.0 mL) and 1.0 mL of ether were added formaldehyde (0.10 mL, 3.60 mmol) and then sodium cyanoborohydride (14 mg, 0.22 mmol) and the reaction stirred at room temperature for 1 h. 1 M aqueous NaOH was added until pH=6 and the resulting mixture was extracted twice with ethyl ether. The combined organic extracts were washed with brine, dried over Na$_2$SO$_4$, filtered, and the solvents were removed in vacuo. The crude product was purified by silica gel chromatography (10% ethyl acetate in hexanes) to give the title compound as yellow oil. PNMR (300 MHz, CDCl$_3$) δ 1.24 (s, 6 H), 1.37 (t, 3 H, J=7.1 Hz), 2.08 (s, 3 H), 2.23 (d, 2 H, J=4.4 Hz), 3.38 (s, 3 H), 4.34 (q, 2 H, J=7.1 Hz), 5.78 (t, 1 H, J=4.4 Hz), 6.79 (d, 2 H, J=9.0 Hz), 7.03 (dd, 1 H, J=2.3 & 8.2 Hz), 7.16 (d, 1 H, J=2.3 Hz), 7.28 (d, 1 H, J=8.2 Hz), 7.88 (d, 2 H, J=9.0 Hz).

4-[Methyl-(5,8,8-trimethyl-7,8-dihydro-naphthalen-2-yl)-amino]-benzoic acid (Compound 67)

General Procedure N A solution of 4-[methyl-(5,8,8-trimethyl-7,8-dihydro-naphthalen-2-yl)-amino]-benzoic acid ethyl ester (Compound 66, 12 mg, 0.03 mmol) in 3.0 mL of ethanol was treated with 0.55 M KOH (1.0 mL). The solution was heated to 40 ° C. and stirred for 20 h. The solution was cooled and concentrated under reduced pressure. The residue was diluted with water, acidified with 10% HCl, and extracted twice with ether. The combined organic extracts were washed with brine, dried over MgSO$_4$, filtered, and the solvents were removed in vacuo to give the title compound as a solid.

4-[Ethyl-(5,8,8-trimethyl-7,8-dihydro-naphthalen-2-yl)-amino]-benzoic acid ethyl ester (Compound 68)

Following General Procedure M, 4-(5,8,8-trimethyl-7,8-dihydro-naphthalen-2-ylamino)-benzoic acid ethyl ester (Compound 65, 38 mg, 0.11 mmol), was reacted to with acetaldehyde to give the title compound as a yellow oil. PNMR (300 MHz, CDCl$_3$) δ 1.22 (s, 6 H), 1.26 (t, 3 H, J=7.1 Hz), 1.36 (t, 3 H, J=7.1 Hz), 2.08 (s, 3 H), 2.22 (d, 2 H, J=4.3 Hz), 3.80 (q, 2 H, J=7.1 Hz), 4.32 (q, 2 H, J=7.1 Hz), 5.76 (t, 1 H, J=4.3 Hz), 6.70 (d, 2 H, J=9.0 Hz), 7.00 (dd, 1 H, J=2.3 & 8.2 Hz), 7.12 (d, 1 H, J=2.3 Hz), 7.27 (d, 1 H, J=8.2 Hz), 7.84 (d, 2 H, J=9.0 Hz).

4-[Ethyl-(5,8,8-trimethyl-7,8-dihydro-naphthalen-2-yl)-amino]-benzoic acid (Compound 69)

Following General Procedure N, 4-[ethyl-(5,8,8-trimethyl-7,8-dihydro-naphthalen-2-yl)-amino]-benzoic acid ethyl ester (Compound 68, 30 mg, 0.08 mmol), was hydrolyzed with subsequent recrystallization in ethanol to give the title compound as light crystals. PNMR (300 MHz, d$^6$ acetone) δ 1.22 (s, 6 H), 1.24 (overlapping s & t), 2.08 (s, 3 H), 2.22 (d, 2 H, J=4.5 Hz), 3.86 (q, 2 H, J=7.1 Hz), 5.80 (t, 1 H, J=4.5 Hz), 6.78 (d, 2 H, J=9.1 Hz), 7.08 (dd, 1 H, J=2.2 & 8.2 Hz), 7.22 (d, 1 H, J=2.2 Hz), 7.35 (d, 1 H, J=8.2 Hz), 7.83 (d, 2 H, J=9.1 Hz).

6-Bromo-1-ethyl-4,4-dimethyl-1,2,3,4-tetrahydro-naphthalen-1-ol (Compound 70)

General Procedure I To a suspension of cerium(III) chloride (CeCl$_3$, 2.39 g, 9.7 mmol) in 8.0 mL of tetrahydrofuran stirring under argon for 2.5 h and then cooled to 0° C., was added ethylmagnesium bromide (3 M in ether, 6.50 mL, 19.5 mmol) and the reaction stirred from 0 ° C. to room temperature for 1 h. A solution of 6-bromo-1-4,4-dimethyl-1,2,3,4-tetrahydro-naphthalen-1-one (Compound 61, 0.89 g, 3.5 mmol) in 8.0 mL of ether was added and the reaction stirred for 3 h. The reaction was then cooled to room temperature, diluted with water and with 10% HCl and thereafter extracted twice with ethyl ether. The combined organic extracts were washed with brine, dried over MgSO$_4$, filtered, and the solvents were removed in vacuo to give the title compound as a yellow oil.
PNMR (300 MHz, CDCl$_3$) δ 0.90 (t, 3 H, J=7.5 Hz), 1.26 (s, 3 H), 1.29 (s, 3 H), 1.65–2.09 (m, 6 H), 3.75 (t, 1 H, J=6.6 Hz), 7.30 (dd, 1 H, J=2.1 & 8.5 Hz), 7.39 (d, 1 H, J=8.5 Hz), 7.41 (d, 1 H, J=2.1 Hz).

7-Bromo-4-ethyl-1,1-dimethyl- 1,2-dihydro-naphthalene (Compound 71)

General Procedure J To a solution 6-bromo-1-ethyl-4,4-dimethyl-1,2,3,4-tetrahydro-naphthalen-1-ol (Compound 70, 1.03 g, 3.6 mmol) in 30.0 mL of benzene stirring under argon was added p-toluenesulfonic acid (pTSA, 0.42 g, 2.2 mmol) and the reaction mixture was refluxed for 3 h. The reaction was then cooled to room temperature, diluted with water and extracted twice with ethyl ether. The combined organic extracts were washed with brine, dried over $MgSO_4$, filtered, and the solvents were removed in vacuo. The crude product was purified by silica gel chromatography (100% hexanes) to give the title compound as a clear oil.
PNMR (300 MHz, $CDCl_3$) δ 1.14 (t, 3 H, J=7.4 Hz), 1.23 (s, 6 H), 2.17 (d, 2 H, J=4.6 Hz), 2.43 (q, 2 H J=7.4 Hz), 5.77 (t, 1 H, J=4.6 Hz), 7.13 (d, 1 H, J=8.3 Hz), 7.30 (dd, 1 H, J=2.1 & 8.3 Hz), 7.41 (d, 1 H, J=2.1 Hz).

5-Ethyl-8,8-dimethyl-7,8-dihydro-naphthalen-2-yl-amine (Compound 72)

General Procedure K To a solution of 7-bromo-4-ethyl-1,1-dimethyl-1,2-dihydronaphthalene (Compound 71, 0.33 g, 1.8 mmol) and benzophenone imine (0.52 g, 2.3 mmol) in 10.0 mL of toluene stirring under argon was added sodium-t-butoxide (0.89 g, 2.7 mmol), tris(dibenzylideneacetone) dipalladium(0) ($Pd_2(dba)_3$, 33 mg, 0.04 mmol) and 2,2'-bis (diphenylphosphino)-1,1'-binaphthyl (BINAP, 47 mg, 0.08 mmol) consecutively. The reaction mixture was then heated at 80° C. for 3 h., thereafter was cooled to room temperature, diluted with ether, and filtered. The filtrate was then concentrated in vacuo and the crude product was purified by silica gel chromatography (10% ethyl acetate in hexanes) to give the intermediate imine as a yellow oil The resulting oil was then dissolved in 10.0 mL of methanol. To this was added sodium acetate (0.18 g, 2.1 mmol) and hydroxylamine hydrochloride (0.11 g, 1.6 mmol) and the reaction mixture was stirred for 45 min. The mixture was then partially concentrated in vacuo, diluted with 10% aqueous sodium hydroxide and extracted twice with methylene chloride. The combined organic extracts were washed with brine, dried over $Na_2SO_4$, filtered, and the solvents were removed in vacuo. The crude product was purified by silica gel chromatography (10% ethyl acetate in hexanes) to give the title compound as a clear oil.
PNMR (300 MHz, $CDCl_3$) δ 1.13 (t, 3 H, J=7.4 Hz), 1.19 (s, 6 H), 2.12 (d, 2 H, J=4.5 Hz), 2.41 (q, 2 H J=7.4 Hz), 3.64 (s, 2 H, NH, 5.56 (t, 1 H, J=4.5 Hz), 6.50 (dd, 1 H, J=2.4 & 8.2 Hz), 6.67 (d, 1 H, J=2.1 Hz), 7.13 (d, 1 H, J=8.3 Hz).

4-(5-Ethyl-8,8-dimethyl-7,8-dihydro-naphthalen-2-ylamino)-benzoic acid ethyl ester (Compound 73)

Following General Procedure L, 5-ethyl-8,8-dimethyl-7,8-dihydro-naphthalen-2-ylamine (Compound 72, 0.17 g, 0.85 mmol), was reacted with ethyl 4-bromobenzoate to give the title compound as a yellow solid.
PNMR (300 MHz, $CDCl_3$) δ 1.18 (t, 3 H, J=7.3 Hz), 1.23 (s, 6 H), 1.39 (t, 3 H, J=7.1 Hz), 2.17 (d, 2 H, J=4.0 Hz), 2.46 (d, 2 H, J=7.3 Hz), 4.34 (q, 2 H J=7.1 Hz), 5.70 (t, 1 H, J=4.0 Hz), 6.07 (s 1 H, NH), 7.00–7.03 (overlapping d & dd, 3 H), 7.11 (s, 1 H), 7.25 (d, 1 H, J=8.6 Hz), 7.93 (d, 2 H, J=8.6 Hz).

4-[Ethyl-(5-ethyl-8,8-dimethyl-7,8-dihydro-naphthalen-2-yl)-amino]-benzoic acid ethyl ester (Compound 74). Following General Procedure D, 4-(5-Ethyl-8,8-dimethyl-7,8-dihydro-naphthalen-2-ylamino)-benzoic acid ethyl ester (Compound 73), (0.13 g, 0.38 mmol) was reacted to give the title compound as a solid.
PNMR ($CDCl_3$): δ 1.19 (t, J=7.4 Hz, 3 H), 1.22 (s, 6 H), 1.26 (t, J=7.1 Hz, 3 H), 1.36 (t, J=7.1 Hz, 3 H), 2.21 (d, J=4.5 Hz, 2 H), 2.42 (q, J=7.3 Hz, 2 H), 2.489 (q, J=7.4 Hz, 2 H), 3 80 (q, J=7.1 Hz, 2 H), 4.316 (q, J=7.1 Hz, 2 H), 5.76 (t, J=4.5 Hz, 1 H), 6.71 (d, J=8.9 Hz, 2 H), 6.99 (dd, J=2.2, 8.2 Hz, 1 H), 7.12 (d, J=2.23 Hz, 1 H), 7.30 (d, J=8.2 Hz, 1 H), 7.84 (d, J=8.9 Hz, 2 H).

4-[Ethyl-(5-ethyl-8,8-dimethyl-7,8-dihydro-naphthalen-2-yl)-amino]-benzoic acid (Compound 75). Following General Procedure E, 4-[Ethyl-(5-ethyl-8,8-dimethyl-7,8-dihydro-naphthalen-2-yl)-amino]-benzoic acid ethyl ester (Compound 74), (88 mg, 0.23 mmol) was reacted to give the title compound as a solid. PNMR (δ6 acetone) δ 1.18 (t, J=7.3 Hz, 3 H), 1.24 (s, 6 H), 1.25 (t, J=7.1 Hz, 3 H), 2.22 (d, J=4.5 Hz, 2 H), 2.53 (q, J=7.3 Hz, 2 H), 3.87 (q, J=7.1 Hz, 2 H), 5.80 (t, J=4.5 Hz, 1 H), 6.79 (d, J=9.2 Hz, 2 H), 7.08 (dd, J=2.2, 8.1 Hz, 1 H), 7.23 (d, J=2.2 Hz, 1 H), 6-Bromo-1-isopropyl-4,4-dimethyl- 1,2,3,4-tetrahydro-naphthalen-1-ol (Compound 76)

Following General Procedure I, 6-bromo-1-4,4-dimethyl-1,2,3,4-tetrahydro-naphthalen 1-one, (Compound 61, 0.95 g, 3.7 mmol), was reacted with n-propylmagnesium bromide to give the title compound as a yellow oil.
PNMR (300 MHz, $CDCl_3$) δ 0.95 (d, 6 H, J=6.8 Hz), 1.10–1.30 (2s, 6 H), 1.70–2.05 (m, 4 H), 2.33 (p, 1 H J=6.8 Hz), 7.30 (dd, 1 H, J=2.1 & 8.5 Hz), 7.38 (d, 1 H, J=8.5 Hz),7.44 (d, 1 H, J=2.1 Hz).

7-Bromo-4-isopropyl-1,1-dimethyl-1,2-dihydro-naphthalene (Compound 77)

Following General Procedure J, 6-bromo- 1-isopropyl-4,4-dimethyl-1,2,3,4-tetrahydro-naphthalen-1-ol (Compound 76, 0.85 g, 2.9 mmol), was reacted with ethyl 4-bromobenzoate to give the title compound as a yellow oil.
PNMR (300 MHz, $CDCl_3$) δ 1.15 (d, 6 H, J=6.7 Hz), 1.23 (s, 6 H), 2.17 (d, 2 H, J=4.6 Hz), 2.91 (p, 1 H J=6.7 Hz), 5.79 (t, 1 H, J=4.6 Hz), 7.19 (d, 1 H, J=8.4 Hz), 7.32 (dd, 1 H, J=2.1 & 8.4 Hz), 7.42 (d, 1 H, J=2.1 Hz).

5-Isopropyl-8,8-dimethyl-7,8-dihydro-naphthalen-2-ylamine (Compound 78)

Following General Procedure K, 7-bromo-4-isopropyl-1,1-dimethyl- 1,2-dihydro-naphthalene (Compound 77, 0.57 g, 2.0 mmol), was reacted to give the intermediate imine which was hydrolyzed using 10% HCl in tetrahydrofuran to give the title compound as an oil.
PNMR (300 MHz, $CDCl_3$) δ 1.13 (d, 6 H, J=6.6 Hz), 1.19 (s, 6 H), 2.12 (d, 2 H, J=4.6 Hz), 2.88 (p, 1 H J=6.6 Hz), 5.58 (t, 1 H, J=4.6 Hz), 6.51 (d, 1 H, J=8.2 Hz), 6.67 (s, 1 H), 7.15 (d, 1 H, J=8.2 Hz).

4-(5-Isopropyl-8,8-dimethyl-7,8-dihydro-naphthalen-2-ylamino)-benzoic acid ethyl ester (Compound 79)

Following General Procedure L, 5-isopropyl-8,8-dimethyl-7,8-dihydro-naphthalen-2-ylamine (Compound 78, 80 mg, 0.37 mmol), was reacted to give the title compound as a yellow solid.
PNMR (300 MHz, $CDCl_3$) δ 1.18 (d, 6 H, J=6.8 Hz), 1.23 (s, 6 H), 1.39 (t, 3 H, J=7.1 Hz), 2.20 (d, 2 H, J=4.6 Hz), 2.95 (p, 1 H, J=6.8 Hz), 4.36 (q, 2 H, J=7.1 Hz), 5.73 (t, 1 H, J=4.6 Hz), 6.05 (s 1 H, NH), 6.99–7.04 (overlapping d & dd, 3 H), 7.12 (d, 1 H, J=2.5 Hz), 7.31 (d, 1 H, J=8.4Hz), 7.84 (d, 2 H, J=8.8 Hz).

4-[Ethyl-(5-isopropyl-8,8-dimethyl-7,8-dihydro-naphthalen-2-yl)-amino]-benzoic acid ethyl ester (Compound 80)

Following General Procedure M, 4-(5-isopropyl-8,8-dimethyl-7,8-dihydro-naphthalen-2-ylamino)-benzoic acid ethyl ester (Compound 79, 10 mg, 0.06 mmol), was reacted with acetaldehyde to give the title compound as a yellow oil.
PNMR (300 MHz, $CDCl_3$) δ 1.20 (overlapping d & s, 12 H), 1.26 (t, 3 H, J=7.0 Hz), 1.35 (t, 3 H, J=7.1 Hz), 2.22 (d, 2 H, J=4.4 Hz), 2.96 (p, 1 H, J=6.0 Hz), 3.81 (q, 2 H, J=7.1

Hz), 4.31 (q, 2 H, J=7.1 Hz), 5.78 (t, 1 H, J=4.4 Hz), 6.70 (d, 2 H, J=9.0 Hz), 7.00 (dd, 1 H, J=2.3 & 8.3 Hz), 7.12 (d, 1 H, J=2.3 Hz), 7.35 (d, 1 H, J=8.3 Hz), 7.84 (d, 2 H, J=9.0 Hz).

4-[Ethyl-(5-isopropyl-8,8-dimethyl-7,8-dihydro-naphthalen-2-yl)-amino]-benzoic acid (Compound 81)

Following General Procedure N, 4-[Ethyl-(5-isopropyl-8,8-dimethyl-7,8-dihydro-naphthalen-2-yl)-amino]-benzoic acid ethyl ester (Compound 80, 6 mg, 0.01 mmol), was hydrolyzed to give the title compound as light crystals.
PNMR (300 MHz, d⁶ acetone) δ 1.04–1.14 (overlapping t, d & s, 15 H), 2.08 (d, 2 H, J=4.3 Hz), 2.89 (p, 1 H, J=6.5 Hz), 3.74 (q, 2 H, J=7.1 Hz), 5.68 (t, 1 H, J=4.3 Hz), 6.66 (d, 2 H, J=9.0 Hz), 6.95 (dd, 1 H, J=2.3 & 8.3 Hz), 7.09 (d, 1 H, J=2.3 Hz), 7.32 (d, 1 H, J=8.3 Hz), 7.70 (d, 2 H, J=9.0 Hz).

8-t-Butyl-5,5-dimethyl-5,6-dihydronaphthalene-2-ylamine (Compound 83)

A mixture of 7-bromo-1-(1,1-dimethylethyl)-3,4-dihydro-4,4-dimethylnaphthalene (Compound 82, 1.4 g, 4.7 mmol), benzophenoneimine (1.19 g, 6.1 mmol), 2,2'-bis(diphenylphosphino)-1,1'-binaphthyl (147 mg, 0.24 mmol), tris(dibenzylideneacetone)dipalladium (75 mg, 0.08 mmol) and sodium t-butoxide (672 mg, 7 mmol) in toluene (15 mL) was heated to 95 °C. for 16 h under argon atmosphere. Compound 82 is available in accordance with the teachings of U.S. Pat. No. 5,763,635, incorporated herein by reference. After heating the resulting solid was removed by filtration, and was purified by silicagel flash chromatography to obtain the imine adduct. The imine adduct was dissolved in THF (15 mL), 10% HCl (2 mL) and stirred for 15 min at ambient temperature. The mixture was diluted with dichloromethane (60 mL) washed with 10% NaHCO₃, brine, dried and solvent removed. Silica gel flash chromatography gave the title compound:
PNMR (CDCl₃): δ 1.19 (s, 6 H), 1.35 (s, 9 H), 2.10 (d, J=5.0 Hz, 2 H), 5.95 (t, J=5.0 Hz, 1 H), 6.60 (dd, J=2.4, 8.2 Hz, 1 H), 7.09 (d, J=2.4 Hz, 1 H), 7.12 (d, J=8.2 Hz, 1 H).

Ethyl 4-(8-t-butyl-5,5-dimethyl-5,6-dihydronaphthalen-2-ylamino)-benzoate (Compound 84)

A mixture of 8-t-butyl-5,5-dimethyl-5,6-dihydronaphthalene-2-ylamine ((Compound 83, 800 mg, 3.5 mmol), ethyl-4-iodo-benzoate 1.07 g, 3.9 mmol), 2,2'-bis(diphenylphosphino)-1,1'-binaphthyl (35 mg, 0.05 mmol), tris(dibenzylideneacetone)dipalladium (21 mg, 0.02 mmol) and cesium carbonate (1.5 g, 17.5 mmol) in toluene (25 mL) was heated to 95° C. for 16 h under argon atmosphere. After heating was discontuned the resulting solid was filtered off and the crude material was purified by silica gel flash chromatography to obtain the title compound.
PNMR (CDCl₃): δ 1.25 (s, 6 H), 1.35 (s, 9 H), 1.39 (t, J=7.2, 3 H), 2.17 (d, J=4.9 Hz, 2 H), 4.35 (q, J=7.2 Hz, 2 H), 6.01 (t, J=4.9 Hz, 2 H), 6.96 (d, J=8.4 Hz, 2 H), 7.00 (dd, J=2.2, 8.3 Hz, 1 H), 7.29 (d, J=8.3 Hz, 1 H), 7.50 (d, J=2.2 Hz, 1 H), 7.93 (d, J=8.4 Hz, 2 H).

Ethyl 4-[(8-t-butyl-5,5-dimethyl-5,6-dihydronaphthalen-2-yl)ethylamino]-benzoate (Compound 85)

A mixture of ethyl 4-(8-t-butyl-5,5-dimethyl-5,6-dihydronaphthalen-2-ylamino)-benzoate (Compound 84, 250 mg, 0.7 mmol), K₂CO₃ (1.4 g), ethyl iodide (2 g, 12.8 mmol) and dimethylacetamide (5 mL) was heated to 75° C. in a sealed tube for 7 days. The mixture was diluted with ether (70 mL), washed with brine, dried and the solvent was removed. Silica gel flash chromatography gave the title compound.
PNMR (CDCl₃): δ 1.26 (s, 6 H), 1.27 (t, J=7.0 Hz, 3 H), 1.29 (s, 9 H), 1.36 (t, J=7.1 Hz, 3 H), 2.18 (d, J=4.9 Hz, 2 H), 3.80 (q, J=7.0 Hz, 2 H), 4.32 (q, J=7.1 Hz, 2 H), 5.99 (t, J=4.9 Hz, 1 H), 6.68 (d, J=9.0 Hz, 2 H), 6.99 (dd, J=2.2, 8.2 Hz, 1 H), 7.33 (d, J=8.2 Hz, 1 H), 7.44 (d, J=2.2 Hz, 1 H), 7.85 (d, J=9.0 Hz, 2 H).

Ethyl 4-[(8-t-butyl-5,5-dimethyl-5,6-dihydronaphthalen-2-yl)-n-propylamino)]-benzoate (Compound 86)

A mixture of ethyl 4-(8-t-butyl-5,5-dimethyl-5,6-dihydronaphthalen-2-ylamino)-benzoate (Compound 84, 160 mg, 0.4 mmol), K₂CO₃ (900 mg), n-propyl iodide (5 mL) and dimethylacetamide (5 mL) was heated to 75° C. in a sealed tube for 7 days. The mixture was diluted with ether (70 mL), washed with brine, dried and the solvent was removed. Silicagel flash chromatography gave the title compound. PNMR (CDCl₃): δ 0.95 (t, J=7.0 Hz, 3 H), 1.27 (s, 6 H), 1.29 (s, 9 H), 1.36 (t, J=7.1 Hz, 3 H), 1.75 (m, 2 H), 2.19 (d, J=4.9 Hz, 2 H), 3.68 (t, J=7.0 Hz, 2 H), 4.34 (q, J=7.1 Hz, 2 H), 6.00 (t, J=4.9 Hz, 1 H), 6.68 (d, J=9.0 Hz, 2 H), 6.99 (dd, J=2.2, 8.2 Hz, 1 H), 7.34 (d, J=8.2 Hz, 1 H), 7.47 (d, J=2.2 Hz, 1 H), 7.86 (d, J=9.0 Hz, 2 H).

Ethyl 4-[(8-t-butyl-5,5-dimethyl-5,6-dihydronaphthalen-2-yl)(prop-2-en-yl)amino]-benzoate (Compound 87)

A mixture of ethyl 4-(8-t-butyl-5,5-dimethyl-5,6-dihydronaphthalen-2-ylamino)-benzoate (Compound 84, 170 mg, 0.45 mmol), K₂CO₃ (900 mg), allyl bromide (1 mL) and dimethylacetamide (5 mL) was heated to 75° C. in a sealed tube for 7 days. The mixture was diluted with ether (70 mL), washed with brine, dried and the solvent was removed. Silica gel flash chromatography gave the title compound.
PNMR (CDCl₃): δ 1.25 (s, 6 H), 1.29 (s, 9 H), 1.36 (t, J=7.0 Hz, 3 H), 2.18 (d, J=4.9 Hz, 2 H), 4.32 (q, J=7.0 Hz, 2 H), 4.38 (d, J=4.7 Hz, 2 H), 5.24 (d, J=14.0 Hz, 1 H), 5.30 (d, J=14.0 Hz, 1 H), 5.95 (dt, J=4.7, 14.0 Hz, 1 H), 5.99 (t, J=4.9 Hz, 1 H), 6.75 (d, J=9.0 Hz, 2 H), 7.45 (dd, J=2.2, 8.2 Hz, 1 H), 7.50 (d, J=2.2 Hz, 1 H), 7.86 (d, J=9.0 Hz, 2 H).

4-[(8-t-Butyl-5,5-dimethyl-5,6-dihydronaphthalen-2-yl)ethylamino]-benzoic acid (Compound 88)

A solution of ethyl 4-[(8-t-butyl-5,5-dimethyl-5,6-dihydronaphthalen-2-yl)ethylamino)]-benzoate (Compound 85, 120 mg, 0.3 mmol), KOH in water (1 M, 1 mL, 1 mmol), THF (3 mL), MeOH (3 mL) was heated to 70° C. for 12 h. The reaction was acidified with 10% HCl, extracted with dichloromethane (3×30 mL), washed with brine, dried and the solvent was removed. The product was recrystallized from acetone.
PNMR (CDCl₃): δ 1.26 (s, 6 H),1.28 (t, J=7.0 Hz, 3 H), 1.30 (s, 9 H), 2.18 (d, J=4.9 Hz, 2 H), 3.81 (q, J=7.0 Hz, 2 H), 5.60 (t, J=4.9 Hz, 1 H), 6.68 (d, J=9.0 Hz, 2 H), 6.99 (dd, J=2.2, 8.2 Hz, 1 H), 7.35 (d, J=8.2 Hz, 1 H), 7.44 (d, J=2.2 Hz, 1 H), 7.90 (d, J=9.0 Hz, 2 H).

4-[(8-t-Butyl-5,5-dimethyl-5,6-dihydronaphthalen-2-yl)-n-propylamino)]-benzoic acid (Compound 89)

A solution of ethyl 4-[(8-t-butyl-5,5-dimethyl-5,6-dihydronaphthalen-2-yl)-n-propylamino)]-benzoate (Compound 86, 25 mg, 0.06 mmol), KOH in water (1 M, 0.2 mL, 0.2 mmol), THF (2 mL), MeOH (2 mL) was heated to 70°C. for 12 h. The reaction was acidified with 10% HCl, extracted with dichloromethane (3×30 mL), washed with brine, dried and the solvent was removed. The product was recrystallized from acetone.
PNMR (Acetone-D₆): δ 0.95 (t, J=7.4 Hz, 3 H), 1.24 (s, 6 H), 1.28 (s, 9 H), 1.68–1.79 (m, 2 H), 2.16 (d, J=5.0 Hz, 2 H), 3.73 (t, J=6.0 Hz, 2 H), 6.04 (t, J=5.0 Hz, 1 H), 6.73 (d, J=9.0 Hz, 2 H), 7.08 (dd, J=2.2, 8.2 Hz, 1 H), 7.42 (d, J =8.2 Hz, 1 H), 7.48 (d, J=2.2 Hz, 1 H), 7.80 (d, J=9.0 Hz, 2 H).

4-[(8-t-Butyl-5,5-dimethyl-5,6-dihydronaphthalen-2-yl)(prop-2-en-yl)amino]-benzoic acid (Compound 90)

A solution of ethyl 4-[(8-t-butyl-5,5-dimethyl-5,6-dihydronaphthalen-2-yl)(prop-2-en-yl)amino]-benzoate (Compound 87, 80 mg, 0.2 mmol), KOH in water (1 M, 1 mL, 1 mmol), THF (3 mL), MeOH (2 mL) was heated to 70° C. for 12 h. The reaction was acidified with 10% HCl, extracted with dichloromethane (3×30 mL), washed with brine, dried and solvent removed. The product was recrystallized from acetone.
PNMR (Acetone-$D_6$): δ 1.24 (s, 6 H), 1.28 (s, 9 H), 2.16 (d, J=5.0 Hz, 2 H), 4.45 (d, J=6.0 Hz, 2 H), 5.20 (dd, J=1.0, 12 Hz, 1 H), 5.28 (dd, J=1.0, 16 Hz, 1 H), 5.98 (dt, J=6.0, 12 Hz, 1 H), 6.03 (t, J=5.0 Hz, 1 H), 6.77 (d, J=9.0 Hz, 2 H), 7.12 (dd, J=2.2, 8.2 Hz, 1 H), 7.40 (d, J=8.2 Hz, 1 H), 7.54 (d, J=2.2 Hz, 1 H), 7.82 (d, J=9.0 Hz, 1 H).

7-Methoxy-1,1-dimethyl-1,2,3,4-tetrahydronaphthalene

To a solution of $TiCl_4$ 1 M in $CH_2Cl_2$ (240 mL, 0.24 mol) at −40° C. under the argon atmosphere was added a solution of $Me_2Zn$ 2 M in toluene (180 mL, 0.36 mol), and the resulting dark brown cloudy mixture was stirred for 15 min. A solution of 7-methoxy-1-tetralone (21.1 g, 0.12 mol) and 50 mL of dichloromethane was then added, and the temperature was raised to 0° C., then slowly to room temperature. After 5 h, the reaction was cooled down to 0° C., quenched with methanol until no more bubbling was observed. Saturated $NH_4Cl$ was added, and the reaction mixture was extracted three times with ethyl acetate. The combined extracts were washed with brine, dried over $MgSO_4$, and filtered. The solvent was removed to give 20.0 g (88%) of the title compound as a dark oil.
PNMR (300 MHz, $CDCl_3$) 1.27 (2, 6 H), 1.68 (m, 2 H), 1.76 (m, 2 H), 2.70 (t, 2 H, J=5.8 Hz), 3.78 (s, 3 H), 6.65 (d, 1 H, J=8.5 Hz), 6.86 (s, 1 H), 6.96 (d, 1 H, J=8.2 Hz).

6-Bromo-7-methoxy-1,1-dimethyl-1,2,3,4-tetrahydronaphthalene (Compound 91)

To a solution of 7-methoxy-1,1-dimethyl-1,2,3,4-tetrahydronaphthalene (0.99 g, 5.2 mmol) in glacial acetic acid (30 mL) at 0° C. was added slowly bromine (0.5 mL, 10.4 mmol), and the resulting solution was allowed to slowly warm to room temperature while being stirred. After 48 h, the reaction mixture was quenched with a saturated solution of $Na_2S_2O_3$ and extracted with ethyl acetate, and the combined extracts were dried ($MgSO_4$). The solvent was removed under reduced pressure, and the residue was purified by flash column (hexane:ethyl acetate=95:5) to afford 0.5556g (40%) of the title compound as a clear oil.
PNMR (300 MHz, $CDCl_3$) 1.29 (s, 6 H), 1.63 (t, 2 H, J=5.3 Hz), 1.77 (m, 2 H), 2.68 (t, 2 H, J=6.1 Hz), 3.88 (s, 3 H), 7.20 (s, 1 H), 6.84 (s, 1 H).

7-Bromo-6-methoxy-4,4-dimethyl-3,4-dihydro-2H-naphthalen-1-one (Compound 92)

To a solution of 6-bromo-7-methoxy- 1,1-dimethyl-1,2,3,4-tetrahydronaphthalene (Compound 92, 0.56 g, 2.1 mmol) in glacial acetic acid (4 mL) at 0° C. was added a cold solution of $CrO_3$ in 1 mL of glacial acetic acid and 1 mL of water, and the resulting mixture was allowed to slowly warm to room temperature while being stirred. After 24 h, the reaction mixture was diluted with water and extracted with ethyl acetate. The combined extracts were washed with 2 N NaOH, brine, dried over $MgSO_4$, and filtered. The solvent was removed under reduced pressure to afford 0.49 g (83%) of the title compound as a white solid.
PNMR (300 MHz, $CDCl_3$) 1.25 (s, 6 H), 1.92 (t, 2 H, J=6.8 Hz), 2.58 (t, 2 H, J=6.8 Hz), 3.90 (s, 3 H), 6.82 (s, 1 H), 8.08 (s, 1 H).

6-Bromo-7-methoxy-1,1,4-trimethyl-1,2-dihydronaphthalene (Compound 93)

Following General Procedure A 7-bromo-6-methoxy-4,4-dimethyl-3,4-dihydro-2H-naphthalen-1-one (Compound 92, 1.0 g, 3.5 mmol) was reacted with MeMgBr to give 0.93 g (94%) of the title compound as a yellow solid.

PNMR (300 MHz, $CDCl_3$) 1.25 (s, 6 H), 2.03 (s, 3 H), 2.18 (d, 2 H, J=4.5 Hz), 3.95 (s, 3 H), 5.68 (m, 1 H), 6.90 (s, 1 H), 7.42 (s, 1 H).

3-Bromo-5,8,8-trimethyl-7,8-dihydronaphthalen-2-ol (Compound 96)

To a suspension of sodium hydride 60% w/w (0.12 g, 3.0 mmol) in 10 mL of DMF under the argon atmosphere was added slowly ethanethiol 98% (0.2 mL, 3.0 mmol), and the resulting solution was stirred for 15 min. A solution 6-bromo-7-methoxy-1,1,4-trimethyl-1,2-dihydronaphthalene (Compound 93, 0.24 g, 0.84 mmol) in 2 mL of DMF was added, and the reaction mixture was refluxed for 4 h, then cooled to room temperature, acidified with 2 N HCl, diluted with water and extracted with ethyl acetate. The combined extracts were washed with brine, dried over $MgSO_4$, and filtered. The solvent was removed to afford 0.23 g (100%) of the title compound as a clear oil.
PNMR (300 MHz, $CDCl_3$) 1.20 (s, 6 H), 2.02 (s, 3 H), 2.18 (d, 2 H, J=4.8 Hz), 5.68 (m, 1 H), 7.02 (s, 1 H), 7.31 (s, 1 H).

6-Bromo-7-n-hexyloxy-1,1,4-trimethyl-1,2-dihydronaphthalene (Compound 99)

General Procedure O. To a solution of 3-bromo-5,8,8-trimethyl-7,8-dihydronaphthalen-2-ol (Compound 96, 0.22 g, 0.84 mmol) in THF (10 mL) at room temperature was added $K_2CO_3$, followed by 1-iodohexane, and the resulting solution was stirred at 60° C. for 16 h, then cooled to room temperature. The mixture was diluted with water and extracted with ethyl acetate. The combined extracts were washed with 2 N NaOH, brine, dried over $MgSO_4$, and filtered. The solvent was removed under reduce pressure, and the residue was purified by flash column (hexane:ethyl acetate=4:1) to afford 0.19 g (64%) of the title compound as a clear oil.
PNMR (300 MHz, $CDCl_3$) 1.22 (s, 6 H), 1.38 (m, 9 H), 2.02 (s, 3 H), 2.18 (d, 2 H, J=4.8 Hz), 3.18 (m, 4 H), 5.67 (m, 1 H), 6.86 (s, 1 H), 7.38 (s, 1 H).

Ethyl 4-(3-n-hexyloxy-5,5,8-trimethyl-5,6-dihydronaphthalen-2-ylamino)benzoate (Compound 112)

General Procedure P A solution of 6-bromo-7-n-hexyloxy-1,1,4-trimethyl-1,2-dihydronaphthalene (Compound 99, 0.31 g, 0.9 mmol), $PdCl_2(dppf)$(0.070 g, 0.09 mmol), dppf (0.050 g, 0.09 mmol), NaOtBu (0.12 g, 1.3 mmol), ethyl 4-aminobenzoate (0.22 g, 1.35 mmol) and 5 mL of toluene was flushed with argon for 10 min, then stirred at 110° C. in a sealed tube for 5 d. After the reaction mixture was cooled to room temperature, the solvent was removed, and the residue was purified by flash column chromatography (hexane:ethyl acetate=4:1) to give 0.058 g (15%) of the title compound as a yellowish oil.
PNMR (300 MHz, $CDCl_3$) 0.93 (m, 3 H), 1.27 (s, 6 H), 1.36 (m, 9 H), 1.80 (m, 2 H), 2.02 (s, 3 H), 2.19 (d, 2 H, J=4.3 Hz), 4.05 (t, 2 H, J=6.5 Hz), 4.36 (q, 2 H, J=7.1 Hz), 5.69 (m, 1 H, 6.25 (s, 1 H), 6.90 (s, 1 H), 7.05 (d, 2 H, J=8.7 Hz), 7.32 (s, 1 H), 7.95 (d, 2 H, J=8.8 Hz).

Ethyl 4-[ethyl-(3-n-hexyloxy-5,5,8-trimethyl-5,6-dihydronaphthalen-2-yl)amino]benzoate (Compound 125)

Following General Procedure D ethyl 4-(3-n-hexyloxy-5,5,8-trimethyl-5,6-dihydronaphthalen-2-ylamino)benzoate (Compound 112, 0.03 g, 0.07 mmol) was reacted with acetaldehyde and the resulting crude product, residue was purified by flash column chromatography (hexane:ethyl acetate=4:1) to afford 0.030 g (100%) of the title compound as a yellow oil.
PNMR (300 MHz, $CDCl_3$) 1.20 (m, 9 H), 1.32 (s, 6 H), 1.35 (t, 3 H, J=6.8 Hz), 1.58 (m,2 H), 2.02 (s, 3 H), 2.22 (d, 2 H, J=4.8 Hz), 3.68 (q,2 H, J=7.0 Hz), 3.92 (t, 2 H, J=6.5 Hz), 4.32 (q, 2 H, J=7.2 Hz), 5.68 (m, 1 H), 6.54 (d, 2 H, J=8.8 Hz), 6.92 (s, 1 H), 7.02 (s, 1 H), 7.82 (d, 2 H, J=9.0 Hz).

4-Ethyl-(3-n-hexyloxy-5,5,8-trimethyl-5,6-dihydronaphthalen-2-yl)amino]benzoic Acid (Compound 142)

Following General Procedure E ethyl 4-[ethyl-(3-n-hexyloxy-5,5,8-trimethyl-5,6-dihydronaphthalen-2-yl)amino]benzoate (Compound 125, 0.036 g, 0.078 mmol) was saponified with KOH to give 0.0090 g (27%) of the title compound as a yellow oil.

PNMR (300 MHz, CDCl$_3$) 1.20 (m, 9 H), 1.28 (s, 6 H), 1.58 (m, 2 H), 1.98 (s, 3 H), 2.20 (m, 2 H), 3.68 (q, 2 H, J=7.0 Hz), 3.92 (t, 2 H, J=6.5 Hz), 5.68 (m, 1 H), 6.58 (d, 2 H, J=8.8 Hz), 6.92 (s, 1 H), 7.02 (s, 1 H), 7.82 (d, 2 H, J=9.2 Hz).

6-Bromo-7-n-heptyloxy-1,1,4-trimethyl-1,2-dihydronaphthalene (Compound 100)

Following General Procedure O, 3-bromo-5,8,8-trimethyl-7,8-dihydronaphthalen-2-ol (Compound 96, 0.30 g, 1.1 mmol) was reacted to afford 0.40 g (100%) of the title compound as a yellow oil.

PNMR (300 MHz, CDCl$_3$) 1.22 (s, 6 H), 1.35 (m, 13 H), 1.82 (m, 6 H), 2.18 (d, 2 H, J=4.8 Hz), 2.31 (m, 1 H), 4.05 (t, 2 H, J=6.5 Hz), 5.68 (m, 1 H), 6.88 (s, 1 H), 7.48 (s, 1 H).

Ethyl 4-(3-n-heptyloxy-5,5,8-trimethyl-5,6-dihydronaphthalen-2-ylamino)benzoate (Compound 113)

Following General Procedure P, 6-bromo-7-n-heptyloxy-1,1,4-trimethyl-1,2-dihydronaphthalene (Compound 100, 0.40 g, 1.1 mmol) was reacted to afford 0.048 g (10%) of the title compound as a yellow oil.

PNMR (300 MHz, CDCl$_3$) 0.92 (m, 3 H), 1.27 (s, 6 H), 1.36 (m, 11 H), 1.80 (m, 2 H), 2.02 (s, 3 H), 2.19 (d, 2 H, J=4.3 Hz), 4.05 (t, J=6.5 Hz), 4.36 (q, 2 H, J=7.1 Hz), 5.69 (m, 1 H), 6.25 (s, 1 H), 6.90 (s, 1 H), 7.05 (d, 2 H, J=8.7 Hz), 7.32 (s, 1 H), 7.95 (d, 2 H, J=8.8 Hz).

Ethyl 4-[Ethyl-(3-n-heptyloxy-5,5,8-trimethyl-5,6-dihydronaphthalen-2-yl)amino]benzoate (Compound 126)

Following General Procedure D, ethyl 4-(3-n-heptyloxy-5,5,8-trimethyl-5,6-dihydronaphthalen-2-ylamino)benzoate (Compound 113, 0.024 g, 0.05 mmol) was reacted to afford 0.025 g (100%) of the title compound as a yellow solid.

PNMR (300 MHz, CDCl$_3$) 0.90 (m, 3 H), 1.20 (m, 7 H), 1.28 (s, 6 H), 1.35 (m, 4 H), 1.48 (m, 4 H), 1.98 (s, 3 H), 2.22 (m, 2 H), 3.68 (m, 2 H), 3.90 (m, 2 H), 4.30 (q, 2 H, J=7.0 Hz), 5.68 (m, 1 H), 6.54 (d, 2 H, J=8.8 Hz), 6.92 (s, 1 H), 7.02 (s, 1 H), 7.82 (d, 2 H, J=9.0 Hz).

4[Ethyl-(3-n-heptyloxy-5,5,8-trimethyl-5,6-dihydronaphthalen-2-yl)amino]benzoic acid ((Compound 143b)

Following General Procedure E, ethyl 4-[ethyl-(3-n-heptyloxy-5,5,8-trimethyl-5,6-dihydronaphthalen-2-yl)amino]benzoate (Compound 126, 0.034 g, 0.07 mmol) was reacted to afford 0.014 g (43%) of the title compound as a yellow solid.

PNMR (300 MHz, CDCl$_3$) 0.85 (m, 3 H), 1.20 (m, 11 H), 1.28 (s, 6 H), 1.58 (m, 2 H), 1.98 (s, 3 H), 2.22 (m, 2 H), 3.68 (m, 2 H), 3.90 (m, 2 H), 5.68 (m, 1 H), 6.52 (d, 2 H, J=8.8 Hz), 6.92 (s, 1 H), 7.02 (s, 1 H), 7.82 (d, 2 H, J=9.0 Hz).

7-Benzyloxy-6-bromo- 1,1,4-trimethyl-1,2-dihydronaphthalene (Compound 101)

Following General Procedure O, 3-bromo-5,8,8-trimethyl-7,8-dihydronaphthalen-2-ol (Compound 96, 0.30 g, 1.1 mmol) was reacted to afford 0.40 g (100%) of the title compound as a yellow oil. PNMR (300 MHz, CDCl$_3$) 1.18 (s, 6 H), 2.02 (s, 3 H), 2.15 (m, 2 H), 5.18 (s, 2 H), 5.68 (m, 1 H), 6.90 (s, 1 H), 7.45 (m, 6 H).

Ethyl 4-(3-benzyloxy-5,5,8-trimethyl-5,6-dihydronaphthalen-2-ylamino)benzoate (Compound 114)

Following General Procedure P, 7-benzyloxy-6-bromo-1,1,4-trimethyl-1,2-dihydronaphthalene (Compound 101, 0.40 g, 1.1 mmol) was reacted to afford 0.032 g (7%) of the title compound as a yellow oil.

PNMR (300 MHz, CDCl$_3$) 1.25 (s, 6 H), 1.40 (t, 3 H, J=6.8 Hz), 2.02 (s, 3 H),2.18 (d, 2 H, J=4.8 Hz),4.38 (q, 2 H, J=6.5 Hz),5.15 (s,2 H),5.70 (m, 1 H), 6.26 (s, 1 H), 6.98 (s, 1 H), 7.05 (d, 2 H, J=8.7 Hz), 7.40 (m, 5 H), 7.94 (d,2 H, J=8.8 Hz).

Ethyl 4-[ (3-benzyloxy-5,5,8-trimethyl-5,6-dihydronaphthalen-2-yl)ethylamino]benzoate (Compound 127)

Following General Procedure D, ethyl 4-(3-benzyloxy-5,5,8-trimethyl-5,6-dihydronaphthalen-2-ylamino)benzoate (Compound 114, 0.030 g, 0.07 mmol) was reacted to afford 0.032 g (100%) of the title compound as a yellow solid.

PNMR (300 MHz, CDCl$_3$) 1.98 (s, 3 H), 2.20 (d, 2 H, J=4.8 Hz), 3.72 (q, 2 H, J=6.8 Hz), 4.32 (q, 2 H, J=7.0 Hz), 5.02 (s, 2 H), 5.68 (m, 1 H), 6.58 (d, 2 H, J=8.8 Hz), 7.04 (s, 1 H), 7.28 (m, 5 H), 7.85 (d, 2 H, J=9.0 Hz).

4-[(3-Benzyloxy-5,5,8-trimethyl-5,6-dihydronaphthalen-2-yl)ethylamino]benzoic acid (Compound 144)

Following General Procedure E, ethyl 4-[(3-benzyloxy-5,5,8-trimethyl-5,6-dihydronaphthalen-2-yl)ethylamino]benzoate (Compound 127, 0.032 g, 0.07 mmol) was reacted to afford 0.013 g (36%) of the title compound as a yellow solid.

PNMR (300 MHz, CDCl$_3$) 1.22 (m, 3 H), 1.26 (s, 6 H), 1.98 (s, 3 H), 2.18 (d, 2 H, J=4.3 Hz), 3.72 (q, 2 H, J=6.5 Hz), 5.04 (s, 2 H), 5.68 (m, 1 H), 6.58 (d, 2 H, J=8.8 Hz), 7.02 (s, 1 H), 7.04 (s, 1 H), 7.28 (m, 5 H), 7.88 (d, 2 H, J=9.0 Hz).

Ethyl 4-[ (3-n-hexyloxy-5,5,8-trimethyl-5,6-dihydronaphthalen-2-yl)-n-propylamino]benzoate (Compound 128)

Following General Procedure P, (Compound 112, 0.030 g, 0.07 mmol) was reacted with propionaldehyde to afford 0.032 g (100%) of the title compound as a yellow oil.

PNMR (300 MHz, CDCl$_3$) 0.92 (m, 3 H), 1.20 (m, 9 H), 1.32 (s, 6 H), 1.35 (t, 3 H, J=6.8 Hz), 1.58 (m, 4 H), 2.02 (s, 3 H), 2.22 (d, 2 H, J=4.8 Hz), 3.88 (q, 2 H, J=7.0 Hz), 4.18 (t, 2 H, J=6.8 Hz), 4.58 (q, 2 H, J=6.5 Hz), 5.88 (m, 1 H), 6.68 (d, 2 H, J=8.8 Hz), 7.08 (s, 1 H), 7.18 (s, 1 H), 7.92 (d, 2 H,J=9.0 Hz).

4-[(3-n-Hexyloxy-5,5,8-trimethyl-5,6-dihydronaphthalen-2-yl)-n-propylamino]benzoic acid (Compound 145)

Following General Procedure E, ethyl 4-[(3-n-hexyloxy-5,5,8-trimethyl-5,6-dihydronaphthalen-2-yl)-n-propylamino]benzoate (Compound 128, 0.040 g, 0.08 mmol) was reacted to afford 0.010 g (27%) of the title compound as a yellow solid.

PNMR (300 MHz, CDCl$_3$) 0.90 (t, 3 H, J=6.5 Hz), 1.20 (m, 9 H), 1.30 (s, 6 H), 1.55 (m, 2 H), 1.70 (m, 2 H), 1.98 (s, 3 H), 2.20 (m, 2 H), 3.58 (t, 2 H, J=6.5 Hz), 3.90 (t, 2 H, J=6.8 Hz),5.68 (m, 1 H),6.52 (d,2 H, J=8.8 Hz), 6.92 (s, 1 H), 7.02 (s, 1 H), 7.85 (d, 2 H, J=9.3 Hz).

Ethyl 4-[(3-n-heptyloxy-5,5,8-trimethyl-5,6-dihydronaphthalen-2-yl-n-propylamino]benzoate (Compound 129)

Following General Procedure P, ethyl 4-(3-n-heptyloxy-5,5,8-trimethyl-5,6-dihydronaphthalen-2-ylamino)benzoate (Compound 113, 0.024 g, 0.05 mmol) was reacted with propionaldehyde to afford 0.026 g (100%) of the title compound as a yellow oil.

PNMR (300 MHz, CDCl$_3$) 0.90 (m, 5 H), 1.20 (m, 7 H), 1.28 (s, 6 H), 1.35 (m, 4 H), 1.58 (m, 4 H), 1.98 (s, 3 H), 2.22

(m, 2 H), 3.68 (q, 2 H, J=7.0 Hz), 3.90 (t, 2 H, J=6.8 Hz), 4.30 (q, 2 H, J=7.0 Hz), 5.68 (m, 1 H), 6.54 (d, 2 H, J=8.8 Hz), 6.92 (s, 1 H), 7.02 (s, 1 H), 7.82 (d, 2 H, J=9.0 Hz).

4-[(3-n-Heptyloxy-5,5,8-trimethyl-5,6-dihydronaphthalen-2-yl)-n-propylamino]benzoic acid (Compound 146)

Following General Procedure E, ethy 4-[(3-n-heptyloxy-5,5,8-trimethyl-5,6-dihydronaphthalen-2-yl)-n-propylamino]benzoate ((Compound 129, 0.024 g, 0.049 mmol) was reacted to afford 0.017 g (75%) of the title compound as a yellow solid. PNMR (300 MHz, CDCl$_3$) 0.85 (m, 4 H), 0.90 (m, 3 H), 1.15 (m, 9 H), 1.28 (s, 6 H), 1.58 (m, 2 H), 1.70 (m, 2 H), 1.98 (s, 3 H), 2.20 (m, 2 H), 3.58 (m, 2 H), 3.90 (m, 2 H), 5.68 (m, 1 H), 6.52 (d, 2 H, J=8.8 Hz), 6.90 (s, 1 H), 7.02 (s, 1 H), 7.85 (d, 2 H, J=9.3 Hz).

Ethyl 4-[(3-benzyloxy-5,5,8-trimethyl-5,6-dihydronaphthalen-2-yl)-n-propylamino]benzoate (Compound 130)

Following General Procedure P ethyl 4-(3-benzyloxy-5,5,8-trimethyl-5,6-dihydronaphthalen-2-ylamino)benzoate (Compound 114, 0.030 g, 0.07 mmol) was reacted with propionaldehyde to afford 0.021 g (65%) of the title compound as a yellow solid.

PNMR (300 MHz, CDCl$_3$) 1.25 (s, 6 H), 1.35 (m, 3 H), 1.60 (m, 5 H), 1.98 (s, 3 H), 2.22 (d, 2 H, J=4.8 Hz), 3.58 (m, 2 H), 4.32 (q, 2 H, J=7.0 Hz), 5.02 (s, 2 H), 5.68 (m, 1 H), 6.58 (d, 2 H, J=8.8 Hz), 6.98 (s, 1 H), 7.05 (s, 1 H), 7.13 (m, 2 H), 7.26 (m, 3 H), 7.85 (d, 2 H, J=9.0 Hz).

4-[(3-Benzyloxy-5,5,8-trimethyl-5,6-dihydronaphthalen-2-yl)-n-propylamino]benzoic acid (Compound 147)

Following General Procedure E, ethyl 4-[(3-benzyloxy-5,5,8-trimethyl-5,6-dihydronaphthalen-2-yl)-n-propylamino]benzoate (Compound 130, 0.021 g, 0.043 mmol) was reacted to afford 0.011 g (55%) of the title compound as a yellow oil.

PNMR (300 MHz, CDCl$_3$) 0.94 (m, 3 H), 1.25 (s, 6 H), 1.57 (m, 2 H), 2.02 (s, 3 H), 2.20 (m, 2 H), 3.58 (m, 2 H), 5.02 (s, 2 H), 5.68 (m, 1 H), 6.55 (d, 2 H, J=8.8 Hz), 6.98 (s, 1 H), 7.04 (s, 1 H), 7.15 (m, 2 H), 7.25 (m, 3 H), 7.85 (d, 2 H, J=9.0 Hz).

6-Bromo-4-isopropyl-1,1-dimethyl-7-methoxy-1,2-dihydronaphthalene (Compound 102)

Following General Procedure A, 7-bromo-6-methoxy-4,4-dimethyl-3,4-dihydro-2H-naphthalen-1-one (Compound 92, 1.0 g, 3.5 mmol) was reacted with i-PrMgBr to afford 0.74 g (68%) of the title compound as a white solid.

PNMR (300 MHz, CDCl$_3$) 1.18 (d, 2 H, J=6.4 Hz), 1.24 (s, 6 H), 2.18 (d, 2 H, J=4.8 Hz), 2.86 (m, 1 H), 3.94 (s, 3 H), 5.68 (t, 1 H, J=4.5 Hz), 6.88 (s, 1 H), 7.48 (s, 1 H).

3-Bromo-5-isopropyl-8,8-dimethyl-7,8-dihydronaphthalen-2-ol (Compound 97)

To a suspension of sodium hydride 60% w/w (0.30 g, 6.8 mmol) in 20 mL of DMF under argon atmosphere was added slowly ethanethiol 98% (0.5 mL, 6.8 mmol), and the resulting solution was stirred for 15 min. A solution of 6-bromo-4-isopropyl-1,1-dimethyl-7-methoxy-1,2-dihydronaphthalene (Compound 102, 600 mg, 1.9 mmol) in 3 mL of DMF was added, and the reaction mixture was refluxed for 5 h, then cooled to room temperature, acidified with 2 N HCl, diluted with water and extracted with ethyl acetate. The combined extracts were washed with brine, dried over MgSO$_4$, and filtered. The solvent was removed to afford 0.57 g (100%) of the title compound as a dark brown oil.

PNMR (300 MHz, CDCl$_3$) 1.15 (d, 6 H, J=6.5 Hz), 1.25 (s, 6 H), 2.12 (d, 2 H, J=4.8 Hz), 2.81 (m, 1 H), 5.62 (t, 1 H, J=4.3 Hz), 6.98 (s, 1 H), 7.36 (s, 1 H).

6-Bromo-7-ethoxy-4-isopropyl-1,1-dimethyl-1,2-dihydronaphthalene (Compound 103)

Following General Procedure O, 3-bromo-5-isopropyl-8,8-dimethyl-7,8-dihydronaphthalen-2-ol (Compound 97, 0.40 g, 1.3 mmol) was reacted with iodoethane to afford 0.16 g (37%) of the title compound as a yellow oil.

PNMR (300 MHz, CDCl$_3$) 1.18 (d, 6 H, J=6.7 Hz), 1.24 (s, 6 H), 1.49 (m, 3 H), 2.18 (d, 2 H, J=4.8 Hz), 2.81 (m, 1 H), 4.16 (m, 2 H), 5.71 (t, 1 H, J=4.5 Hz)., 6.91 (s, 1 H), 7.50 (s, 1 H).

6-Bromo-4-isopropyl-1,1-dimethyl-7-n-propoxy-1,2-dihydronaphthalene (Compound 104)

Following General Procedure O, 3-bromo-5-isopropyl-8,8-dimethyl-7,8-dihydronaphthalen-2-ol (Compound 97, 0.36 g, 1.2 mmol) was reacted with 1-iodopropane to afford 0.29 g (70%) of the title compound as a clear oil.

PNMR (300 MHz, CDCl$_3$) 1.22 (d, 6 H, J=6.7 Hz), 1.23 (m, 3 H), 1.28 (s, 6 H), 1.94 (m, 2 H), 2.22 (m, 2 H), 2.92 (m, 1 H), 4.06 (m, 2 H), 5.75 (m, 1 H), 6.95 (s, 1 H), 7.56 (s, 1 H).

6-Bromo-4-isopropyl-1,1-dimethyl-7-n-propoxy-1,2-dihydronaphthalene (Compound 105)

Following General Procedure O, 3-bromo-5-isopropyl-8,8-dimethyl-7,8-dihydronaphthalen-2-ol (Compound 97, 0.36 g, 1.2 mmol) was reacted with 2-iodopropane to afford 0.18 g (43%) of the title compound as a clear oil.

PNMR (300 MHz, CDCl$_3$) 1.19 (d, 6 H, J=6.5 Hz), 1.25 (s, 6 H), 1.42 (d, 6 H, J=6.2 Hz), 2.19 (d, 2 H, J=4.7 Hz), 2.85 (m, 1 H), 4.60 (m, 1 H), 5.72 (t, 1 H, J=4.7 Hz), 6.92 (s, 1 H), 7.51 (s, 1 H).

6-Bromo-7-n-butoxy-4-isopropyl-1,1-dimethyl-1,2-dihydronaphthalene (Compound 106)

Following General Procedure O, 3-bromo-5-isopropyl-8,8-dimethyl-7,8-dihydronaphthalen-2-ol (Compound 97, 0.36 g, 1.2 mmol) was reacted with 1-iodobutane to afford 0.28 g (66%) of the title compound as a clear oil.

PNMR (300 MHz, CDCl$_3$) δ 1.04 (t, 2 H, J=4.4 Hz), 1.18 (d, 6 H, J=4.5 Hz), 1.26 (s, 6 H), 1.68 (m, 2 H), 1.89 (m, 2 H), 2.20 (d, 2 H, J=4.7 Hz), 2.89 (m, 1 H), 4.10 (t, 2 H, J=3.8 Hz), 5.72 (t, 1 H, J=4.5 Hz), 6.91 (s, 1 H), 7.52 (s, 1 H).

6-Bromo-7-n-hexyloxy-4-isopropyl-1,1-dimethyl-1,2-dihydronaphthalene (Compound 107)

Following General Procedure O, 3-bromo-5-isopropyl-8,8-dimethyl-7,8-dihydronaphthalen-2-ol (Compound 97, 0.11 g, 0.37 mmol) was reacted with 1-iodohexane to afford 0.058 g (39%) of the title compound as a clear oil.

PNMR (300 MHz, CDCl$_3$) δ 1.15 (d, 6 H, J=4.5 Hz), 1.25 (s, 6 H), 1.35 (m, 7 H), 1.55 (m, 2 H), 1.84 (m, 2 H), 2.16 (d, 2 H, J=4.8 Hz), 2.86 (m, 1 H), 4.18 (t, 2 H, J=6.5 Hz), 5.68 (t, 1 H, J=4.5 Hz) 6.85 (s, 1 H), 7.46 (s, 1 H).

7-Benzyloxy-6-bromo-4-isopropyl-1,1-dimethyl-1,2-dihydronaphthalene (Compound 108)

Following General Procedure O, 3-bromo-5-isopropyl-8,8-dimethyl-7,8-dihydronaphthalen-2-ol (Compound 97, 0.29 g, 0.98 mmol) was reacted with benzylbromide to afford 0.38 g (100%) of the title compound as a yellow oil.

PNMR (300 MHz, CDCl$_3$) δ 1.15 (d, 6 H, J=4.5 Hz), 1.26 (s, 6 H), 2.14 (d, 2 H, J=4.7 Hz), 2.86 (m, 1 H), 5.18 (s, 2 H), 5.69 (t, 1 H, J=4.5 Hz), 6.91 (s, 1 H), 7.36 (m, 5 H), 7.50 (s, 1 H).

6-Bromo-4-isopropyl-1,1-dimethyl-7-(4-methylbenzyloxy)-1,2-dihydronaphthalene (Compound 109)

Following General Procedure O, 3-bromo-5-isopropyl-8,8-dimethyl-7,8-dihydronaphthalen-2-ol (Compound 97, 0.14 g, 0.49 mmol) was reacted with 4-methylbenzylbromide to afford 0.19 g (100%) of the title compound as a yellow oil. PNMR (300 MHz, CDCl$_3$) δ 1.22 (d, 6 H, J=4.5 Hz), 1.28 (s, 6 H), 2.22 (d, 2 H, J=4.7 Hz), 2.45 (s, 3 H), 5.22 (s, 2 H), 5.78 (t, 1 H, J=4.5 Hz), 7.02 (s, 1 H), 7.22 (d, 2 H, J=8.8 Hz), 7.38 (d, 2 H, J=9.3 Hz), 7.60 (s, 1 H).

6-Bromo-7-(3,5-di-t-butylbenzyloxy)-4-isopropyl-1,1-dimethyl-1,2-dihydronaphthalene (Compound 110)

Following General Procedure O, 3-bromo-5-isopropyl-8,8-dimethyl-7,8-dihydronaphthalen-2-ol (Compound 97, 0.14 g, 0.48 mmol) was reacted with 3,5-di-t-butylbenzylbromide to afford 0.074 g (72%) of the title compound as a yellow solid. PNMR (300 MHz, CDCl$_3$) δ 1.20 (m, 12 H), 1.37 (s, 18 H), 2.15 (d, 2 H, J=4.8 Hz), 2.85 (m, 1 H), 5.20 (s, 2 H), 5.72 (m, 3 H), 6.95 (s, 1 H), 7.40 (m, 3 H), 7.55 (s, 1 H).

Ethyl 4-(8-isopropyl-3-methoxy-5,5-dimethyl-5,6-dihydronaphthalen-2-ylamino)benzoate (Compound 115)

Following General Procedure P, 6-bromo-4-isopropyl-1,1-dimethyl-7-methoxy-1,2-dihydronaphthalene (Compound 102, 0.26 g, 0.85 mmol) was reacted to afford 0.060 g (18%) of the title compound as a yellow oil.
PNMR (300 MHz, CDCl$_3$) δ 1.15 (d, 6 H, J=6.7 Hz), 1.25 (s,.6 H), 1.40 (t, 3 H, J=7.0 Hz), 2.20 (d, 2 H, J=4.8 Hz), 2.82 (m, 1 H), 3.90 (s, 3 H), 4.35 (q, 2 H, J=7.0 Hz), 5.70 (t, 1 H, J=4.7 Hz), 6.22 (s, 1 H), 6.92 (s, 1 H), 7.02 (d, 2 H, J=8.5 Hz), 7.40 (s, 1 H), 7.94 (d, 2 H, J=8.3 Hz).

Ethyl 4-[Ethyl-(8-isopropyl-3-methoxy-5,5-dimethyl-5,6-dihydronaphthalen-2-yl)amino]benzoate (Compound 131)

Following General Procedure D, ethyl 4-(8-isopropyl-3-methoxy-5,5-dimethyl-5,6-dihydronaphthalen-2-ylamino)benzoate (Compound 115, 0.020 g, 0.05 mmol) was reacted to afford 0.021 g (100%) of the title compound as a yellow solid.
PNMR (300 MHz, CDCl$_3$) δ 1.12 (d, 6 H, J=6.7 Hz), 1.22 (m, 6 H), 1.25 (s, 6 H), 2.18 (d, 2 H, J=4.8 Hz), 2.81 (m, 1 H), 3.58 (q, 2 H, J=7.0 Hz), 3.78 (s, 3 H), 4.30 (q, 2 H, J=7.0 Hz), 5.70 (t, 1 H, J=4.8 Hz), 6.58 (d, 2 H, J=8.3 Hz), 6.94 (s, 1 H), 7.08 (s, 1 H), 7.85 (d, 2 H, J=9.0 Hz).

4-[Ethyl-(8-isopropyl-3-methoxy-5,5-dimethyl-5,6-dihydronaphthalen-2-yl)amino]benzoic acid (Compound 148)

Following General Procedure E, ethyl 4-[ethyl-(8-isopropyl-3-methoxy-5,5-dimethyl-5,6-dihydronaphthalen-2-yl)ethylamino]benzoate (Compound 131, 0.021 g, 0.05 mmol) was reacted to afford 0.020 g (100%) of the title compound as a yellow oil. PNMR (300 MHz, CDCl$_3$) δ 1.10 (d, 6 H, J=6.7 Hz), 1.22 (m, 3 H), 1.25 (s, 6 H), 2.20 (d, 2 H, J=4.8 Hz), 2.80 (m, 1 H), 3.68 (q, 2 H, J=7.0 Hz), 3.78 (s, 3 H), 5.68 (t, 1 H, J=4.8 Hz), 6.55 (d, 2 H, J=8.8 Hz), 6.92 (s, 1 H), 7.08 (s, 1 H), 7.85 (d, 2 H, J=8.8 Hz).

Ethyl 4-Ethoxy-8-isopropyl-5,5-dimethyl-5,6-dihydronaphthalen-2-ylamino)benzoate (Compound 116)

General Procedure R A solution of 6-bromo-7-ethoxy-4-isopropyl-1,1-dimethyl-1,2-dihydronaphthalene (Compound 103, 0.16 g, 0.48 mmol), Pd$_2$(dba)$_3$ (0.09 g, 0.10 mmol), Cy—MAP (0.057 g, 0.14 mmol), K$_3$PO$_4$ (0.15 g, 0.72 mmol), ethyl 4-aminobenzoate (0.10 g, 0.58 mmol), and 5 mL of toluene was flushed with argon for 10 min, then stirred at 100° C. in a sealed tube for 2 days. Then the reaction vessel was cooled to room temperature, the solvent was removed by evaporation, and the residue was purified by flash column chromatography (hexane:ethyl acetate=4:1) to afford 0.12 g (60%) of the title compound as a yellow oil. PNMR (300 MHz, CDCl$_3$) δ 1.12 (d, 6 H, J=6.7 Hz), 1.25 (s, 6 H), 1.36 (m, 3 H), 2.20 (d, 2 H, J=4.7 Hz), 2.82 (m, 1 H), 3.98 (q, 2 H, J=7.0 Hz), 4.33 (q, 2 H, J=7.0 Hz) 5.68 (t, 1 H, J=4.4 Hz), 6.57 (d, 2 H, J=8.3 Hz), 6.95 (s, 1 H), 7.10 (s, 1 H), 7.80 (d, 2 H, J=8.2 Hz).

Ethyl 4-[(3-Ethoxy-8-isopropyl-5,5-dimethyl-5,6-dihydronaphthalen-2-yl)ethylamino]benzoate (Compound 132)

Following General Procedure D, ethyl 4-(3-ethoxy-8-isopropyl-5,5-dimethyl-5,6-dihydronaphthalen-2-ylamino)benzoate (Compound 116, 0.12 g, 0.30 mmol) was reacted to afford 0.024 g (19%) of the title compound as a yellow oil.
PNMR (300 MHz, CDCl$_3$), δ 1.12 (d, 6 H, J=6.7 Hz), 1.25 (m, 3 H), 1.28 (s, 6 H), 1.36 (m, 3 H), 2.22 (d, 2 H, J=4.7 Hz), 2.82 (m, 1 H), 3.69 (q, 2 H, J=6.7 Hz), 3.98 (q, 2 H, J=7.0 Hz), 4.33 (q, 2 H, J=7.0 Hz), 5.68 ((m, 1 H), 6.57 (d, 2 H, J=8.2 Hz), 6.97 (s, 1 H), 7.10 (s, 1 H), 7.85 (d, 2 H, J=8.2 Hz).

4-[(3-Ethoxy-8-isopropyl-5,5-dimethyl-5,6-dihydronaphthalen-2-yl)ethylamino]benzoic acid (Compound 149)

Following General Procedure E, ethyl 4-[(3-ethoxy-8-isopropyl-5,5-dimethyl-5,6-dihydronaphthalen-2-yl)ethylamino]benzoate (Compound 132, 0.024 g, 0.055 mmol) was reacted to afford 0.013 g (55%) of the title compound as a yellow oil.
PNMR (300 MHz, CDCl$_3$) δ 1.03 (d, 6 H, J=6.7 Hz), 1.14 (m, 3 H), 1.19 (s, 6 H), 2.74 (m, 1 H), 3.62 (q, 2 H, J=7.0 Hz), 3.90 (q, 2 H, J=7.0 Hz), 5.60 (t, 1 H, J=4.4 Hz), 6.48 (d, 2 H, J=9.1 Hz), 6.82 (s, 1 H), 6.99 (s, 1 H), 7.78 (d, 2 H, J=9.1 Hz).

Ethyl 4-(8-isopropyl-5,5-dimethyl-3-n-propoxy-5,6-dihydronaphthalen-2-ylamino)benzoate (Compound 117)

Following General Procedure R, 6-bromo-4-isopropyl-1,1-dimethyl-7-n-propoxy-1,2-dihydronaphthalene (Compound 104, 0.29 g, 0.84 mmol) was reacted to afford 0.18 g (50%) of the title compound as a yellow oil.
PNMR (300 MHz, CDCl$_3$), δ 1.07 (t, 3 H, J=7.3 Hz), 1.20 (d, 6 H, J=6.7 Hz), 1.29 (s, 6 H), 1.42 (t, 3 H, J=7.3 Hz), 1.86 (q, 2 H, J=7.3 Hz), 2.12 (d, 2 H, J=4.8 Hz), 4.05 (t, 2 H, J=7.3 Hz), 4.18 (q, 2 H, J=7.3 Hz), 5.74 (t, 1 H, J=4.4 Hz), 6.32 (s, 1 H), 6.95 (s, 1 H), 7.08 (d, 2 H, J=8.8 Hz), 7.44 (s, 1 H), 8.00 (d, 2 H, J=8.8 Hz).

Ethyl 4-[Ethyl-(8-isopropyl-5,5-dimethyl-3-n-propoxy-5,6-dihydronaphthalen-2-yl)amino]benzoate (Compound 133)

Following General Procedure D, ethyl 4-(8-isopropyl-5,5-dimethyl-3-n-propoxy-5,6-dihydronaphthalen-2-ylamino)benzoate (Compound 117, 0.18 g, 0.43 mmol) was reacted with acetaldehyde to afford 0.14 g (70%) of the title compound as a yellow oil.
PNMR (300 MHz, CDCl$_3$) δ 0.83 (t, 3 H, J=7.3 Hz), 1.18 (d, 6 H, J=6.7 Hz), 1.23 (m, 3 H), 1.26 (s, 6 H), 1.37 (t, 3 H, J=7.3 Hz), 1.60 (m, 2 H), 2.20 (d, 2 H, J=4.8 Hz), 3.69 (q,2 H, J=7.4 Hz), 3.90 (t, 2 H, J=6.5 Hz), 4.3 (q, 2 H, J=7.1 Hz), 5.68 (t, 1 H, J=4.8 Hz), 6.56 (d, 2 H, J=8.8 Hz), 6.94 (s, 1 H), 7.10 (s, 1 H), 7.84 (d, 2 H, J=8.8 Hz).

4-[Ethyl-(8-isopropyl-5,5-dimethyl-3-n-propoxy-5,6-dihydronaphthalen-2-yl)amino]benzoic acid (Compound 150)

Following General Procedure E, ethyl 4-[ethyl-(8-isopropyl-5,5-dimethyl-3-n-propoxy-5,6-dihydronaphthalen-2-yl)amino]benzoate (Compound 133, 0.14 g, 0.31 mmol) was reacted to afford 0.034 g (27%) of the title compound as a yellow solid. PNMR (300 MHz, CDCl$_3$) δ 0.85 (m, 3 H), 1.12 (d, 2 H, J=6.7 Hz), 1.22 (m, 3 H), 1.26 (s, 6 H), 1.28 (m, 2 H), 2.20 (d, 2 H, J=4.8 Hz), 2.80 (m, 1 H), 3.80 (m, 2 H), 4.18 (q, 2 H, J=7.0 Hz), 5.67 (m, 1 H), 6.48 (d, 2 H, J=8.8 Hz), 6.94 (s, l H), 7.08 (s, 1 H), 7.82 (d, 2 H, J=8.8 Hz).

Ethyl 4-(3-isopropoxy-8-isopropyl-5,5-dimethyl-5,6-dihydronaphthalen-2-ylamino)benzoate (Compound 118)

Following General Procedure R, 6-bromo-4-isopropyl-1,1-dimethyl-7-isopropoxy-1,2-dihydronaphthalene (Compound 105, 0.18 g, 0.52 mmol) was reacted to afford 0.11 g (48%) of the title compound as a yellow oil.
PNMR (300 MHz, CDCl$_3$), δ 1.10 (d, 6 H, J=6.7 Hz, 1.25 (s, 6 H), 1.30 (m, 3 H), 1.40 (d, 6 H, J=6.1 Hz), 2.20 (d, 2

H, J=4.8 Hz), 2.32 (m, 1 H), 4.36 (q, 2 H, J=7.0 Hz), 4.55 (m, 1 H), 5.68 (t, 1 H, J=4.7 Hz), 6.25 (s, 1 H), 6.92 (s, 1 H), 7.05 (d, 2 H, J=8.8 Hz), 7.38 (s, 1 H), 7.92 (d, 2 H, J=8.8 Hz).

Ethyl 4-[Ethyl-(3-isopropoxy-8-isopropyl-5,5-dimethyl-5,6-dihydronaphthalen-2-yl)amino]benzoate (Compound 134)

Following General Procedure D, ethyl 4-(3-isopropoxy-8-isopropyl-5,5-dimethyl-5,6-dihydronaphthalen-2-ylamino)benzoate (Compound 118, 0.11 g, 0.25 mmol) was reacted to afford 0.038 g (34%) of the title compound as a yellow oil.
PNMR (300 MHz, CDCl₃), δ 1.10 (d, 6 H, J=6.7 Hz), 1.19 (d, 6 H, J=6.2 Hz), 1.22 (m, 3 H), 1.25 (s, 6 H), 1.38 (t, 3 H, J=7.4 Hz), 2.20 (d, 2 H, J=4.7 Hz), 2.80 (m, 1 H), 3.67 (q, 2 H, J=7.1 Hz), 4.30 (q, 2 H, J=6.0 Hz), 4.50 (m, 1 H), 5.68 (t, 1 H, J=4.8 Hz), 6.54 (d, 2 H, J=8.5 Hz), 6.95 (s, 1 H), 7.08 (s, 1 H), 7.83 (d, 2 H, J=8.5 Hz).

4-[Ethyl-(3-isopropoxy-5,5-dimethyl-8-isopropyl-5,6-dihydronaphthalen-2-yl)amino]benzoic acid (Compound 151)

Following General Procedure E, ethyl 4-[ethyl-(3-isopropoxy-5,5-dimethyl-8-isopropyl-5,6-dihydronaphthalen-2-yl)amino]benzoate (Compound 134, 0.038 g, 0.09 mmol) was reacted to afford 0.027 g (74%) of the title compound as a yellow solid. PNMR (300 MHz, CDCl₃), δ 1.10 (d, 6 H, J=6.7 Hz), 1.15 (m, 3 H), 1.18 (d, 6 H, J=6.1 Hz), 1.25 (s, 6 H), 2.20 (d, 2 H, J=4.8 Hz), 2.80 (m, 1 H), 3.68 (q, 2 H, J=7.0 Hz), 4.45 (q, 1 H, J=6.2 Hz), 5.67 (6, 1 H, J=4.0 Hz), 6.58 (d, 2 H, J=9.1 Hz) 6.95 (s, 1 H), 7.01 (s, 1 H), 7.87 (d, 2 H, J=9.1 Hz).

Ethyl 4-(3-n-butoxy-8-isopropyl-5,5-dimethyl-5 6-dihydronaphthalen-2-ylamino)benzoate (Compound 119)

Following General Procedure R, 6-bromo-7-n-butoxy-4-isopropyl-1,1-dimethyl-7,8-dihydronaphthalen-2-ol (Compound 106, 0.19 g, 0.54 mmol) was reacted to afford 0.048 g (21%) of the title compound as a yellow oil.
PNMR (300 MHz, CDCl₃), δ 1.03 (t, 3 H, J=7.1 Hz), 1.14 (d, 6 H, J=6.5 Hz), 1.23 (s, 6 H), 1.28 (m, 2 H), 1.40 (t, 3 H, J=7.3 Hz), 1.47 (m, 2 H), 2.18 (d,2 H, J=4.8 Hz),2.82 (m, 1 H), 4.06 (t, 2 H, J=7.5 Hz), 4.35 (q,2 H, J=7.0 Hz), 5.69 (t, 1 H, J=4.1 Hz), 6.27 (s, 1 H), 6.89 (s, 1 H), 7.06 (d, 2 H, J=8.8 Hz), 7.38 (s, 1 H), 7.92 (d, 2 H, J=8.8 Hz).

Ethyl 4-[(3-n-butoxy-8-isopropyl-5,5-dimethyl-5,6-dihydronaphthalen-2-yl)ethylamino]benzoate (Compound 135)

Following General Procedure D, ethyl 4-(3-n-butoxy-8-isopropyl-5,5-dimethyl-5,6-dihydronaphthalen-2-ylamino)benzoate (Compound 119, 0.048 g, 0.11 mmol) was reacted to afford 0.085 g (100%) of the title compound as a yellow solid.
PNMR (300 MHz, CDCl₃), δ 0.85 (m, 3 H), 1.10 (d, 2 H, J=6.5 Hz), 1.25 (s, 6 H), 1.38 (m, 5 H), 1.58 (m, 3 H), 2.20 (d, 2 H, J=4.8 Hz), 2.80 (m, 1 H), 3.64 (m, 2 H), 3.92 (m, 2 H), 4.25 (q, 2 H, J=7.1 Hz), 4.60 (q, 2 H, J=6.8 Hz), 5.68 (m, 1 H), 6.50 (d, 2 H, J=8.9 Hz), 6.94 (s, 1 H), 7.08 (s, 1 H), 7.81 (d, 2 H, J=8.8 Hz).

4-[(3-n-Butoxy-8-isopropyl-5,5-dimethyl-5,6-dihydronaphthalen-2-yl)ethylamino]benzoic acid (Compound 152)

Following General Procedure E, ethyl 4-[(3-n-butoxy-8-isopropyl-5,5-dimethyl-5,6-dihydronaphthalen-2-yl)ethylamino]benzoate (Compound 135, 0.051 g, 0.11 mmol) was reacted to afford 0.045 g (94%) of the title compound as a yellow solid.
PNMR (300 MHz, CDCl₃), δ 0.82 (m, 3 H), 1.10 (d, 6 H, J=6.7 Hz), 1.30 (m, 5 H), 1.25 (s, 6 H), 2.20 (d, 2 H, J=4.8 Hz), 2.80 (m, 1 H), 3.64 (m, 2 H), 3.95 (m, 2 H), 4.10 (m, 2 H), 5.64 (m, 1 H), 6.58 (d, 2 H, J=8.8 Hz), 6.94 (s, 1 H), 7.08 (s, 1 H), 7.84 (d, 2 H, J=9.0 Hz).

Ethyl 4-(3-n-Hexyloxy-8-isopropyl-5,5-dimethyl-5,6-dihydronaphthalen-2-ylamino)benzoate (Compound 120)

Following General Procedure P, 6-bromo-7-n-hexyloxy-4-isopropyl-1,1-dihydronaphthalene (Compound 107, 0.058 g, 0.15 mmol) was reacted to afford 0.013 g (18%) of the title compound as a clear oil.
PNMR (300 MHz, CDCl₃), δ 0.95 (m, 5 H), 1.10 (d, 6 H, J=4.8 Hz), 1.20 (s, 6 H), 1.35 (m, 7 H), 1.78 (m, 2 H), 2.18 (d, 2 H, J=4.8 Hz), 2.81 (m, 1 H), 4.02 (m, 2 H), 4.35 (m, 2 H), 5.58 (m, 1 H), 6.22 (s, 1 H), 7.02 (d, 2 H, J=9.0 Hz), 7.28 (s, 1 H), 7.39 (s, 1 H), 7.92 (d, 2 H, J=9.0 Hz).

Ethyl 4-[ethyl-(3-n-hexyloxy-8-isopropyl-5,5-dimethyl-5,6-dihydronaphthalen-2-yl)amino]benzoate, (Compound 136)

Following General Procedure D, ethyl 4-(3-n-hexyloxy-8-isopropyl-5,5-dimethyl-5,6-dihydronaphthalen-2-ylamino)benzoate (Compound 120, 0.013 g, 0.03 mmol) was reacted to afford 0.013 g (96%) of the title compound as a clear oil.
PNMR (300 MHz, CDCl₃), δ 1.12 (d, 6 H, J=6.7 Hz), 1.20 (m, 6 H), 1.25 (s, 6 H), 1.32 (m, 5 H), 1.60 (m, 6 H), 2.18 (d, 2 H, J=4.8 Hz), 2.81 (m, 1 H), 3.68 (q, 2 H, J=7.0 Hz), 3.90 (m, 2 H), 4.30 (q, 2 H, J=7.2 Hz), 5.58 (t, 1 H, J=3.0 Hz), 6.55 (d, 2 H, J=9.0 Hz), 6.94 (s, 1 H), 7.10 (s, 1 H), 7.82 (d, 2 H, J=8.8 Hz).

4-Ethyl-(3-n-hexyloxy-8-isopropyl-5,5-dimethyl-5,6-dihydronaphthalen-2-yl)amino]benzoic acid (Compound 153)

Following General Procedure E, ethyl 4-[ethyl-(3-n-hexyloxy-8-isopropyl-5,5-dimethyl-5,6-dihydronaphthalen-2-yl)amino]benzoate (Compound 136, 0.013 g, 0.027 mmol) was reacted to afford 0.009 g (73%) of the title compound as a yellow oil.
PNMR (300 MHz, CDCl₃), δ 1.10 (d, 6 H, J=6.7 Hz), 1.20 (m, 9 H), 1.26 (s, 6 H), 1.58 (m, 3 H), 2.18 (d, 2 H, J=4.8 Hz), 2.81 (m, 1 H), 3.72 (m, 4 H), 3.90 (m, 2 H), 5.68 (m, 1 H), 6.57 (d, 2 H, J=8.8 Hz), 6.94 (s, 1 H), 7.10 (s, 1 H), 7.85 (d, 2 H, J=9.0 Hz)

Ethyl 4-(3-benzyloxy-8-isopropyl-5,5-dimethyl-5,6-dihydronaphthalen-2-ylamino)benzoate (Compound 121)

Following General Procedure P, 7-benzyloxy-6-bromo-4-isopropyl-1,1-dimethyl-1,2-dihydronaphthalene (Compound 108, 0.30 g, 0.78 mmol) was reacted to afford 0.040 g (11%) of the title compound as a light yellow solid.
PNMR (300 MHz, CDCl₃), δ 1.16 (d, 6 H, J=6.7 Hz), 1.22 (s, 6 H), 1.39 (t, 3 H, J=7.1 Hz), 2.18 (d, 2 H, J=4.4 Hz), 2.83 (m, 1 H), 4.34 (q, 2 H, J=7.1 Hz), 5.13 (s, 2 H), 5.72 (t, 1 H, J=4.5 Hz), 6.24 (s, 1 H), 7.01 (s, 1 H), 7.07 (d, 2 H, J=8.7 Hz), 7.40 (m, 6 H), 7.93 (d, 2 H, J=8.7 Hz).

Ethyl 4-[(3-benzyloxy-8-isopropyl-5,5-dimethyl-5,6-dihydronaphthalen-2-yl)ethylamino]benzoate (Compound 137)

Following General Procedure D, ethyl 4-(3-benzyloxy-8-isopropyl-5,5-dimethyl-5,6-dihydronaphthalen-2-ylamino)benzoate (Compound 121, 0.020 g, 0.04 mmol) was reacted to afford 0.017 g (80%) of the title compound as a yellow solid.
PNMR (300 MHz, CDCl₃), δ 1.12 (d, 6 H, J=6.7 Hz), 1.25 (s, 6 H), 1.27 (m, 3 H), 1.35 (t, 3 H, J=7.1 Hz), 2.18 (d, 2 H, J=4.5 Hz), 2.82 (m, 1 H), 3.72 (q, 2 H, J=7.3 Hz), 4.32 (q, 2 H, J=7.0 Hz), 5.05 (s, 2 H), 5.68 (t, 1 H, J=4.5 Hz), 6.68 (d, 2 H, J=8.8 Hz), 7.02 (s, 1 H), 7.35 (m, 3 H), 7.58 (m, 3 H), 7.85 (d, 2 H, J=8.8 Hz).

4-[(3-Benzyloxy-8-isopropyl-5,5-dimethyl-5,6-dihydronaphthalen-2-yl)ethylamino]benzoic acid (Compound 154)

Following General Procedure E, ethyl 4-[(3-benzyloxy-8-isopropyl-5,5-dimethyl-5,6-dihydronaphthalen-2-yl)ethylamino]benzoate (Compound 137, 0.017 g, 0.03 mmol) was reacted to afford 0.013 g (82%) of the title compound as a yellow oil.
PNMR (300 MHz, CDCl$_3$), δ 1.10 (d, 6 H, J=6.7 Hz), 1.25 (s, 6 H), 1.28 (m, 3 H), 2.18 (d, 2 H, J=4.5 Hz), 2.82 (m, 1 H), 3.72 (q, 2 H, J=7.0 Hz), 5.03 (s, 2 H), 5.68 (t, 1 H, J=4.5 Hz), 6.58 (d, 2 H, J=8.8 Hz), 7.02 (s, 1 H), 7.12 (s, 1 H), 7.25 (m, 2 H), 7.25 (m, 3 H), 7.86 (d, 2 H, J=8.8 Hz).

Ethyl 4-[8-isopropyl-5,5-dimethyl-3-(4-methylbenzyloxy)5,6-dihydronaphthalen-2-ylamino]benzoate (Compound 122)

Following General Procedure R, 6-bromo-4-isopropyl-1,1-dimethyl-7-(4-methylbenzyloxy)1,2-dihydronaphthalene (Compound 109, 0.11 g, 0.28 mmol) was reacted to afford 0.066 g (50%) of the title compound as a light yellow oil.
PNMR (300 MHz, CDCl$_3$), δ 1.18 (d, 6 H, J=6.8 Hz), 1.25 (s, 6 H), 1.39 (q, 2 H, J=5.9 Hz), 2.20 (d, 2 H, J=3.9 Hz), 2.39 (s, 3 H), 2.84 (m, 1 H), 4.37 (m, 2 H), 5.10 (s, 2 H), 5.73 (m, 1 H), 6.25 (s, 1 H), 7.02 (d, 2 H, J=9.8 Hz), 7.20 (d, 2 H, J=7.8 Hz), 7.31 (d, 2 H, J=7.8 Hz), 7.42 (s, 1 H), 7.95 (d, 2 H, J=8.8 Hz).

Ethyl 4-{ethyl-[8-isopropyl-5,5-dimethyl-3-(4-methylbenzyloxy-5,6-dihydronaphthalen-2-yl]amino}benzoate (Compound 138)

Following General Procedure D, ethyl 4-[8-isopropyl-5,5-dimethyl-3-(4-methylbenzyloxy)5,6-dihydronaphthalen-2-ylamino]benzoate (Compound 122, 0.066 g, 0.14 mmol) was reacted to afford 0.069 g (99%) of the title compound as a yellow oil. PNMR (300 MHz, CDCl$_3$), δ 1.10 (d, 2 H, J=6.4 Hz), 1.23 (m, 12 H), 2.18 (d, 2 H, J=4.5 Hz), 2.30 (s, 3 H), 2.80 (m, 1 H), 3.70 (m, 2 H), 4.30 (m, 2 H), 5.01 (s, 2 H), 5.68 (t, 1 H, J=4.5 Hz), 6.57 (d, 2 H, J=9.3 Hz), 7.05 (m, 6 H), 7.84 (d, 2 H, J=8.8 Hz).

4-{Ethyl-[8-isopropyl-5,5-dimethyl-3-(4-methylbenzyloxy)-5,6-dihydronaphthalen-2-yl]amino}benzoic acid (Compound 155)

Following General Procedure E, ethyl 4{ethyl-[8-isopropyl-5,5-dimethyl-3-(4-methylbenzyloxy)-5,6-dihydronaphthalen-2-yl]amino}benzoate (Compound 138, 0.060 g, 0.12 mmol) was reacted to afford 0.049 g (86%) of the title compound as a yellow solid.
PNMR (300 MHz, CDCl$_3$), δ 1.10 (d, 6 H, J=6.4 Hz), 1.23 (m, 9 H), 2.11 (s, 3 H), 2.18 (d, 2 H, J=4.5 Hz), 2.30 (s, 3 H), 2.30 (m, 1 H), 3.70 (m, 2 H), 4.89 (s, 2 H), 5.68 (t, 1 H, J=4.2 Hz), 6.57 (d, 2 H, J=8.3 Hz), 7.05 (m, 6 H), 7.87 (d, 2 H, J=8.3 Hz).

Ethyl 4-[3-(3,5-Di-tert-butylbenzyloxy)-8-isopropyl-5,5-dimethyl-5,6-dihydronaphthalen-2-ylamino]benzoate (Compound 123)

Following General Procedure R, 6-bromo-7-(3,5-di-tert-butylbenzyloxy)-4-isopropyl-1,1-dimethyl-1,2-dihydronaphthalene (Compound 110, 0.074 g, 0.15 mmol) was reacted to afford 0.031 g (36%) of the title compound as a light yellow oil.
PNMR (300 MHz, CDCl$_3$), δ 0.90 (m, 3 H), 1.25 (m, 30 H), 2.19 (d, 2 H, J=4.8 Hz), 2.31 (m, 1 H), 4.36 (m, 2 H), 5.01 (s, 2 H), 5.68 (m, 1 H), 6.57 (d, 2 H, J=9.0 Hz), 7.02 (m, 3 H), 7.40 (m, 2 H), 7.90 (d, 2 H, J=9.3 Hz).

Ethyl 4-{[3-(3,5-di-t-butylbenzyloxy)-8-isopropyl-5,5-dimethyl-5,6-dihydronaphthalen-2-yl]ethylamino}benzoate (Compound 139)

Following General Procedure D, ethyl 4-[3-(3,5-di-tert-butylbenzyloxy)-8-isopropyl-5,5-dimethyl-5,6-dihydronaphthalen-2-ylamino]benzoate (Compound 123, 0.031 g, 0.05 mmol) was reacted with acetaldehyde to afford 0.033 g (100%) of the title compound as a yellow solid.
PNMR (300 MHz, CDCl$_3$), δ 0.90 (m, 3 H), 1.20 (m, 33 H), 2.09 (d, 2 H, J=4.8 Hz), 2.81 (m, 1 H), 3.75 (q, 2 H, J=6.9 Hz), 4.36 (m, 2 H), 5.04 (s, 2 H), 5.68 (t, 1 H, J=4.5 Hz), 6.57 (d, 2 H, J=9.0 Hz), 7.08 (m, 3 H), 7.80 (d, 2 H, J=9.3 Hz).

4-{[3-(3,5-di-t-butylbenzyloxy)-8-isopropyl-5,5-dimethyl-5,6-dihydronaphthalen-2-yl]ethylamino}benzoic acid (Compound 156)

Following General Procedure E, ethyl 4-{[3-(3,5-di-t-butylbenzyloxy)-8-isopropyl-5,5-dimethyl-5,6-dihydronaphthalen-2-yl]ethylamino}benzoate (Compound 139, 0.032 g, 0.05 mmol) was reacted to afford 0.019 g (61%) of the title compound as a yellow solid.
PNMR (300 MHz, CDCl$_3$), δ 0.90 (m, 3 H), 1.25 (m, 30 H), 2.18 (d, 2 H, J=4.8 Hz), 2.80 (m, 1 H), 3.72 (q, 2 H, J=6.9 Hz), 5.02 (s, 2 H), 5.70 (t, 1 H, J=4.5 Hz), 6.58 (d, 2 H, J=9.0 Hz), 7.08 (m, 3 H), 7.85 (d, 2 H, J=9.3 Hz).

Ethyl 4-[(3-benzyloxy)-8-isopropyl-5,5-dimethyl-5,6-dihydronaphthalen-2-yl]-n-propylamino]benzoate (Compound 140)

Following General Procedure D, (Compound 121, 0.020 g, 0.04 mmol) was reacted with propionaldehyde to afford 0.018 g (81%) of the title compound as a yellow solid.
PNMR (300 MHz, CDCl$_3$), δ 1.12 (d, 2 H, J=6.7 Hz), 1.25 (s, 6 H), 1.35 (t, 3 H, J=7.3 Hz), 1.68 (m, 5 H), 2.18 (d, 2 H, J=4.8 Hz), 2.82 (m, 1 H), 3.58 (t, 2 H, J=6.5 Hz), 4.32 (q, 2 H, J=7.0 Hz), 5.02 (s, 2 H), 5.68 (t, 1 H, J=4.4 Hz), 6.58 (d, 2 H, J=8.8 Hz), 7.00 (s, 1 H), 7.18 (m, 3 H), 7.28 (m, 3 H), 7.85 (d, 2 H, J=8.8 Hz).

4-[(3-Benzyloxy)-8-isopropyl-5,5-dimethyl-5,6-dihydronaphthalen-2-yl]-n-propylamino]benzoic acid (Compound 157)

Following General Procedure E, ethyl 4-[(3-benzyloxy)-8-isopropyl-5,5-dimethyl-5,6-dihydronaphthalen-2-yl]-n-propylamino]benzoate (Compound 140, 0.0177 g, 0.035 mmol) was reacted to afford 0.017 g 100%) of the title compound as a yellow solid. PNMR (300 MHz, CDCl$_3$), δ1.12 (d, 2 H, J=6.7 Hz), 1.25 (s, 6 H), 1.27 (m, 5 H), 2.18 (d, 2 H, J=4.8 Hz), 3.58 (t, 2 H, J=6.5 Hz), 5.04 (s, 2 H), 5.68 (t, 1 H, J=4.5 Hz), 6.58 (d, 2 H, J=8.8 Hz), 7.02 (s, 1 H), 7.15 (m, 3 H), 7.24 (m, 3 H), 7.88 (d, 2 H, J=9.0 Hz).

6-Bromo-4-t-butyl-7-methoxy-1,1-dimethyl-1,2-dihydronaphthalene (Compound 95)

Following General Procedure A, 7-bromo-6-methoxy-4,4-dimethyl-dihydro-2H-naphthalen-1-one (Compound 92, 1.5 g, 5.3 mmol) was reacted with t-butylmagnesium chloride to afford 0.5743 g (34%) of the title compound as a yellow oil.
PNMR (300 MHz, CDCl$_3$), δ 1.24 (s, 6 H), 1.35 (s, 9 H); 2.14 (d, 2 H, J=4.4 Hz), 3.93 (s, 3 H), 5.89 (t, 1 H, J=4.5 Hz), 6.90 (s, 1 H), 7.84 (s, 1 H).

3-Bromo-5-t-butyl-8,8-dimethyl-7,8-dihydronaphthalen-2-ol (Compound 98)

The same procedure as for preparing 3-bromo-5,8,8-trimethyl-7,8-dihydronaphthalen-2-ol (Compound 96) was used with 6-bromo-4-tert-butyl-7-methoxy-1,1-dimethyl-1,2-dihydronaphthalene (Compound 95, 0.57 g, 1.8 mmol) to give 0.55 g (100%) of the title .compound as a yellow oil.
PNMR (300 MHz, CDCl$_3$), δ 1.25 (s, 6 H), 1.31 (s, 9 H), 2.12 (d, 2 H, J=4.4 Hz), 5.88 (t, 1 H, J=4.5 Hz), 7.02 (s, 1 H), 7.73 (s, 1 H).

7-Benzyloxy-6-bromo-4-tert-butyl-1,1-dimethyl-1,2-dihydronaphthalene (Compound 111)

Following General Procedure O, 3-bromo-5-t-butyl-8,8-dimethyl-7,8-dihydronaphthalen-2-ol (Compound 98, 0.18 g, 0.58 mmol) was reacted with benzyl bromide to afford 0.23 g (100%) of the title compound as a yellow oil.
PNMR (300 MHz, CDCl$_3$), δ 1.33 (s, 6 H), 1.37 (s, 9 H), 2.32 (d, 2 H, J=4.4 Hz), 5.31 (s, 2 H), 5.87 (m, 1 H), 7.02 (s, 1 H), 7.56 (m, 5 H), 7.78 (s, 1 H).

Ethyl 4-(3-benzyloxy-8-t-butyl-5,5-dimethyl-5,6-dihydronaphthalen-2-ylamino)benzoate (Compound 124)

Following General Procedure R, 7-benzyloxy-6-bromo-4-tert-butyl-1,1-dimethyl-1,2-dihydronaphthalene (Compound 111, 0.10 g, 0.25 mmol) was reacted to afford 0.072 g (60%) of the title compound as a yellow oil. PNMR (300 MHz, CDCl$_3$), δ 1.20 (s, 6 H), 1.32 (s, 9 H), 1.38 (t, 3 H, J=7.0 Hz), 2.15 (d, 2 H, J=4.4 Hz), 4.34 (q, 2 H, J=7.0 Hz), 5.08 (s, 2 H), 5.88 (t, 1 H, J=4.5 Hz), 6.22 (s, 1 H), 7.02 (m, 3 H), 7.38 (m, 5 H), 7.72 (s, 1 H), 7.84 (d,2 H, J=8.8 Hz).

Ethyl 4-[(3-benzyloxy-8-t-butyl-5,5-dimethyl-5,6-dihydronaphthalen-2-yl)ethylamino]benzoate (Compound 141)

Following General Procedure D, ethyl 4-(3-benzyloxy-8-t-butyl-5,5-dimethyl-5,6-dihydronaphthalen-2-ylamino)benzoate (Compound 124, 0.10 g, 0.21 mmol) was reacted with acetaldehyde to afford 0.049 g (46%) of the 13 title compound as a yellow oil. PNMR (300 MHz, CDCl$_3$), δ 1.20 (s, 6 H), 1.25 (s, 9 H), 1.28 (m, 3 H), 3.60 (m, 2 H), 4.30 (q, 2 H, J=7.0 Hz), 5.02 (s, 2 H), 5.85 (t, 1 H, J=4.4 Hz), 6.58 (d, 2 H, J=9.0 Hz), 6.98 (s, 1 H), 7.15 (m,2 H), 7.24 (m, 3 H), 7.42 (s, 1 H), 7.84 (d, 2 H, J=8.8 Hz).

4-[(3-benzyloxy-8-t-butyl-5,5-dimethyl-5,6-dihydronaphthalen-2-yl)ethylamino]benzoic acid (Compound 158)

Following General Procedure E, ethyl 4-[(3-benzyloxy-8-t-butyl-5,5-dimethyl-5,6-dihydronaphthalen-2-yl)ethylamino]benzoate (Compound 141, 0.049 g, 0.10 mmol) was reacted to afford 0.045 g (99%) of the title compound as a yellow solid. PNMR (300 MHz, CDCl$_3$), δ 1.22 (s, 6 H), 1.24 (m, 3 H), 1.28 (s, 9 H), 2.16 (d, 2 H, J=4.5 Hz), 3.62 (m, 2 H), 5.02 (s, 2 H), 5.86 (t, 1 H, J=4.5 Hz), 6.58 (d, 2 H, J=8.5 Hz), 6.98 (s, 1 H), 7.15 (m, 2 H), 7.24 (m, 2 H),7.42 (s, 1 H), 7.78 (m, 2 H).

7-Bromo-1,4,4-trimethyl-1,2,3,4-tetrahydro-naphthalen-1-ol

Following General Procedure I, 7-bromo-4,4-dimethyl-3,4-dihydro-2H-naphthalen-1-one (2.04 g, 8.0 mmol) was reacted to give the title compound as an oil. PNMR (CDCl$_3$): δ 1.27 (s, 6 H), 1.51 (s, 3 H), 1.62–1.96 (m, 4 H), 3.73 (t, J=6.4 Hz, 1 H, OH), 7.14 (d, J=8.2 Hz, 1 H), 7.31 (dd, J=2.2, 8.2 Hz, 1 H), 7.70 (d, J=8.2 Hz, 1 H).

6-Bromo-1,1,4-trimethyl-1,2-dihydro-naphthalene

Following General Procedure J, 7-bromo-1,4,4-trimethyl-1,2,3,4-tetrahydro-naphthalen-1-ol (2.17 g, 8.0 mmol) was reacted to give the title compound as an oil. PNMR (CDCl$_3$): δ 1.23 (s, 6 H), 2.03 (s, 3 H), 2.18 (d, J=4.4 Hz, 2 H), 5.79 (t, J=4.4 Hz, 1 H), 7.15 (d, J=8.1 Hz, 1 H), 7.29–7.33 (overlapping s & dd, 2 H).

5,5,8-Trimethyl-5,6-dihydro-naphthalen-2-ylamine (Compound 159)

Following General Procedure K, 6-bromo-1,1,4-trimethyl-1,2-dihydro-naphthalene (1.97 g, 7.8 mmol) was reacted to give the title compound as a solid. PNMR (CDCl$_3$): δ 1.22 (s, 6 H), 2.03 (s, 3 H), 2.16 (d, J=4.3 Hz, 2 H), 3.57 (s, 2 H), 5.76 (t, J=4.3 Hz, 1 H), 6.57 (dd, J=2.4, 8.1 Hz, 1 H), 6.64(d, J=2.4 Hz, 1 H), 7.11 (d, J=8.1 Hz, 1 H).

N-(5,5,8-Trimethyl-5,6-dihydro-naphthalen-2-yl)-acetamide (Compound 162)

General Procedure T: A solution of 5,5,8-trimethyl-5,6-dihydro-naphthalen-2-ylamine (Compound 159, 1.47 g, 7.9 mmol) in 10 mL of dichloromethane was stirred at 0° C., and acetyl chloride (1.0 mL, 1.39 g, 18 mmol) and then pyridine (1.0 mL, 1.0 g, 12 mmol) were added, and the reaction stirred at 0° C. for 1 h. The reaction mixture was then diluted with 10% HCl and extracted two times with methylene chloride. The combined organic extracts were washed with brine, dried over MgSO4, filtered and the solvents were removed in vacuo. The residual crude product was purified by silica gel chromatography (30% ethyl acetate in hexanes) to give the title compound as a white solid, which was immediately used in the next step.

Ethyl-(5,5,8-trimethyl-5,6-dihydro-naphthalen-2-yl)-amine (Compound 166)

General Procedure U: A solution of N-(5,5,8-trimethyl-5,6-dihydro-naphthalen-2-yl)-acetamide (Compound 162, 2.28 g, 10.0 mmol) in 100 mL of diethyl ether was stirred under argon at 0° C., and lithium aluminum hydride (20.0 mL, 20 mmol, 1 M in ether) was added and the reaction stirred at 0° C. to room temperature for 4 h and then heated at 30° C. for 1 h. The reaction was then cooled to 0° C., and carefully quenched with water. Sodium potassium tartrate solution was then added and the reaction stirred for 30 min and extracted twice with ether. The combined organic extracts were washed with brine, dried over MgSO$_4$, filtered and the solvents were removed in vacuo. The residual crude product was purified by silica gel chromatography (10% ethyl acetate in hexanes) to give the title compound as an oil. PNMR δ (CDCl$_3$): 1.16 (t, J=7.1 Hz, 3 H), 1.21 (s, 6 H), 2.03 (s, 3 H), 2.14 (d, J=4.4 Hz, 2 H), 3.16 (q, J=7.1 Hz, 2 H), 5.75 (t, J=4.4 Hz, 1 H), 6.48 (dd, J=2.5, 8.1 Hz, 1 H), 6.55 (d, J=2.5 Hz, 1 H), 7.12 (d, J=8.1 Hz, 1 H).

6-[Ethyl-(5,5,8-trimethyl-5,6-dihydro-naphthalen-2-yl)-amino]-nicotinic acid Compound 170)

To a mixture of 1.78 g (8.3 mmol) of ethyl-(5,5,8-trimethyl-5,6-dihydro-naphthalen-2-yl)-amine (Compound 166) and 0.55 g (3.9 mmol) of 6-fluoro-nicotinic acid was added a small amount of ether and toluene to help stirring. The resulting mixture was heated at 100–150° C. for 1 h. The mixture was cooled. The product was purified by flash chromatography silica, 50% ethyl acetate in hexanes) followed by recrystallization using ethyl acetate:hexane (1:1) to give the title compound as white crystals (158 mg). $^1$H NMR (CDCl$_3$): δ 1.26 (t, J=7.1 Hz, 3 H), 1.30 (s, 6 H), 2.02 (s, 3 H), 2.24 (d, J=4.4 Hz, 2 H), 4.05 (q, J=7.1 Hz, 2 H), 5.82 (t, J=4.4 Hz, 1 H), 6.25 (d, J=9.1 Hz, 1 H), 7.03–7.06 (overlapping s & dd, 2 H), 7.37 (d, J=8.4 Hz, 1 ), 7.83 (dd, J=2.3, 9.1 Hz, 1 H), 8.91 (d, J=2.3 Hz, 1 H).

7-Bromo-1-ethyl-4,4-dimethyl-1,2,3,4-tetrahydro-naphthalen-1-ol

Following General Procedure I, 7-bromo-4,4-dimethyl-3,4-dihydro-2H-naphthalen-1-one (2.02 g, 8.0 mmol) was reacted to give the title compound as an oil and was directly used in the next step.

6-Bromo-4-ethyl-1,1-dimethyl-1,2-dihydro-naphthalene

Following General Procedure J, 7-bromo-1-ethyl-4,4-dimethyl-1,2,3,4-tetrahydro-naphthalen-1-ol (2.25 g, 8.0 mmol) was reacted to give the title compound as an oil. PNMR (CDCl$_3$): δ 1.16 (t, J=7.3 Hz, 3 H), 1.22 (s, 6 H), 2.18 (d, J=4.6 Hz, 2 H), 2.24 (q, J=7.3 Hz, 2 H), 5.80 (t, J=4.5 Hz, 1 H), 7.17(d, J=8.2 Hz, 1 H), 7.31 (dd, J=2.1, 8.2 Hz, 1 H), 7.38 (d, J=2.1 Hz, 1 H).

8-Ethyl-5,5-dimethyl-5,6-dihydro-naphthalen-2-ylamine (Compound 160)

Following General Procedure K, 6-bromo-4-ethyl-1,1-dimethyl-1,2-dihydro-naphthalene (2.04 g, 7.7 mmol) was reacted to give the title compound as an oil. PNMR (CDCl$_3$): δ 1.16 (t, J=7.3 Hz, 3 H), 1.22 (s, 6 H), 2.16 (d, J=4.6 Hz, 2 H), 2.42 (q, J=7.3 Hz, 2 H), 3.57 (s, 2 H), 5.76 (t, J=4.6 Hz, 1 H), 6.57 (dd, J=2.5, 8.2 Hz, 1 H), 6.68 (d, J=2.5 Hz, 1 H), 7.12 (d, J=8.2 Hz, 1 H).

N-(8-Ethyl-5,5-dimethyl-5,6-dihydro-naphthalen-2-yl)-acetamide (Compound 163)

Following General Procedure T, 8-ethyl-5,5-dimethyl-5,6-dihydro-naphthalen-2-ylamine (Compound 160, 1.55 g, 7.7 mmol) was reacted to give the title compound as an oil. PNMR (CDCl₃): δ 1.14 (t, J=7.4 Hz, 3 H), 1.23 (s, 6 H), 2.16 (overlapping s & d, 5 H), 2.42 (q, J=7.4 Hz, 2 H), 5.77 (t, J=4.4 Hz, 1 H), 7.23 (d, J=8.0 Hz, 1 H), 7.35–7.39 (overlapping s & d, 2 H), 7.76 (s, 1 H).

Ethyl-(8-ethyl-5,5-dimethyl-5,6-dihydro-naphthalen-2-yl)-amine (Compound 167)

Following General Procedure U, N-(8-ethyl-5,5-dimethyl-5,6dihydro-naphthalen-2-yl)-acetamide ((Compound 163, 0.43 g, 1.8 mmol) was reacted to give the title compound as an oil.
PNMR δ 1.15 (t, J=7.3 Hz, 3 H), 1.20 (s,6 H), 1.25 (t, J=7.1 Hz, 3 H), 2.14 (d, J=4.5 Hz, 2 H), 2.43 (q, J=7.3 Hz, 2 H), 2.43 (q, J=7.1 Hz, 2 H), 3.42 (s, 1 H), 5.74 (t, J=4.5 Hz, 1 H), 6.47 (dd, J=2.5, 8.2 Hz, 1 H), 6.58 (d, J=2.50 Hz, 1 H), 7.14 (d, J=8.2 Hz, 1 H).

6-[Ethyl-(8-ethyl-5,5-dimethyl-5,6-dihydro-naphthalen-2-yl)-amino]-nicotinic acid (Compound 171)

To a mixture of 0.35 g (1.5 mmol) ethyl-(8-ethyl-5,5-dimethyl-5,6-dihydro-naphthalen-2-yl)-amine (Compound 167 and 0.32 g (2.2 mmol) of 6-fluoro-nicotinic acid was added a small amount of ether and toluene to help stirring. The resulting mixture was heated at 100–150° C. for 1 h. The mixture was cooled. The product was purified by flash chromatography (silica, 50% ethyl acetate in hexanes) followed by recrystallization using ethyl acetate:hexane (1:1) to give the title compound as white crystals (22 mg).
PNMR (CDCl₃): δ 1.13 (t, J=7.3 Hz, 3 H), 1.26 (t, J=7.1 Hz, 3 H), 1.29 (s, 6 H), 2.24 (d, J=4.7 Hz, 2 H), 2.42 (q, J=7.3 Hz, 2 H), 4.06 (q, J=7.1 Hz, 2 H), 5.82 (t, J=4.7 Hz, 1 H), 6.25 (d, J=9.1 Hz, 1 H), 7.04 (dd, J=2.3, 8.3 Hz, 1 H), 7.09 (d, J=2.3 Hz, 1 H), 7.38 (d, J=8.3 Hz, 1 H), 7.83 (dd, J=1.5, 9.1 Hz, 1 H), 8.91 (d, J=1.5 Hz, 1 H).

7-Bromo-1-isopropyl-4,4-dimethyl- 1,2,3,4-tetrahydro-naphthalen-1-ol

Following General Procedure I, 7-bromo-4,4-dimethyl-3,4-dihydro-2H-naphthalen-1-one (2.08 g, 8.2 mmol) was reacted to give the title compound as oil. PNMR (CDCl₃): δ 0.70–2.70 (m, 17 H), 7.22 (d, J=8.4 Hz, 1 H), 7.34 (dd, J=2.2, 8.4 Hz, 1 H), 7.64 (d, J=2.2 Hz, 1 H)

6-Bromo-4-isopropyl-1,1-dimethyl-1,2-dihydro-naphthalene

Following General Procedure S, 7-bromo-1-isopropyl-4,4-methyl-1,2,3,4-tetrahydro-naphthalen-1-ol (1.20 g, 4.0 mmol) was reacted to give the title compound as an oil.
PNMR (CDCl₃): δ 1.16 (d, J=6.7 Hz, 6 H), 1.22 (s, 6 H), 2.18 (overlapping s & d, 5 H), 2.42 (p, J=6.7 Hz, 1 H), 5.82 (t, J=4.5 Hz, 1 H), 7.18 (d, J=8.2 Hz, 1 H), 7.31 (dd, J=2.1, 8.2 Hz, 1 H), 7.43 (d, J=2.2 Hz, 1 H).

8-Isopropyl-5,5-dimethyl-5,6-dihydro-naphthalen-2-ylamine (Compound 161)

Following General Procedure K, 6-bromo-4-isopropyl-1,1-dimethyl-1,2-dihydro-naphthalene (0.57 g, 2.0 mmol) was reacted to give the title compound as an oil.
PNMR (CDCl₃): δ 1.16 (d, J=6.7 Hz, 6 H), 1.20 (s, 6 H), 2.05 (s, 3 H), 2.14 (d, J=4.4 Hz, 1 H), 2.89 (p, J=6.7 Hz, 1 H), 3.58 (s, 2 H, NH), 5.77 (t, J=4.4 Hz, 1 H), 6.56 (dd, J=2.4, 8.1 Hz, 1 H), 6.72 (d, J=2.4 Hz, 1 H), 7.11 (d, J=8.1 Hz, 1 H).

N-(8-Isopropyl-5,5-dimethyl-5,6-dihydro-naphthalen-2-yl)-acetamide (Compound 164).

Following General Procedure T, 8-isopropyl-5,5-dimethyl-5,6-dihydro-naphthalen-2-ylamine (Compound 161, 0.44 g, 2.0 mmol) was reacted to give the title compound as an oil.
PNMR (CDCl₃): δ 1.16 (d, J=6.6 Hz, 6 H), 1.22 (s, 6 H), 2.16 (overlapping s & d, 5 H), 2.42 (p, J=6.6 Hz, 1 H), 5.80 (t, J=4.4 Hz, 1 H), 7.25 (d, J=8.3 Hz, 1 H), 7.29 (s, 1 H), 7.23 (dd, J=2.2, 8.3 Hz, 1 H), 7.45 (d, J=2.2 Hz, 1 H).

Ethyl-(8-isopropyl-5,5-dimethyl-5,6-dihydro-naphthalen-2-yl)-amine (Compound 168)

Following General Procedure U, N-(8-isopropyl-5,5-dimethyl-5,6-dihydro-naphthalen-2-yl)-acetamide (Compound 164, 0.23 g, 0.89 mmol) was reacted to give the title compound as an oil.
PNMR (CDCl₃): δ 1.16 (d, J=6.8 Hz, 6 H), 1.19 (s, 6 H), 1.25 (t, J=7.1 Hz, 3 H), 2.13 (d, J=4.8 Hz, 1 H), 2.90 (p, J=6.8 Hz, 1 H),3.16 (q, J=7.1 Hz, 1 H), 3.43 (s, 1 H), 5.76 (t, J=4.8 Hz, 1 H), 6.47 (dd, J=2.4, 8.2 Hz, 1 H), 6.64 (d, J=2.4 Hz, 1 H), 7.13 (d, J=8.2 Hz, 1 H).

6-[Ethyl-(8-isopropyl-5,5-dimethyl-5,6-dihydro-naphthalen-2-yl)-amino]-nicotinic acid (Compound 172)

To a mixture of 85 mg (0.35 mmol) of ethyl-(8-isopropyl-5,5-dimethyl-5,6-dihydro-naphthalen-2-yl)-amine (Compound 168) and 0.10 g (0.71 mmol) of 6-fluoro-nicotinic acid was added a small amount of ether and toluene to help stirring. The resulting mixture was heated at 100–150° C. for 1 h. The mixture was cooled. Purification was done using flash chromatography (silica, 50% ethyl acetate in hexanes) followed by recrystallization using ethyl. acetate:hexane (1:1) to give the title compound as white crystals (26 mg).
PNMR (CDCl₃): δ 1.13 (d, J=6.7 Hz, 6 H), 1.36 (t, J=7.1 Hz, 3 H), 1.28 (s, 6 H), 2.23 (d, J=4.4 Hz, 2 H), 2.85 (p, J=6.7 Hz, 1 H), 4.06 (q, J=7.1 Hz, 2 H), 5.83 (t, J=4.4 Hz, 1 H),6.24 (d, J=9.1 Hz, 1 H), 7.04 (dd, J=2.1, 8.1 Hz, 1 H), 7.14 (d, J=2.1 Hz, 1 H), 7.39 (d, J=8.1 Hz, 1 H), 7.83 (dd, J=2.1, 9.1 Hz, 1 H), 8.92 (d, J=2.1 Hz, 1 H).

N-(8-t-Butyl-5,5-dimethyl-5,6-dihydro-naphthalen-2-yl)-acetamide (Compound 165)

Following General Procedure T, 8-t-butyl-5,5-dimethyl-5,6-dihydro-naphthalen-2-ylamine (Compound 83, 0.14 g, 0.61 mmol) was reacted to give the title compound as a solid which was immediately used in the next step.

8-t-Butyl-5,5-dimethyl-5,6-dihydro-naphthalene-2-yl)-ethyl-amine (Compound 169)

Following General Procedure U, N-(8-t-butyl-5,5-dimethyl-5,6-dihydro-naphthalen-2-yl)-acetamide (Compound 165, 0.16 g, 0.59 mmol) was reacted to give the title compound as an oil.
PNMR δ (CDCl₃): 1.18 (s, 6 H), 1.25 (t, J=7.1 Hz, 3 H), 1.35 (s, 9 H), 2.08 (d, J=4.4 Hz, 2 H), 3.16 (q, J=7.1 Hz, 2 H), 3.41 (s, 1 H), 5.92 (t, J=4.4 Hz, 1 H), 6.43 (dd, J=2.5, 8.1 Hz, 1 H), 6.97 (d, J=2.5 Hz, 1 H), 7.12 (d, J=8.1 Hz, 1 H).

6-[(8-t-Butyl-5,5-dimethyl-5,6-dihydro-naphthalen-2-yl)-ethyl-amino]-nicotinic acid (Compound 173)

To a mixture of 85 mg (0.37 mmol) of (8-t-butyl-5,5-dimethyl-5,6-dihydro-naphthalen-2-yl)ethyl-amine (Compound 169) and 0.11 g (0.78 mmol) of 6-fluoro-nicotinic acid was added a small amount of ether and toluene to help stirring. The resulting mixture was heated at 100–150° C. for 1 h. The mixture was cooled. The product was purified by flash chromatography (silica, 50% ethyl acetate in hexanes to give the title compound as a white solid (12 mg).
¹H NMR (CDCl₃): δ 1.26 (overlapping s & t, 12 H), 1.30 (s, 6 H), 2.10 (d, J=4.4 Hz, 2 H), 4.04 (q, J=7.1 Hz, 2 H), 6.02 (t, J=4.4 Hz, 1 H), 6.27 (d, J=9.1 Hz, 1 H), 7.03 (dd, J=2.1, 8.Hz, 1 H), 7.38 (d, J=8.1 Hz, 1 H), 7.47 (d, J=2.1 Hz, 1 H), 7.83 (dd, J=2.1, 9.1 Hz, 1 H), 8.92 (d, J=2.1 Hz, 1 H).

What is claimed is:

1. A compound of the formula

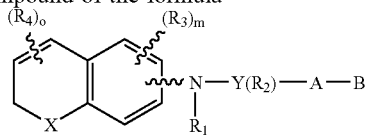

where X is O, S, or $C(R)_2$;

R is H or alkyl of 1 to 6 carbons;

$R_1$ is H, alkyl of 1 to 10 carbons, alkenyl of 2 to 6 carbons; phenyl-$C_1$-$C_6$ alkyl, or $C_1$-$C_6$-alkylphenyl;

$R_2$ is H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, $CF_3$, fluoro substituted alkyl of 1 to 6 carbons, OH, SH, alkoxy of 1 to 10 carbons, fluoroalkoxy of 1 to 6 carbons, alkylthio of 1 to 6 carbons; benzyloxy $C_1$-$C_6$ alkyl substituted benzyloxy, halogen substituted benzyloxy, phenyloxy, $C_1$-$C_6$ alkyl substituted phenyloxy, or halogen substituted phenyloxy;

$R_4$ is independently H, alkyl of 1 to 6 carbons, or F;

Y is a group, said pyridyl group being optionally substituted with one or two $R_2$ groups;

m is an integer having the values 0 to 3;

o is an integer having the values 0 to 4;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound.

2. A compound in accordance with claim 1 where X is $C(R)_2$.

3. A compound in accordance with claim 1 where X is S.

4. A compound in accordance with claim 1 where X is O.

5. A compound in accordance with claim 1 where the A-B group represents $(CH_2)_qCOOR_8$ or $(CH_2)_qCOOH$ where q is 0, or a pharmaceutically acceptable salt thereof.

6. A compound in accordance with claim 1 where $R_1$ is alkyl of 1 to 10 carbons or alkenyl of 2 to 6 carbons.

7. A compound in accordance with claim 1 where $R_4$ is independently H or alkyl of 1 to 6 carbons.

8. A compound in accordance with claim 1 where $R_1$ is alkyl of 1 to 10 carbons or alkenyl of 2 to 6 carbons, $R_4$ is independently H or alkyl of 1 to 6 carbons and the A-B group represents $(CH_2)_qCOOR_8$ or $(CH_2)_qCOOH$ where q is 0, or a pharmaceutically acceptable salt thereof.

9. A compound that has the structure of formula (iii)

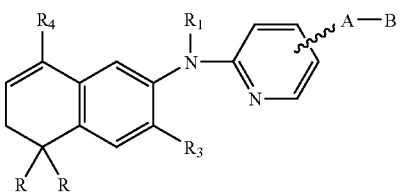

where R is independently H or alkyl of 1 to 6 carbons;

$R_1$ is H or alkyl of 1 to 10 carbons or alkenyl of 2 to 6 carbons;

$R_3$ is independently alkyl of 1 to 6 carbons, F, Cl, Br, I, $CF_3$, fluoro substituted alkyl of 1 to 6 carbons, OH, SH, alkoxy of 1 to 10 carbons, fluoroalkoxy of 1 to 6 carbons, alkylthio of 1 to 6 carbons; benxyloxy, $C_1$-$C_6$ alkyl substituted benzyloxy, halogen substituted benzyloxy, phenyloxy, $C_1$—$C_6$ alkyl substituted phenyloxy, or halogen substituted phenyloxy;

$R_4$ is H or alkyl of 1 to 6 carbons;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and B is hydrogen, COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound.

10. A compound in accordance with claim 9 where $R_4$ and $R_1$ both are alkyl.

11. A compound in accordance with claim 9 where the A—B group represents $(CH_2)_qCOOR_8$ or $(CH_2)_qCOOH$ where q is 0, or a pharmaceutically acceptable salt thereof.

12. A compound of the formula

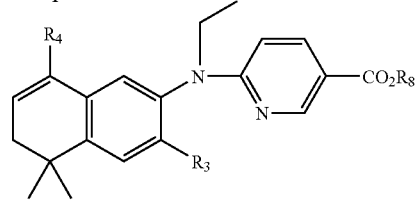

where $R_3$ is H, or alkyl of 1 to 6 carbons;

$R_4$ is alkyl of 1 to 6 carbons, and $R_8$ is H or alkyl of 1 to 6 carbons, or a pharmaceutically acceptable salt of said compound.

13. A compound in accordance with claim 12 where $R_4$ is methyl, ethyl, i-propyl or t-butyl.

14. A compound in accordance with claim 12 where $R_3$ is H, or n-butyloxy.

15. A compound in accordance with claim 12 where $R_8$ is H or ethyl.

16. A compound in accordance with claim 12 where $R_4$ is methyl, ethyl, i-propyl or t-butyl;

$R_3$ is H, or n-butyloxy, and $R_8$ is H or ethyl.

17. A compound in accordance with claim 16 where $R_8$ is H or ethyl.

* * * * *